United States Patent
Usui

(10) Patent No.: US 11,633,240 B2
(45) Date of Patent: Apr. 25, 2023

(54) MEDICAL SYSTEM, CONTROL DEVICE OF MEDICAL SUPPORT ARM, AND CONTROL METHOD OF MEDICAL SUPPORT ARM

(71) Applicant: Sony Corporation, Tokyo (JP)

(72) Inventor: Masaru Usui, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 769 days.

(21) Appl. No.: 16/614,802

(22) PCT Filed: Apr. 11, 2018

(86) PCT No.: PCT/JP2018/015207
§ 371 (c)(1),
(2) Date: Nov. 19, 2019

(87) PCT Pub. No.: WO2018/216382
PCT Pub. Date: Nov. 29, 2018

(65) Prior Publication Data
US 2020/0197108 A1  Jun. 25, 2020

(30) Foreign Application Priority Data

May 26, 2017  (JP) .............................. JP2017-104748

(51) Int. Cl.
*A61B 34/00* (2016.01)
*A61B 34/30* (2016.01)
*A61B 90/50* (2016.01)
*B25J 19/06* (2006.01)

(52) U.S. Cl.
CPC .............. *A61B 34/30* (2016.02); *A61B 90/50* (2016.02); *B25J 19/06* (2013.01)

(58) Field of Classification Search
CPC ......... A61B 34/30; A61B 90/50; A61B 90/37; A61B 2034/2059; A61B 2090/064; A61B 2090/066; A61B 34/37; B25J 19/06
See application file for complete search history.

(56) References Cited

U.S. PATENT DOCUMENTS 10,478,634 B2 *  11/2019  Schwarz .............. A61B 18/203

FOREIGN PATENT DOCUMENTS

| CN | 1864938 A | 11/2006 |
| CN | 104470456 A | 3/2015 |
| CN | 104661612 A | 5/2015 |
| JP | 2000-300579 A | 10/2000 |

(Continued)

OTHER PUBLICATIONS

International Search Report and Written Opinion dated Jun. 12, 2018 for PCT/JP2018/015207 filed on Apr. 11, 2018, 14 pages including English Translation of the International Search Report.

*Primary Examiner* — Ian Jen
(74) *Attorney, Agent, or Firm* — Xsensus LLP

(57) ABSTRACT

A harmonized operation of a plurality of medical support arms is controlled more accurately. There is provided a medical system including an operation control unit configured to control, on the basis of information regarding a movable range (300a) of a first medical support arm (10a) being a control target, information regarding the movable range (300b) of a second medical support arm (10b) to be used together with the first medical support arm (10a), and a space position of a working point (Pa) in the first medical support arm (10a), an operation of the working point (Pa).

22 Claims, 23 Drawing Sheets

(56) References Cited

FOREIGN PATENT DOCUMENTS

| | | |
|---|---|---|
| JP | 2001-448 A | 1/2001 |
| JP | 2006-321027 A | 11/2006 |
| JP | 2007-29232 A | 2/2007 |
| JP | 2010-240793 A | 10/2010 |
| JP | 2015-527910 A | 9/2015 |
| WO | 2015/046081 A1 | 4/2015 |
| WO | 2017/169096 A1 | 10/2017 |

\* cited by examiner

MEDICAL SYSTEM, CONTROL DEVICE OF MEDICAL SUPPORT ARM, AND CONTROL METHOD OF MEDICAL SUPPORT ARM

CROSS-REFERENCE TO RELATED APPLICATIONS

The present application is based on PCT filing PCT/JP2018/015207, filed Apr. 11, 2018, which claims priority to JP 2017-104748, filed May 26, 2017, the entire contents of each are incorporated herein by reference.

TECHNICAL FIELD

The present disclosure relates to medical system, a control device of a medical support arm, and a control method of a medical support arm.

BACKGROUND ART

For example, as described in the following patent document, in the medical field, in some cases, a medical device in which a medical unit (camera, forceps, etc.) is provided at an arm portion distal end has been conventionally used when various practices (operation, checkup, etc.) are performed.

Citation List

PATENT DOCUMENT

Patent Document 1: WO 2015/046081 A

SUMMARY OF THE INVENTION

Problems to be Solved by the Invention

However, while a manually-manipulable medical support arm can be intuitively operated by a manipulator, if an operation is erroneously performed, unexpected situations such as contact of an arm portion distal end to a patient or a practitioner might occur. For ensuring the safety in using a medical support arm, instead of depending only on the visual or tactile determination of a manipulator, security is required to be guaranteed by operability and operation restriction on a device side. Moreover, in a case where a plurality of medical support arms is used in a practice, harmonized operation of the plurality of medical support arms is required.

In view of the foregoing, the present disclosure proposes a medical system, a control device of a medical support arm, and a control method of a medical support arm that are novel and improved, and can more accurately control a harmonized operation of a plurality of medical support arms.

Solutions to Problems

According to the present disclosure, there is provided a medical system including an operation control unit configured to control, on the basis of information regarding a movable range of a first medical support arm being a control target, information regarding the movable range of a second medical support arm to be used together with the first medical support arm, and a space position of a working point in the first medical support arm, an operation of the working point.

Furthermore, according to the present disclosure, there is provided a control device of a medical support arm including an operation control unit configured to control, on the basis of information regarding a movable range of a first medical support arm being a control target, information regarding the movable range of a second medical support arm to be used together with the first medical support arm, and a space position of a working point in the first medical support arm, an operation of the working point.

Furthermore, according to the present disclosure, there is provided a control method of a medical support arm, and the control method includes controlling, by a processor, on the basis of information regarding a movable range of a first medical support arm being a control target, information regarding the movable range of a second medical support arm to be used together with the first medical support arm, and a space position of a working point in the first medical support arm, an operation of the working point.

Effects of the Invention

As described above, according to the present disclosure, it becomes possible to more accurately control a harmonized operation of a plurality of medical support arms.

Note that the above-described effect is not always limitative, and together with the above-described effect or in place of the above-described effect, any of the effects described in this specification, or other effects recognized from this specification may be caused.

MODE FOR CARRYING OUT THE INVENTION

Figure 1:
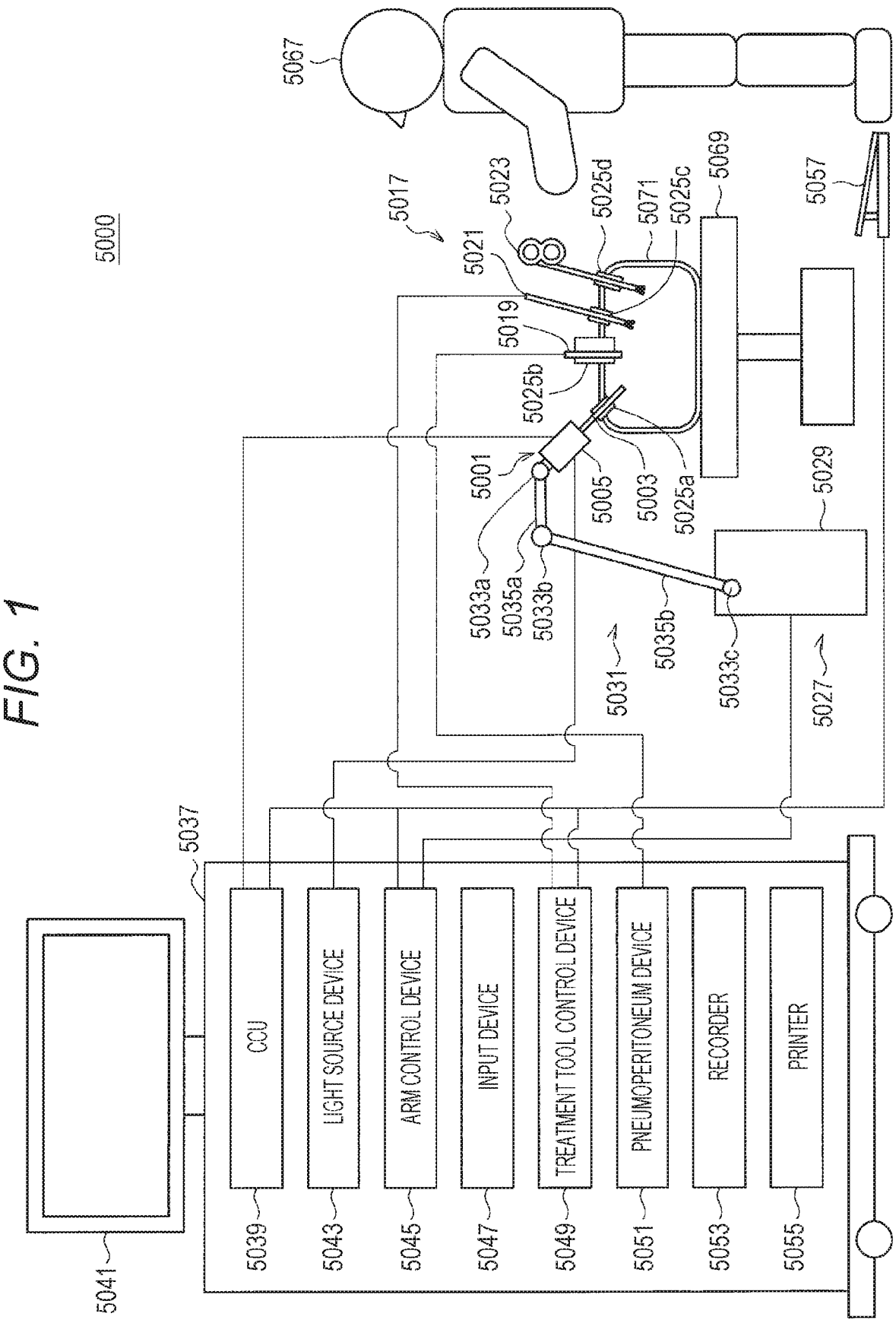
FIG. 1 is a diagram illustrating an example of a schematic configuration of an endoscopic operation system to which a medical support arm device according to the present disclosure can be applied.

Hereinafter, a preferred embodiment of the present disclosure will be described in detail with reference to the attached drawings. Note that, in this specification and the drawings, the redundant description will be omitted by allocating the same reference numerals to the components having substantially the same functional configuration.

Note that the description will be given in the following order.
1. Consideration about medical support arm device
1-1. Endoscope
1-2. Various devices mounted on cart
1-3. Schematic configuration of medical support arm device
1-4. Light source device
1-5. Camera head and CCU
2. Embodiment of present disclosure
2-1. External appearance of support arm device
2-2. Generalized inverse dynamics
2-3. Ideal joint control
2-4. Configuration of support arm control system
2-5. Overview of movable range restriction and movable range expansion of arm
2-6. Overview of harmonized control of plurality of support arms
2-7. Configuration example for implementing harmonized control of plurality of support arms
2-8. Flow of control
2-9. Variations of safety movable range and unsafe region
3. Hardware configuration
4. Conclusion 1. Consideration about Medical Support Arm Device First, a background in which the present inventors have eventually conceived the present disclosure will be described for clarifying the present disclosure.

An application example in a case where a support arm device according to an embodiment of the present disclosure is used for a medical purpose will be described with reference to FIG. 1. FIG. 1 is a diagram illustrating an example of a schematic configuration of an endoscopic operation system 5000 to which a support arm device according to the present disclosure can be applied. FIG. 1 illustrates a state in which an operator (doctor) 5067 is performing an operation on a patient 5071 laid on a patient bed 5069, using the endoscopic operation system 5000. As illustrated in the drawing, the endoscopic operation system 5000 includes an endoscope 5001, other operation tools 5017, a support arm device 5027 supporting the endoscope 5001, and a cart 5037 on which various devices for an endoscopic operation are mounted.

In the endoscopic operation, instead of opening an abdomen by cutting an abdomen wall, the abdomen wall is punctured with a plurality of cylindrical hole opening tools called trocars 5025*a* to 5025*d*. Then, a lens barrel 5003 of the endoscope 5001 and the other operation tools 5017 are inserted into a body cavity of the patient 5071 through the trocars 5025*a* to 5025*d*. In the example illustrated in the drawing, as the other operation tools 5017, a pneumoperitoneum tube 5019, an energy treatment tool 5021 and forceps 5023 are inserted into the body cavity of the patient 5071. The energy treatment tool 5021 is a treatment tool for incising and detaching body tissues or performing sealing of blood vessels or the like by high-frequency current or ultrasonic vibration. However, the operation tools 5017 illustrated in the drawing are merely examples, and various operation tools generally used in an endoscopic operation, such as tweezers or retractors, for example, may be used as the operation tools 5017.

An image of an operative portion in the body cavity of the patient 5071 that has been captured by the endoscope 5001 is displayed on a display device 5041. While viewing the image of the operative portion that is displayed on the display device 5041, in real time, the operator 5067 performs treatment such as cutting of a diseased portion, for example, using the energy treatment tool 5021 or the forceps 5023. Note that the pneumoperitoneum tube 5019, the energy treatment tool 5021, and the forceps 5023 are supported by the operator 5067, an assistant, or the like during the operation, which is not illustrated in the drawing.

<<1-1. Endoscope>>

The endoscope 5001 includes the lens barrel 5003 in which a region corresponding to a predetermined length from a distal end is inserted into the body cavity of the patient 5071, and a camera head 5005 connected to a proximal end of the lens barrel 5003. In the example illustrated in the drawing, the endoscope 5001 formed as a so-called rigid scope including a rigid lens barrel 5003 is illustrated, but the endoscope 5001 may be formed as a so-called flexible scope including a flexible lens barrel 5003.

An aperture into which an objective lens is fit is provided at the distal end of the lens barrel 5003. A light source device 5043 is connected to the endoscope 5001, and light generated by the light source device 5043 is guided to the distal end of the lens barrel 5003 by a light guide extended inside the lens barrel 5003, and emitted onto an observation target in the body cavity of the patient 5071, via the objective lens. Note that the endoscope 5001 may be a forward-viewing endoscope, a forward-oblique viewing endoscope, or a side viewing endoscope.

An optical system and an image sensor are provided inside the camera head 5005, and reflected light from the observation target (observation light) is condensed to the image sensor by the optical system. The observation light is photoelectrically converted by the image sensor, and an electrical signal corresponding to the observation light, that is to say, an image signal corresponding to an observation image is generated. The image signal is transmitted to a camera control unit (CCU) 5039 as RAW data. Note that the camera head 5005 has a function of adjusting a magnification and focal length by appropriately driving the optical system.

Note that the camera head 5005 may be provided with a plurality of image sensors for supporting stereoscopic view (3D display) or the like, for example. In this case, a plurality of systems of relay optical systems is provided inside the lens barrel 5003 for guiding observation light to each of the plurality of image sensors.

<<1-2. Various Devices Mounted on Cart>>

The CCU 5039 includes a central processing unit (CPU), a graphics processing unit (GPU), or the like, and comprehensively controls operations of the endoscope 5001 and the display device 5041. Specifically, the CCU 5039 performs, on the image signal received from the camera head 5005, various types of image processing for displaying an image that is based on the image signal, such as development processing (demosaic processing), for example. The CCU 5039 provides the image signal subjected to the image processing, to the display device 5041. Furthermore, the CCU 5039 transmits a control signal to the camera head 5005, and controls the driving. The control signal can include information regarding an imaging condition such as magnification or focal length.

By the control from the CCU 5039, the display device 5041 displays an image that is based on the image signal subjected to the image processing performed by the CCU 5039. In a case where the endoscope 5001 supports high resolution image capturing such as 4K (the number of horizontal pixels 3840×the number of vertical pixels 2160) or 8K (the number of horizontal pixels 7680×the number of vertical pixels 4320), for example, and/or supports 3D display, a display device that can perform high resolution display and/or a display device that can perform 3D display is used as the display device 5041 so as to respectively corresponding thereto. In a case where the endoscope 5001 supports high resolution image capturing such as 4K or 8K, by using a display device with a size of 55 inches or more as the display device 5041, a sense of immersion can be further obtained. Furthermore, a plurality of display devices 5041 having different resolutions or sizes may be provided in accordance with use applications.

The light source device 5043 includes, for example, a light source such as a light emitting diode (LED), and supplies irradiation light to be used in capturing an image of an operative portion, to the endoscope 5001.

An arm control device 5045 includes a processor such as a CPU, for example, and controls the driving of the arm portion 5031 of the support arm device 5027 in accordance with a predetermined control method, by operating in accordance with a predetermined program.

An input device 5047 is an input interface for the endoscopic operation system 5000. A user can perform input of various types of information or instruction input to the endoscopic operation system 5000 via the input device 5047. For example, via the input device 5047, the user inputs various types of information regarding an operation, such as body information regarding a patient, or information regarding an operative method of an operation. Furthermore, for example, the user inputs, via the input device 5047, an instruction for driving the arm portion 5031, an instruction for changing an imaging condition (type of irradiation light, magnification, focal length, and the like) to be used by the endoscope 5001, an instruction for driving the energy treatment tool 5021, and the like.

The type of the input device 5047 is not limited, and various known input devices may be used as the input device 5047. As the input device 5047, for example, a mouse, a keyboard, a touch panel, a switch, a foot switch 5057, a lever, and/or the like can be applied. In a case where a touch panel is used as the input device 5047, the touch panel may be provided on a display surface of the display device 5041.

Alternatively, the input device 5047 is a device worn by the user, such as a glasses-type wearable device or a head mounted display (HMD), for example, and various inputs are performed in accordance with a gesture or a visual line of the user that is detected by these devices. Furthermore, the input device 5047 includes a camera that can detect a motion of the user, and various inputs are performed in accordance with a gesture or a visual line of the user that is detected from a video captured by the camera. Moreover, the input device 5047 includes a microphone that can collect voice of the user, and various inputs are performed by voice via the microphone. In this manner, by the input device 5047 being configured to input various types of information in a non-contact manner, it becomes possible for the user (for example, the operator 5067) belonging to a clean region in particular, to manipulate a device belonging to an unclean region, in a noncontact manner. Furthermore, because it becomes possible for the user to manipulate a device without separating the hand from a holding operation tool, the convenience of the user is enhanced.

A treatment tool control device 5049 controls the driving of the energy treatment tool 5021 for performing cauterization or incising of body tissues, sealing of blood vessels or the like. A pneumoperitoneum device 5051 feeds gas into the body cavity via the pneumoperitoneum tube 5019 for swelling the body cavity of the patient 5071 for the purpose of ensuring a viewing field obtained by the endoscope 5001 and securing a work space of an operator. A recorder 5053 is a device that can record various types of information regarding an operation. A printer 5055 is a device that can print various types of information regarding an operation, in various formats such as text, images, or graphs.

<<1-3. Schematic Configuration of Medical Support Arm Device>>

The support arm device 5027 includes the arm portion 5031 extending from a base portion 5029. In the example illustrated in the drawing, the arm portion 5031 includes joint portions 5033a, 5033b, and 5033c, and links 5035a and 5035b, and is driven in accordance with a control command from the arm control device 5045. By the arm portion 5031, the endoscope 5001 is supported, and a position and an orientation thereof are controlled. With this configuration, the position of the endoscope 5001 can be stably fixed.

The support arm device 5027 includes the base portion 5029 being a base, and the arm portion 5031 extending from the base portion 5029. In the example illustrated in the drawing, the arm portion 5031 includes the plurality of joint portions 5033a, 5033b, and 5033c, and the plurality of the links 5035a and 5035b coupled by the joint portion 5033b, but the configuration of the arm portion 5031 is illustrated in FIG. 1 in a simplified manner for the sake of simplicity. Actually, the shapes, the numbers, and the arrangements of the joint portions 5033a to 5033c and the links 5035a and 5035b, directions of rotation axes of the joint portions 5033a to 5033c, and the like can be appropriately set in such a manner that the arm portion 5031 has a desired degree of freedom. For example, the arm portion 5031 can be preferably formed to have a degree of freedom being a six-degree of freedom or more. With this configuration, because it becomes possible to freely move the endoscope 5001 within a movable range of the arm portion 5031, it becomes possible to insert the lens barrel 5003 of the endoscope 5001 into the body cavity of the patient 5071 from a desired direction.

The joint portions 5033a to 5033c are provided with an actuator, and the joint portions 5033a to 5033c are configured to be rotatable around a predetermined rotation axis by the driving of the actuator. By the driving of the actuator being controlled by the arm control device 5045, a rotational angle of each of the joint portions 5033a to 5033c is controlled, and the driving of the arm portion 5031 is controlled. With this configuration, the control of the position and the orientation of the endoscope 5001 can be implemented. At this time, the arm control device 5045 can control the driving of the arm portion 5031 by various known control methods such as force control or positioning control.

For example, by the operator 5067 appropriately performing operation input via the input device 5047 (including the foot switch 5057), the driving of the arm portion 5031 may be appropriately controlled by the arm control device 5045 in accordance with the operation input, and the position and the orientation of the endoscope 5001 may be controlled. By the control, the endoscope 5001 at the distal end of the arm portion 5031 can be moved from an arbitrary position to an arbitrary position, and then, supported in a fixed manner at the position set after the movement. Note that the arm portion 5031 may be manipulated by a so-called master-slave method. In this case, the arm portion 5031 can be remotely controlled by the user via the input device 5047 installed at a location distant from an operating room.

Furthermore, in a case where force control is applied, the arm control device 5045 may receive external force from the user, and perform so-called power assist control of driving the actuator of each of the joint portions 5033a to 5033c in such a manner that the arm portion 5031 smoothly moves in accordance with the external force. With this configuration, when the user moves the arm portion 5031 while directly touching the arm portion 5031, the arm portion 5031 can be moved by relatively small force. Accordingly, it becomes possible to move the endoscope 5001 more intuitively by an easier operation, and it is possible to enhance the convenience of the user.

Here, generally, in an endoscopic operation, the endoscope 5001 has been supported by a doctor called a scopist. In contrast to this, by using the support arm device 5027, it becomes possible to fix the position of the endoscope 5001 more surely without using a human hand. Thus, it becomes possible to stably obtain an image of an operative portion and smoothly perform an operation.

Note that the arm control device 5045 needs not be always provided on the cart 5037. Furthermore, the arm control device 5045 needs not be always a single device. For example, the arm control device 5045 may be provided for each of the joint portions 5033a to 5033c of the arm portion 5031 of the support arm device 5027, and driving control of the arm portion 5031 may be implemented by mutual cooperation between a plurality of arm control devices 5045.

<<1-4. Light Source Device>>

The light source device 5043 supplies, to the endoscope 5001, irradiation light used when an image of an operative portion is captured. The light source device 5043 includes, for example, an LED, a laser light source, or a white light source formed by a combination of these. At this time, in a case where a white light source is formed by a combination of RGB laser light sources, because it is possible to accurately control an output strength and an output timing of each color (each wavelength), it is possible to adjust white balance of a captured image in the light source device 5043. Furthermore, in this case, it is also possible to emit laser light from each of the RGB laser light sources onto an observation target in a time-division manner, and capture images respectively corresponding to RGB in a time-division manner by controlling the driving of an image sensor of the camera head 5005 in synchronization with the emission timing. According to the method, a color image can be obtained without providing a color filter on the image sensor.

Furthermore, the driving of the light source device 5043 may be controlled in such a manner that the intensity of light to be output changes every predetermined time. By controlling the driving of the image sensor of the camera head 5005 in synchronization with the change timing of the light intensity, acquiring images in a time-division manner, and combining the images, it is possible to generate a high dynamic range image without containing so-called under exposure and over exposure.

Furthermore, the light source device 5043 may be configured to supply light in a predetermined wavelength band corresponding to special light observation. In the special light observation, so-called narrow band imaging is performed in the following manner. More specifically, by emitting light in a narrower band as compared with irradiation light (in other words, white light) used in normal observation, using wavelength dependency of light absorption in body tissue, for example, an image of a predetermined body tissue such as blood vessels of a mucous membrane surface layer is captured with high contrast. Alternatively, in the special light observation, fluorescence observation of obtaining an image by fluorescence generated by emitting excitation light may be performed. In the fluorescence observation, observation (autofluorescence observation) of emitting excitation light onto a body tissue and observing fluorescence from the body tissue, observation of locally injecting reagent such as indocyanine green (ICG) to a body tissue, emitting excitation light corresponding to fluorescence wavelength of the reagent onto the body tissue, and obtaining a fluorescence image, or the like is performed. The light source device 5043 can be configured to supply narrow band light and/or excitation light that corresponds to such special light observation.

<<1-5. Camera Head and CCU>>

Figure 2:
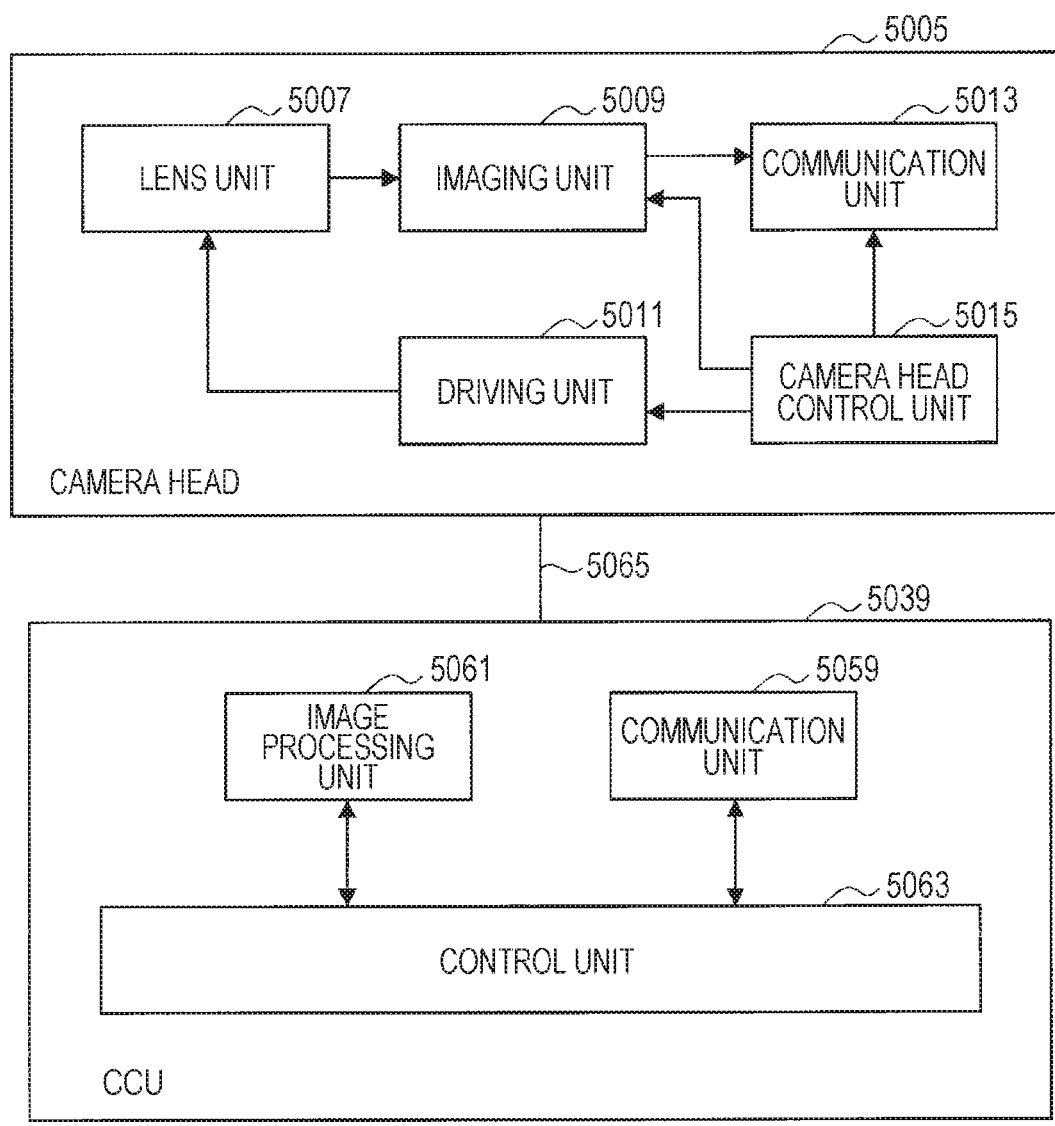
FIG. 2 is a block diagram illustrating an example of functional configurations of a camera head and a CCU illustrated in FIG. 1.

Functions of the camera head 5005 and the CCU 5039 of the endoscope 5001 will be described in more detail with reference to FIG. 2. FIG. 2 is a block diagram illustrating an example of functional configurations of the camera head 5005 and the CCU 5039 illustrated in FIG. 1.

Referring to FIG. 2, the camera head 5005 includes, as functions thereof, a lens unit 5007, an imaging unit 5009, a driving unit 5011, a communication unit 5013, and a camera head control unit 5015. Furthermore, the CCU 5039 includes, as functions thereof, a communication unit 5059, an image processing unit 5061, and a control unit 5063. The camera head 5005 and the CCU 5039 are connected by a transmission cable 5065 in such a manner that communication can be bidirectionally performed.

First, a functional configuration of the camera head 5005 will be described. The lens unit 5007 is an optical system provided at a connection portion with the lens barrel 5003. Observation light taken in from the distal end of the lens barrel 5003 is guided to the camera head 5005 and enters the lens unit 5007. The lens unit 5007 includes a plurality of lenses including a zoom lens and a focus lens. The optical characteristic of the lens unit 5007 is adjusted so as to condense observation light onto the light receiving surface of an image sensor of the imaging unit 5009. Furthermore, the zoom lens and the focus lens are configured to be movable in positions on an optical axis for adjusting magnification and focal point of a captured image.

The imaging unit 5009 includes an image sensor, and is disposed on a subsequent stage of the lens unit 5007. The observation light having passed through the lens unit 5007 is condensed onto the light receiving surface of the image sensor, and an image signal corresponding to an observation image is generated. The image signal generated by the imaging unit 5009 is provided to the communication unit 5013.

As the image sensor included in the imaging unit 5009, for example, a complementary metal oxide semiconductor (CMOS) image sensor that has a Bayer array and can perform color image capturing is used. Note that an image sensor that supports high resolution image capturing of 4K or more, for example, may be used as the image sensor. By a high resolution image of an operative portion being obtained, it becomes possible for the operator 5067 to recognize the state of the operative portion in more detail recognize, and advance an operation more smoothly.

Furthermore, the image sensor included in the imaging unit 5009 includes a pair of image sensors for respectively acquiring image signals for the right eye and the left eye so as to perform 3D display. By 3D display being performed, it becomes possible for the operator 5067 to more accurately recognize the depth of a living tissue in the operative portion. Note that, in a case where the imaging unit 5009 has a multi-imager configuration, a plurality of systems of lens units 5007 is provided so as to correspond to the respective image sensors.

Furthermore, the imaging unit 5009 needs not be always provided in the camera head 5005. For example, the imaging unit 5009 may be provided in the lens barrel 5003 following an objective lens.

The driving unit 5011 includes an actuator, and moves the zoom lens and the focus lens of the lens unit 5007 by a predetermined distance along the optical axis in accordance with the control from the camera head control unit 5015. With this configuration, a magnification and a focal point of a captured image to be obtained by the imaging unit 5009 can be appropriately adjusted.

The communication unit 5013 includes a communication device for exchanging various types of information with the CCU 5039. The communication unit 5013 transmits the image signal obtained from the imaging unit 5009, to the CCU 5039 via the transmission cable 5065 as RAW data. At this time, the image signal is preferably transmitted by optical communication for displaying a captured image of an operative portion with low latency. This is because, in an operation, since the operator 5067 performs the operation while observing a state of a diseased portion using a captured image, for performing an operation more safely and surely, a moving image of an operative portion is required to be displayed in real time as far as possible. In a case where optical communication is performed, the communication unit 5013 is provided with a photoelectric conversion module for photoelectrically converting an electrical signal into an optical signal. The image signal is converted into an optical signal by the photoelectric conversion module, and then, transmitted to the CCU 5039 via the transmission cable 5065.

Furthermore, the communication unit 5013 receives, from the CCU 5039, a control signal for controlling the driving of the camera head 5005. The control signal includes information regarding an imaging condition such as, for example, information for designating a frame rate of a captured image, information for designating an exposure value in image capturing, and/or information for designating a magnification and a focal point of a captured image. The communication unit 5013 provides the received control signal to the camera head control unit 5015. Note that a control signal from the CCU 5039 may also be transmitted by optical communication. In this case, the communication unit 5013 is provided with a photoelectric conversion module for photoelectrically converting an optical signal into an electrical signal, and a control signal is provided to the camera head control unit 5015 after being converting into an electrical signal by the photoelectric conversion module.

Note that the above-described imaging conditions such as a frame rate, an exposure value, a magnification, and a focal point are automatically set by the control unit 5063 of the CCU 5039 on the basis of the acquired image signal. That is, the endoscope 5001 is equipped with a so-called auto exposure (AE) function, an auto focus (AF) function, and an auto white balance (AWB) function.

The camera head control unit 5015 controls the driving of the camera head 5005 on the basis of the control signal received from the CCU 5039 via the communication unit 5013. For example, the camera head control unit 5015 controls the driving of the image sensor of the imaging unit 5009 on the basis of information for designating a frame rate of a captured image and/or information for designating exposure in image capturing. Furthermore, for example, the camera head control unit 5015 appropriately moves the zoom lens and the focus lens of the lens unit 5007 via the driving unit 5011 on the basis of information for designating a magnification and a focal point of a captured image. Moreover, the camera head control unit 5015 may have a function of storing information for identifying the lens barrel 5003 or the camera head 5005.

Note that, by disposing configurations such as the lens unit 5007 or the imaging unit 5009, into a sealed structure with high airtightness and a waterproof property, the camera head 5005 can have a resistance characteristic to autoclave sterilization processing.

Next, a functional configuration of the CCU 5039 will be described. The communication unit 5059 includes a communication device for exchanging various types of information with the camera head 5005. The communication unit 5059 receives an image signal transmitted from the camera head 5005 via the transmission cable 5065. At this time, as described above, the image signal can be preferably transmitted by optical communication. In this case, for performing optical communication, the communication unit 5059 is provided with a photoelectric conversion module for converting an optical signal into an electrical signal. The communication unit 5059 provides the image signal converted into the electrical signal, to the image processing unit 5061.

Furthermore, the communication unit 5059 transmits, to the camera head 5005, a control signal for controlling the driving of the camera head 5005. The control signal may be transmitted by optical communication.

The image processing unit 5061 performs various types of image processing on the image signal being RAW data that have been transmitted from the camera head 5005. The image processing includes various types of known signal processing such as, for example, development processing, high image quality processing (band enhancement processing, super-resolution processing, noise reduction (NR) processing, image stabilization processing, and/or the like), and/or enlargement processing (electronic zoom processing). Furthermore, the image processing unit 5061 performs detection processing of an image signal for performing AE, AF, and AWB.

The image processing unit 5061 includes a processor such as a CPU or a GPU, and the aforementioned image processing and detection processing can be performed by the processor operating in accordance with a predetermined program. Note that, in a case where the image processing unit 5061 includes a plurality of GPUs, the image processing unit 5061 appropriately divides information regarding an image signal, and concurrently performs image processing using the plurality of GPUs.

The control unit 5063 performs various types of control regarding image capturing of an operative portion that is performed by the endoscope 5001, and display of the captured image. For example, the control unit 5063 generates a control signal for controlling the driving of the camera head 5005. At this time, in a case where an imaging condition is input by the user, the control unit 5063 generates a control signal on the basis of the input performed by the user. Alternatively, in a case where the endoscope 5001 is equipped with the AE function, the AF function, and the AWB function, the control unit 5063 appropriately calculates an optimum exposure value, focal length, and white balance in accordance with a result of detection processing performed by the image processing unit 5061, and generates a control signal.

Furthermore, the control unit 5063 causes an image of an operative portion to be displayed on the display device 5041 on the basis of an image signal having been subjected to the image processing performed by the image processing unit 5061. At this time, the control unit 5063 recognizes various objects in an operative portion image using various image recognition technologies. For example, by detecting an edge shape, color, or the like of an object included in an operative portion image, the control unit 5063 can recognize an operation tool such as forceps, a specific biological body region, bleeding, mist in using the energy treatment tool 5021, or the like. When displaying an image of an operative portion on the display device 5041, the control unit 5063 displays various types of operation support information so as to be superimposed on the image of the operative portion, using the recognition result. By the operation support information being displayed in a superimposed manner, and presented to the operator 5067, it becomes possible to advance an operation more safely and surely.

The transmission cable 5065 connecting the camera head 5005 and the CCU 5039 is an electrical signal cable for performing communication of an electrical signal, an optical fiber for performing optical communication, or a composite cable of these.

Here, in the example illustrated in the drawing, communication is performed in a wired manner using the transmission cable 5065, but communication may be wirelessly performed between the camera head 5005 and the CCU 5039. In a case where communication is wirelessly performed between the camera head 5005 and the CCU 5039, because the transmission cable 5065 needs not be laid in a room, a situation in which the movement of a medical staff in an operating room is disturbed by the transmission cable 5065 can be solved.

Heretofore, an example of the endoscopic operation system 5000 to which the medical support arm device according to the present disclosure can be applied has been described. Note that, here, the endoscopic operation system 5000 has been described as an example, but a system to which the technology according to the present disclosure can be applied is not limited to this example. For example, the medical support arm device according to the present disclosure may be applied to a checkup flexible endoscope system or a micrographic operation system.

In this manner, in the present embodiment, in the medical field, it is proposed to perform an operation while capturing an image of an operative region using the support arm device 5027. Here, in various practices including operations, it is required to reduce fatigue and burden of the operator 5067 and the patient 5071 by performing practices more efficiently. For satisfying such a request, the support arm device 5027 is considered to be required to have the following performance, for example.

First, as a first point, the support arm device 5027 is required to secure a work space in an operation. While the operator 5067 is performing various types of treatment on the patient 5071, if the arm portion 5031 or the endoscope 5001 disturbs a field of view of a practitioner or disturbs a motion of a hand performing the treatment, this leads to a decline in efficiency of the operation. Furthermore, in an actual operation site, it is general that a plurality of other doctors, nurses, and the like for performing various support works such as handover of a tool to the user or checking of various vital signs of the patient 5071 exist around the user and the patient 5071, which is not illustrated in FIG. 1. Furthermore, because the other devices and the like for performing the support works exist, an operation environment is complicated. Accordingly, it is desirable that the support arm device 5027 is more compact.

Subsequently, as a second point, the support arm device 5027 is required to have high operability in moving the endoscope 5001. For example, depending on a region in which an operation is performed or content of an operation, the user desires to observe the same operative region from various positions or angles while performing treatment on the operative region. For changing an angle in which an operative region is observed, it is necessary to change an angle of the endoscope 5001 with respect to the operative region, but at this time, it is more desirable that only an imaging angle is changed with an imaging direction of the endoscope 5001 being fixed to the operative region (in other words, while imaging the same region). Accordingly, for example, the support arm device 5027 has been required to have operability with a higher degree of freedom in such a manner that, in a state in which an imaging direction of the endoscope 5001 is fixed to the operative region, the endoscope 5001 moves within a surface of a circular cone having a vertex corresponding to the operative region, like a turning operation (pivot operation) around an axis of the circular cone serving as a turning axis. Note that, because an imaging direction of the endoscope 5001 is fixed to a predetermined operative region, the pivot operation is also called a point lock operation.

Furthermore, for changing a position and an angle of the endoscope 5001, for example, a conceivable method is a method of moving the endoscope 5001 to a desired position and angle by the user manually moving the arm portion 5031. Accordingly, it is desirable that operability that enables the movement of the endoscope 5001, the aforementioned pivot operation, or the like to be easily performed in one hand, for example, is provided.

Furthermore, in an operation, for example, the following request is considered. More specifically, while performing treatment with both hands, the user desires to move an imaging center of a captured image to be captured by the endoscope 5001, from a region in which treatment is being performed, to another region (for example, a region in which the next treatment is to be performed). Accordingly, in changing a position and orientation of the endoscope 5001, there are required various driving methods of the arm portion 5031 including not only the aforementioned method of manually controlling the driving of the arm portion 5031, but also a method of controlling the driving of the arm portion 5031 in accordance with an operation input from an input unit such as a pedal, for example.

In this manner, as the second performance, the support arm device 5027 is required to have higher operability that follows the intuition and demand of the user, and implements the aforementioned pivot operation and a manual easy movement, for example.

Lastly, as a third point, the support arm device 5027 is required to have stability in the driving control of the arm portion 5031. The stability in the driving control of the arm portion 5031 may be stability in position and orientation of a distal end unit in driving the arm portion 5031. Furthermore, the stability in the driving control of the arm portion 5031 also includes a smooth movement and vibration suppression (vibration deadening) of the distal end unit in driving the arm portion 5031. For example, as in the example illustrated in FIG. 1, in a case where the distal end unit is the endoscope 5001, if the position or orientation of the endoscope 5001 is unstable, a captured image displayed on a display screen of the display device 5041 becomes unstable, and discomfort feeling is inevitably given to the user. In particular, when the support arm device 5027 is used in an operation, in a conceivable usage method, a stereo camera including two imaging units (camera units) as a distal end is provided, and a three-dimensional image (3D image) generated on the basis of an image captured by the stereo camera is displayed on the display device 5041. In a case where a 3D image is displayed in this manner, if the position or orientation of the stereo camera is unstable, there is a possibility that so-called 3D sickness of the user is induced. Furthermore, depending on a region in which an operation is performed or content of an operation, an observation range in which an image is captured by the endoscope 5001 is sometimes enlarged to about $\varphi 15$ mm. In this manner, in a case where the endoscope 5001 captures an image of a narrow range in an enlarged manner, little vibration of the endoscope 5001 appears as large vibration or blurring of a captured image. Accordingly, the driving control of the arm portion 5031 and the endoscope 5001 is required to have high positioning accuracy with an allowable range of about 1 mm. In this manner, the driving control of the arm portion 5031 is required to have high-accuracy responsivity and high positioning accuracy.

The present inventors have considered an existing general balance-type arm and a positioning control-based support arm device from the viewpoints of the above-described three types of performance.

First, regarding the securing of a work space of an operation as described in the first point, in a general balance-type arm, because a counter balance weight (also called counter weight or balancer) for controlling power balance in moving an arm portion is normally provided inside a base portion or the like, it is difficult to reduce the size of the balance-type arm, and it is hard to say that the performance is satisfied.

Furthermore, regarding high operability as described in the second point, in the general balance-type arm, only a part of the driving of the arm portion such as, for example, only the driving of two axes for moving an imaging unit on a plane (two-dimensional plane) is electrical driving, and manual positioning is required for moving the arm portion and the imaging unit. It is therefore hard to say that high operability can be realized. Furthermore, in a general positioning control-based support arm device, it is difficult for the positioning control used in the driving control of an arm portion, in other words, in the control of a position and orientation of an imaging unit, to flexibly respond to external force. Thus, such positioning control is commonly called "rigid control", and is not suitable for implementing operability that follows the intuition of the user as requested.

Furthermore, regarding the stability in the driving control of an arm portion as described in the third point, generally, in a joint portion of an arm portion, a factor being difficult to be modeled, such as friction and inertia, exists. In the general balance-type arm or the positioning control-based support arm device, if these factors appear as disturbance in the driving control of the joint portion, even in a case where a theoretically-appropriate control value (for example, a value of current to be applied to a motor of the joint portion) is applied, desired driving (for example, rotation at a desired angle in the motor of the joint portion) sometimes fails to be implemented, and it is difficult to implement high stability in the driving control of the arm portion as requested.

As described above, as a result of considering a support arm device used for medical purposes, the present inventors have obtained such perceptions that requests for the aforementioned three types of performance exist regarding the support arm device. However, in the existing general balance-type arm and the positioning control-based support arm device, it is considered that it is difficult to satisfy these types of performance. As a result of considering a configuration of satisfying the aforementioned three types of performance, the present inventors have conceived a support arm device according to the present disclosure, a control device of a support arm, a control system (also called medical system) of a support arm, a support arm control method, and a program. Hereinafter, a preferable embodiment of the configuration conceived by the present inventors will be described in detail.

2. Embodiment of Present Disclosure

Hereinafter, a support arm control system according to an embodiment of the present disclosure will be described. In the support arm control system according to the present embodiment, the driving of a plurality of joint portions provided in a support arm device is controlled by total body harmonized control that uses generalized inverse dynamics. Moreover, ideal joint control of implementing an ideal response to a command value by correcting the influence of disturbance is applied to the driving control of the joint portion.

In the following description of the present embodiment, first, in <<2-1. External appearance of support arm device>>, an external appearance of the support arm device according to the present embodiment is illustrated, and a schematic configuration of the support arm device will be described. Subsequently, in <<2-2. Generalized inverse dynamics>> and <<2-3. Ideal joint control>>, overviews of generalized inverse dynamics and ideal joint control used in the control of the support arm device according to the present embodiment will be described. Subsequently, in <<2-4. Configuration of support arm control system>>, a configuration of a system for controlling the support arm device according to the present embodiment will be described using a functional block diagram.

Note that, in the following description, as an embodiment of the present disclosure, a case where a distal end unit of an arm portion of the support arm device is an imaging unit (endoscope device), and an image of an operative region is captured by the imaging unit in an operation as illustrated in FIG. 1 will be described, but the present embodiment is not limited to this example. The support arm control system according to the present embodiment can be applied in a case where a support arm device including another distal end unit is used for another use application.

<<2-1. External Appearance of Support Arm Device>>

Figure 3:
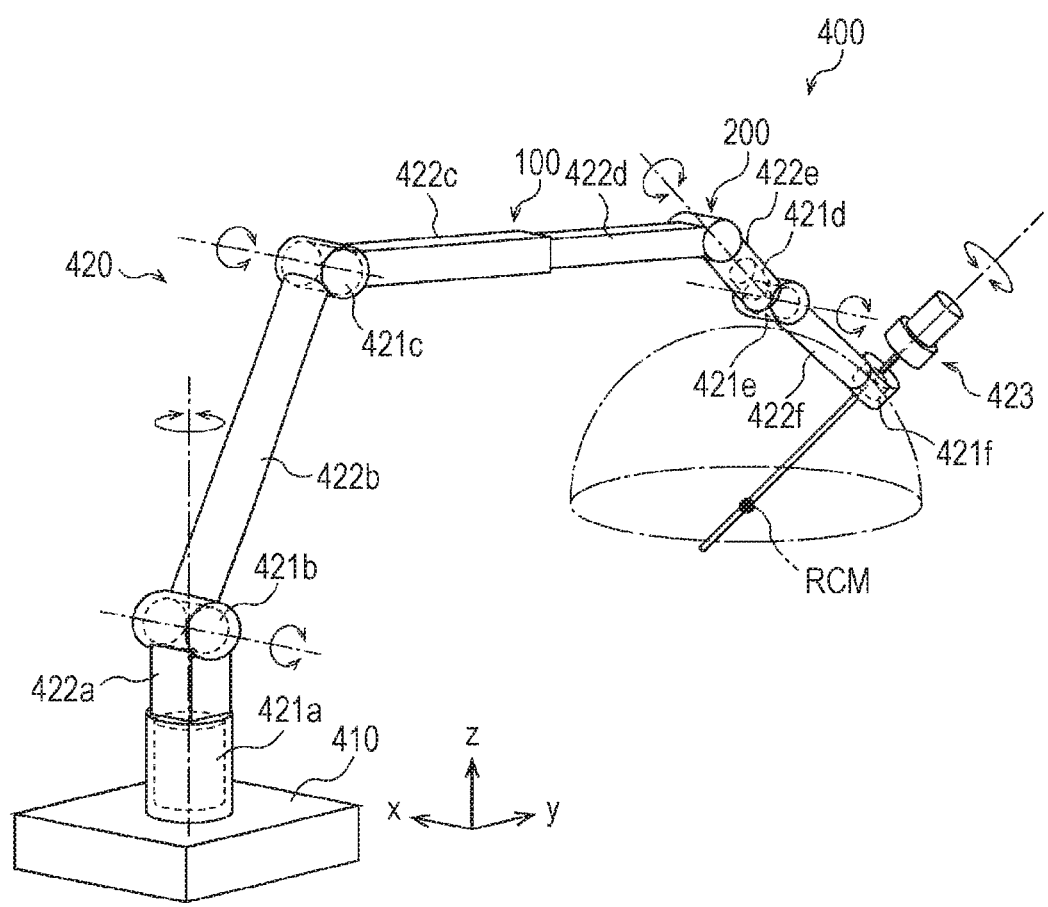
FIG. 3 is a perspective view illustrating a configuration example of a medical support arm device according to an embodiment of the present disclosure.

First, a schematic configuration of a support arm device 400 according to the present embodiment will be described with reference to FIG. 3. FIG. 3 is a schematic diagram illustrating an external appearance of the support arm device 400 according to the present embodiment.

The support arm device 400 according to the present embodiment includes a base portion 410 and an arm portion 420. The base portion 410 is a base of the support arm device 400, and the arm portion 420 extends from the base portion 410. Furthermore, a control unit for comprehensively controlling the support arm device 400, which is not illustrated in FIG. 3, may be provided in the base portion 410, and the driving of the arm portion 420 may be controlled by the control unit. The control unit includes various signal processing circuits such as a CPU or a DSP, for example.

The arm portion 420 includes a plurality of the active joint portions 421a to 421f (hereinafter, active joint portions will be sometimes simply described as joint portions), a plurality of links 422a to 422f, and an endoscope device 423 serving as a distal end unit provided at the distal end of the arm portion 420.

The links 422a to 422f are members having a substantially stick shape. One end of the link 422a is coupled with the base portion 410 via the active joint portion 421a, another end of the link 422a is coupled with one end of the link 422b via the active joint portion 421b. Moreover, another end of the link 422b is coupled with one end of the link 422c via the active joint portion 421c. Another end of the link 422c is coupled with the link 422d via a passive slide mechanism 100. Moreover, another end of the link 422d is coupled with one end of the link 422e via a passive joint portion 200. Another end of the link 422e is coupled with one end of the link 422f via the active joint portions 421d and 421e. The endoscope device 423 is coupled to a distal end of the arm portion 420, in other words, another end of the link 422f via the active joint portion 421f. In this manner, with the base portion 410 functioning as a fulcrum point, the ends of the plurality of links 422a to 422f are coupled to each other by the active joint portions 421a to 421f, the passive slide mechanism 100, and the passive joint portion 200. An arm shape extending from the base portion 410 is thereby formed.

By the driving of actuators provided in the respective active joint portions 421a to 421f of the arm portion 420 being controlled, the position and orientation of the endoscope device 423 are controlled. In the present embodiment, the distal end of the endoscope device 423 enters the body cavity of a patient being an operative region, and the endoscope device 423 captures an image of a partial region of the operative region. However, the distal end unit provided at the distal end of the arm portion 420 is not limited to the endoscope device 423, and various medical tools may be connected to the distal end of the arm portion 420 as a distal end unit. In this manner, the support arm device 400 according to the present embodiment is formed as a medical support arm device including a medical tool.

Here, coordinate axes are defined as illustrated in FIG. 3, and the support arm device 400 will be hereinafter described. Furthermore, in accordance with the coordinate axes, an up-down direction, a front-back direction, and a left-right direction are defined. In other words, an up-down direction with respect to the base portion 410 installed on a floor surface is defined as a z-axis direction and the up-down direction. Furthermore, a direction which is mutually orthogonal to the z-axis direction, and in which the arm portion 420 extends from the base portion 410 (in other words, a direction in which the endoscope device 423 is positioned with respect to the base portion 410) is defined as a y-axis direction and the front-back direction. Moreover, a direction mutually orthogonal to the y-axis and the z-axis is defined as an x-axis direction and the left-right direction.

The active joint portions 421a to 421f rotatably couple the links to one another. The active joint portions 421a to 421f include actuators, and include rotation mechanisms rotationally driven with respect to a predetermined rotation axis by the driving of the actuators. By controlling the rotational driving of each of the active joint portions 421a to 421f, for example, it is possible to control the driving of the arm portion 420 such as extending or contracting (folding) the arm portion 420. Here, the driving of the active joint portions 421a to 421f can be controlled by known the total body harmonized control and the ideal joint control, for example. As mentioned above, because the active joint portions 421a to 421f include the rotation mechanisms, in the following description, the driving control of the active joint portions 421a to 421f specifically means the control of a rotational angle and/or generated torque of the active joint portions 421a to 421f (torque generated by the active joint portions 421a to 421f).

The passive slide mechanism 100 is one mode of a passive form change mechanism, and couples the link 422c and the link 422d to each other so as to be movable forward and backward along a predetermined direction. For example, the passive slide mechanism 100 may couple the link 422c and the link 422d to each other so as to be movable straight. However, forward and backward movements of the link 422c and the link 422d are not limited to straight movements, and may be forward and backward movements in a direction forming an arc shape. Operations of forward and backward movements are performed by the user, for example, and the passive slide mechanism 100 makes a distance between the active joint portion 421c on the one end side of the link 422c and the passive joint portion 200 variable. The entire form of the arm portion 420 can thereby change. The details of the configuration of the passive slide mechanism 100 will be described later.

The passive joint portion 200 is one mode of a passive form change mechanism, and rotatably couples the link 422d and the link 422e to each other. A rotational operation is performed by the user, for example, and the passive joint portion 200 makes an angle formed by the link 422d and the link 422e, variable. The entire form of the arm portion 420 can thereby change. The details of the configuration of the passive joint portion 200 will be described later.

Note that, in this specification, "the orientation of the arm portion" refers to a state of the arm portion that can be changed by the driving control of the actuators provided in the active joint portions 421a to 421f that is performed by the control unit in a state in which a distance between adjacent active joint portions across one or a plurality of links is fixed. Furthermore, "the form of the arm portion" refers to a state of the arm portion that can be changed by a change in distance between adjacent active joint portions across a link, or a change in angle formed by links connecting the adjacent active joint portions that is caused in accordance with the operation of the passive form change mechanism.

The support arm device 400 according to the present embodiment includes the six active joint portions 421a to 421f, and a six-degree of freedom regarding the driving of the arm portion 420 is realized. That is, while the driving control of the support arm device 400 is implemented by the driving control of the six active joint portions 421a to 421f that is performed by the control unit, the passive slide mechanism 100 and the passive joint portion 200 are not subjected to driving control performed by the control unit.

Specifically, as illustrated in FIG. 3, the active joint portions 421a, 421d, and 421f are provided in such a manner that a long axis direction of each of the connected links 422a and 422e, and an imaging direction of the connected endoscope device 423 correspond to a rotation axis direction. The active joint portions 421b, 421c, and 421e are provided in such a manner that the x-axis direction being a direction in which a copulation angle of each of the connected links 422a to 422c, 422e, and 422f, and the endoscope device 423 is changed in a y-z-plane (plane defined by the y-axis and the z-axis) corresponds to a rotation axis direction. In this manner, in the present embodiment, the active joint portions 421a, 421d, and 421f have a function of performing so-called yawing, and the active joint portions 421b, 421c, and 421e have a function of performing so-called pitching.

By having such a configuration of the arm portion 420, in the support arm device 400 according to the present embodiment, a six-degree of freedom is realized with respect to the driving of the arm portion 420. Thus, the endoscope device 423 can be freely moved within a movable range of the arm portion 420. In FIG. 3, as an example of a movable range of the endoscope device 423, a hemisphere is illustrated. If a center point RCM (remote motion center) of the hemisphere is assumed to be an imaging center of an operative region imaged by the endoscope device 423, by moving the endoscope device 423 on the spherical surface of the hemisphere in a state in which the imaging center of the endoscope device 423 is fixed to the center point of the hemisphere, the operative region can be imaged from various angles.

Figure 4:
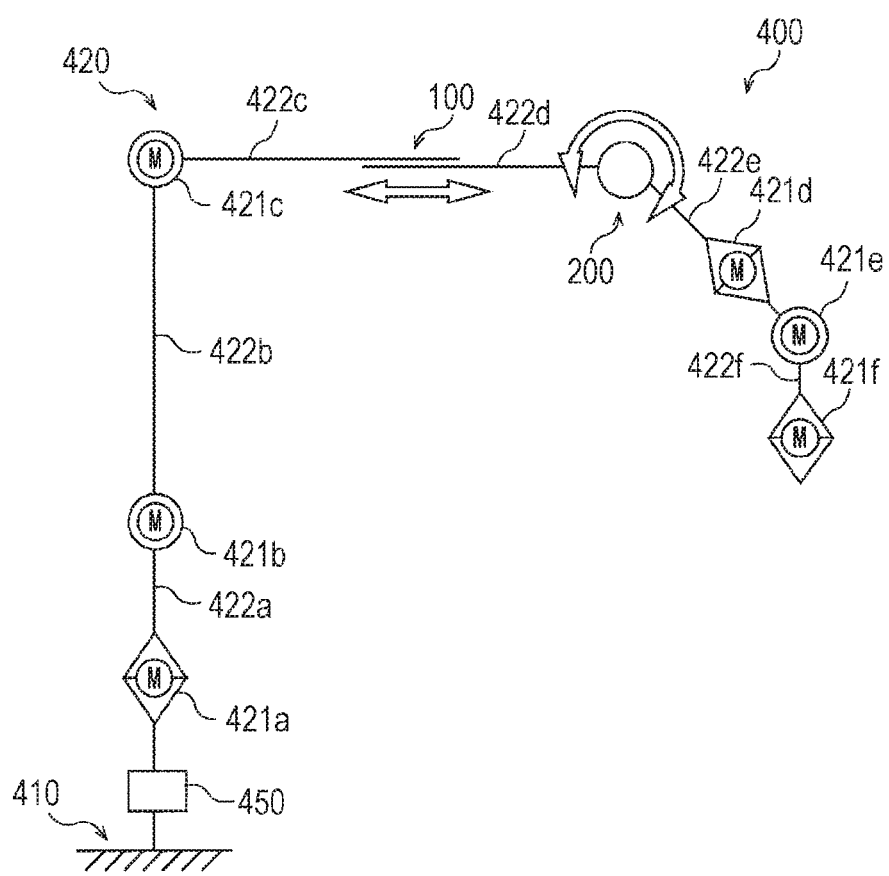
FIG. 4 is an explanatory diagram schematically illustrating the medical support arm device according to the embodiment.

FIG. 4 is a schematic diagram illustrating a configuration of the support arm device 400 according to the present embodiment. The arm portion 420 of the support arm device 400 is coupled to the base portion 410 at the root side, and extends toward the distal end side on which an endoscope device (not illustrated) is supported. The three active joint portions 421d, 421e, and 421f disposed on the distal end side mainly have a function of ensuring operations in a three-degree of freedom of an endoscope device, and changing an imaging direction. Furthermore, the three active joint portions 421a, 421b, and 421c disposed on the root side mainly have a function of changing a position of an endoscope device. That is, in the support arm device 400 according to the present embodiment, by the rotational driving of the active joint portions 421a, 421b, and 421c on the root side, an approximate position of an endoscope device supported on the distal end side is decided, and an imaging direction of the endoscope device is decided by the rotational driving of the active joint portions 421d, 421e, and 421f on the distal end side.

Furthermore, an orientation sensor 450 for detecting inclination in a horizontal direction of the entire arm portion 420 may be provided at a root portion of the arm portion 420 of the support arm device 400 such as, for example, a coupled portion of the link 422a and the base portion 410. The inclination of the entire arm portion 420 that is detected by the orientation sensor 450 is used in the calculation of gravity acting on the arm portion 420, and the control unit can execute control for cancelling gravity (hereinafter, also be referred to as "gravity compensation control"), using the calculated gravity. As the orientation sensor 450, for example, a sensor that uses at least one of a gyro sensor or an acceleration sensor can be applied.

The passive slide mechanism 100 and the passive joint portion 200 that serve as passive form change mechanisms are provided between the active joint portion 421c and the active joint portion 421d. That is, the passive form change mechanisms are disposed closer to the root side than the at least three active joint portions 421d to 421f disposed on the distal end side of the arm portion 420. For this reason, the passive slide mechanism 100 and the passive joint portion 200 can change a movable range of the arm portion 420 without applying large influence on the control of an imaging direction of an endoscope device that is performed by the three active joint portions 421d to 421f on the distal end side. However, the arrangement position of the passive form change mechanism is not limited to the above-described example. Even if the passive form change mechanism is disposed at any position, the form of the arm portion 420 can be changed.

Here, in a case where a passive form change mechanism is not provided, if a degree of freedom (the number of active joint portions) of the arm portion 420 or a length of each link of the arm portion 420 is designed in accordance with an expected largest movable range of the endoscope device, in an operative procedure requiring a small degree of freedom or movable range, the arm portion 420 becomes too big. This can consequently lead to interference to a viewing field or a working space of an operator, or interference to the arrangement of another device in an operating room. Furthermore, if a degree of freedom of the arm portion 420 increases, the number of actuators also increases, and this can lead to an increase in cost or weight of the arm portion 420. Moreover, by elongating the length of each link, required output of the actuator provided in the active joint portion 421a on the root side increases, and this can lead to an increase in cost.

In contrast to this, by including the passive slide mechanism 100 and the passive joint portion 200, the support arm device 400 according to the present embodiment can change a distance between a part of active joint portions of the arm portion 420, and at least one of angles of a part of links. For this reason, the support arm device 400 can secure an appropriate movable range by changing the form of the arm portion 420 in accordance with a purpose or content of an operative procedure. Thus, it is possible to prevent a viewing field or a working space of an operator from being disturbed more than necessary, or prevent the arrangement of another device in an operating room from being disturbed more than necessary. Furthermore, the support arm device 400 can suppress an increase in cost because the support arm device 400 can secure an appropriate movable range without increasing a degree of freedom (the number of active joint portions) more than necessary.

Here, the configuration of the joint portions 421a to 421f illustrated in FIG. 3 will be described in more detail with reference to FIG. 5. Note that, here, the configuration of the actuator, which is a configuration mainly related to the rotational driving of the joint portions 421a to 421f, among the configurations of the joint portions 421a to 421f, will be described with reference to FIG. 5.

Figure 5:
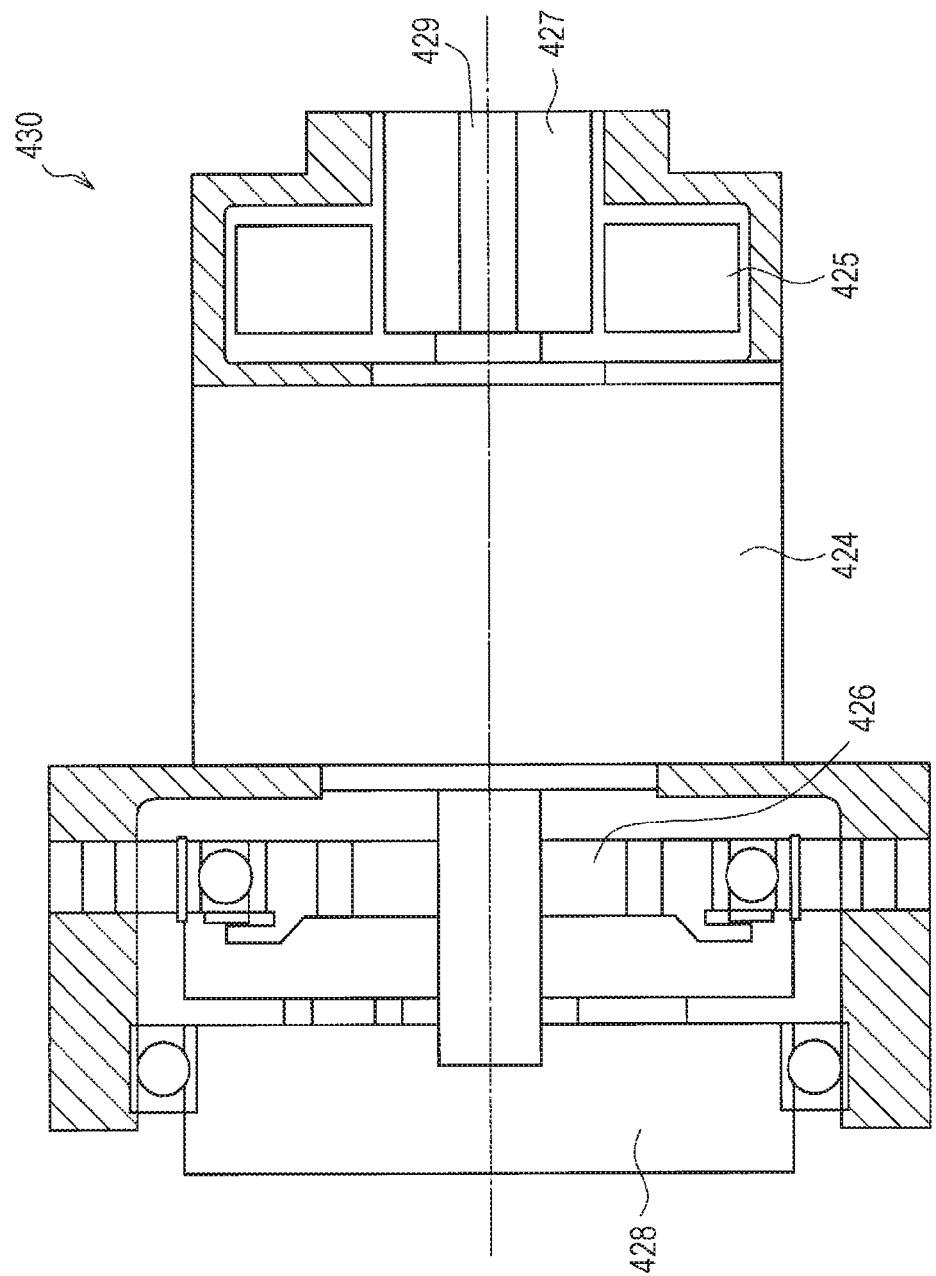
FIG. 5 is a cross-sectional diagram schematically illustrating a state in which an actuator of a joint portion according to an embodiment of the present disclosure is cut along a cross-section passing through a rotation axis.

FIG. 5 is a cross-sectional diagram schematically illustrating a state in which an actuator of any of the joint portions 421a to 421f according to an embodiment of the present disclosure is cut along a cross-section passing through a rotation axis. Note that, in FIG. 5, among the configurations of the joint portions 421a to 421f, only the actuator is illustrated, but the joint portions 421a to 421f may include another configuration. For example, aside from the configurations illustrated in FIG. 5, the joint portions 421a to 421f include various configurations necessary for the driving of the arm portion 420, such as a control unit for controlling the driving of the actuator, and a support member for connecting and supporting the links 422a to 422c and the endoscope device 423. Note that, in the above description and the following description, the driving of a joint portion of an arm portion may mean the driving of an actuator in a joint portion.

Note that, as mentioned above, in the present embodiment, the driving of the joint portions 421a to 421f is controlled by ideal joint control as described later in the following <<2-3. Ideal joint control>>. Accordingly, the actuators of the joint portions 421a to 421f illustrated in FIG. 5 are configured to perform driving corresponding to ideal joint control. Specifically, the actuators of the joint portions 421a to 421f are configured to adjust a rotational angle in the joint portions 421a to 421f and torque generated in accordance with rotational driving. Furthermore, the actuators of the joint portions 421a to 421f are configured to arbitrarily adjust viscous resistance coefficients for a rotational movement, and can realize, for example, a state in which rotation is easily performed by force added from the outside (in other words, it is easy to manually move the arm portion 420) or a state in which it is difficult to perform rotation (in other words, it is difficult to manually move the arm portion 420).

Referring to FIG. 5, an actuator 430 of the joint portions 421a to 421f according to the present includes a motor 424, a motor driver 425, a reduction gear 426, an encoder 427, a torque sensor 428, and a drive shaft 429. As illustrated in FIG. 5, the encoder 427, the motor 424, the reduction gear 426, and the torque sensor 428 are coupled to the drive shaft 429 in series in this order.

The motor 424 is a power engine in the actuator 430, and rotates the drive shaft 429 around an axis thereof. For example, the motor 424 is an electrical motor such as a brushless DC motor. In the present embodiment, the rotational driving of the motor 424 is controlled by current being supplied.

The motor driver 425 is a driver circuit (driver integrated circuit (IC)) that rotationally drives the motor 424 by supplying current to the motor 424, and can control the number of rotations of the motor 424 by adjusting an amount of current to be supplied to the motor 424. Furthermore, by adjusting an amount of current to be supplied to the motor 424, the motor driver 425 can adjust a viscous resistance coefficient for the aforementioned rotational movement of the actuator 430.

The reduction gear 426 is connected to the drive shaft 429, and generates rotational drive force (in other words, torque) having a predetermined value, by decelerating a rotational speed of the drive shaft 429 that is generated by the motor 424, at a predetermined reduction ratio. As the reduction gear 426, a backlashless-type high performance reduction gear is used. For example, the reduction gear 426 may be a Harmonic Drive (registered trademark). The torque generated by the reduction gear 426 is transmitted, via the torque sensor 428 connected to an output shaft of the reduction gear 426, to an output member (not illustrated. For example, a coupling member of the links 422a to 422c, the endoscope device 423, or the like) on a subsequent stage.

The encoder 427 is connected to the drive shaft 429, and detects the number of rotations of the drive shaft 429. On the basis of a relationship between the number of rotations of the drive shaft 429 that has been detected by the encoder, and the reduction ratio of the reduction gear 426, it is possible to obtain information regarding a rotational angle, a rotational angular speed, a rotational angular acceleration, and the like of the joint portions 421a to 421f.

The torque sensor 428 is connected to the output shaft of the reduction gear 426, and detects torque generated by the reduction gear 426, in other words, torque output by the actuator 430. In the following description, torque output by the actuator 430 will also be simply called generated torque.

In this manner, in the actuator 430, by adjusting an amount of current to be supplied to the motor 424, it is possible to adjust the number of rotations of the motor 424. Here, the reduction ratio used by the reduction gear 426 may be appropriately settable in accordance with use application of the support arm device 400. Accordingly, by appropriately adjusting the number of rotations of the motor 424 in accordance with the reduction ratio used by the reduction gear 426, it is possible to control generated torque. Furthermore, in the actuator 430, on the basis of the number of rotations of the drive shaft 429 that has been detected by the encoder 427, it is possible to obtain information regarding a rotational angle, a rotational angular speed, a rotational angular acceleration, and the like of the joint portions 421a to 421f, and generated torque in the joint portions 421a to 421f can be detected by the torque sensor 428.

Furthermore, the torque sensor 428 can detect not only generated torque generated by the actuator 430, but also external torque added from the outside. Accordingly, by adjusting an amount of current to be supplied to the motor 424 by the motor driver 425, on the basis of the external torque detected by the torque sensor 428, it is possible to adjust a viscous resistance coefficient for the aforementioned rotational movement, and it is possible to realize a state in which rotation is easily performed by force added from the outside or a state in which it is difficult to perform rotation, for example.

Figure 6A:
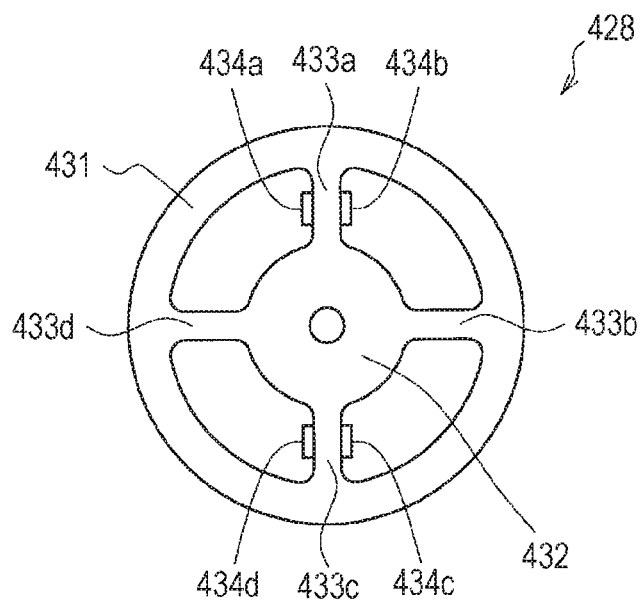
FIG. 6A is a schematic diagram schematically illustrating a state in which a torque sensor illustrated in FIG. 3 is viewed in an axial direction of a drive shaft.

Here, a configuration of the torque sensor 428 will be described in detail with reference to FIGS. 6A and 6B. FIG. 6A is a schematic diagram schematically illustrating a state in which the torque sensor 428 illustrated in FIG. 5 is viewed in an axial direction of the drive shaft 429.

Referring to FIG. 6A, the torque sensor 428 includes an outer ring portion 431, an inner ring portion 432, beam portions 433a to 433d, and deformation detection elements 434a to 434d. As illustrated in FIG. 6A, the outer ring portion 431 and the inner ring portion 432 are concentrically disposed. In the present embodiment, the inner ring portion 432 is connected with an input side, in other words, an output shaft from the reduction gear 426, and the outer ring portion 431 is connected with an output side, in other words, an output member (not illustrated) of a subsequent stage.

The four beam portions 433a to 433d are provided between the outer ring portion 431 and the inner ring portion 432 that are concentrically disposed, and connect the outer ring portion 431 and the inner ring portion 432 to each other. As illustrated in FIG. 6A, the beam portions 433a to 433d are interposed between the outer ring portion 431 and the inner ring portion 432 in such a manner that the adjacent beam portions 433a to 433d form an angle of 90 degrees.

Among the beam portions 433a to 433d, two beam portions facing each other, in other words, two beam portions provided at an angle of 180 degrees are provided with the deformation detection elements 434a to 434d. On the basis of an amount of deformation of the beam portions 433a to 433d that has been detected by the deformation detection elements 434a to 434d, it is possible to detect generated torque of the actuator 430 and external torque.

In the example illustrated in FIG. 6A, among the beam portions 433a to 433d, the deformation detection elements 434a and 434b are provided on the beam portion 433a, and the deformation detection elements 434c and 434d are provided on the beam portion 433c. Furthermore, the deformation detection elements 434a and 434b are provided so as to sandwich the beam portion 433a, and the deformation detection elements 434c and 434d are provided so as to sandwich the beam portion 433c. For example, the deformation detection elements 434a to 434d are strain gauges, and detect a geometric deformation amount of the beam portions 433a and 433c on the basis of a change in electrical resistance, by being attached to the surface of the beam portions 433a and 433c. By the deformation detection elements 434a to 434d being provided at four points as illustrated in FIG. 6A, the detection elements 434a to 434d form a so-called Wheatstone bridge. Accordingly, because it is possible to detect deformation using a so-called four-gauge method, it is possible to reduce influence such as interference of another shaft other than a shaft from which deformation is to be detected, decentering of the drive shaft 429, or temperature drift.

In this manner, the beam portions 433a to 433d serve as flexure elements for detecting deformation. Note that the type of the deformation detection elements 434a to 434d according to the present embodiment is not limited to a strain gauge, and other elements may be used. For example, the deformation detection elements 434a to 434d may be elements that detect a deformation amount of the beam portions 433a to 433d on the basis of a change in magnetic characteristic.

Furthermore, the following configurations, which are not illustrated in FIGS. 5 and 6A, may be applied for enhancing detection accuracy of generated torque and external torque to be detected by the torque sensor 428. For example, because support moment is released by thinning regions of the beam portions 433a to 433d that are to be connected with the outer ring portion 431, to be thinner than the other regions, linearity of a detected deformation amount is enhanced, and influence caused by radial load is reduced. Furthermore, by supporting the outer ring portion 431 and the inner ring portion 432 together by a housing via a bearing, it is possible to exclude the action of another axial force from both of the input shaft and the output shaft, and moment. Furthermore, for reducing another axial moment acting on the outer ring portion 431, a double-supported bearing for support may be provided at another end of the actuator 430 illustrated in FIG. 5, in other words, in a region in which the encoder 427 is provided.

Heretofore, the configuration of the torque sensor 428 has been described with reference to FIG. 6A. As described above, by the configuration of the torque sensor 428 illustrated in FIG. 6A, it becomes possible to perform accurate detection in the detection of generated torque of the actuator 430 and external torque.

Here, in the present embodiment, the configuration of the torque sensor 428 is not limited to the configuration illustrated in FIG. 6A, and may be another configuration. Other than the torque sensor 428, an example of another configuration of a torque sensor applied to the actuator 430 will be described with reference to FIG. 6B.

Figure 6B:
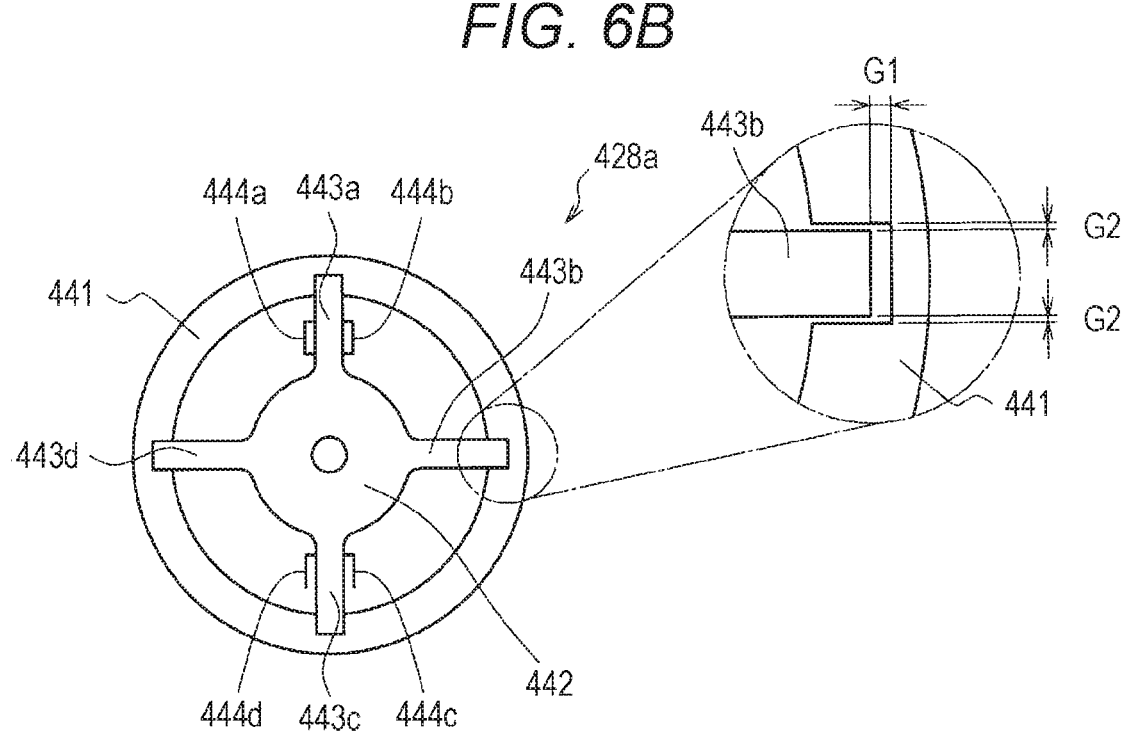
FIG. 6B is a schematic diagram illustrating another configuration example of a torque sensor applied to the actuator illustrated in FIG. 3.

FIG. 6B is a schematic diagram illustrating another configuration example of a torque sensor applied to the actuator 430 illustrated in FIG. 5. Referring to FIG. 6B, a torque sensor 428a according to this modified example includes an outer ring portion 441, an inner ring portion 442, beam portions 443a to 443d, and deformation detection elements 444a to 444d. Note that, similarly to FIG. 6A, FIG. 6B schematically illustrates a state in which the torque sensor 428a is viewed in an axial direction of the drive shaft 429.

In the torque sensor 428a, the functions and configurations of the outer ring portion 441, the inner ring portion 442, the beam portions 443a to 443d, and the deformation detection elements 444a to 444d are substantially similar to the functions and configurations of the outer ring portion 431, the inner ring portion 432, the beam portions 433a to 433d, and the deformation detection elements 434a to 434d of the torque sensor 428 that have been described with reference to FIG. 6A. The torque sensor 428a according to this modified example differs in the configuration of connection portions of the beam portions 443a to 443d and the outer ring portion 441. Accordingly, regarding the torque sensor 428a illustrated in FIG. 6B, the configuration of connection portions of the beam portions 443a to 443d and the outer ring portion 441, which is a difference from the torque sensor 428 illustrated in FIG. 6A, will be mainly described, and the description of redundant configurations will be omitted.

Referring to FIG. 6B, together with the overall view of the torque sensor 428a, a connection portion of the beam portion 443b and the outer ring portion 441 is illustrated in an enlarged manner. Note that, in FIG. 6B, only the connection portion of the beam portion 443b and the outer ring portion 441, which is one connection portion among four connection portions of the beam portions 443a to 443d and the outer ring portion 441, is illustrated in an enlarged manner, but the other three connection portion of the beam portions 443a, 443c, and 443d, and the outer ring portion 441 also have a similar configuration.

Referring to the enlarged view in FIG. 6B, in the connection portion of the beam portion 443b and the outer ring portion 441, the outer ring portion 441 is provided with an engagement recess portion, and by the distal end of the beam portion 443b being engaged with the engagement recess portion, the connection portion of the beam portion 443b and the outer ring portion 441 are connected. Furthermore, gaps G1 and G2 are provided between the beam portion 443b and the outer ring portion 441. The gap G1 represents a gap therebetween in a direction in which the beam portion 443b extends toward the outer ring portion 441, and the gap G2 represents a gap therebetween in a direction orthogonal to the direction.

In this manner, in the torque sensor 428a, the beam portions 443a to 443d and the outer ring portion 441 are provided with being separated by the predetermined gaps G1 and G2. In other words, in the torque sensor 428a, the outer ring portion 441 and the inner ring portion 442 are separated. Accordingly, because the inner ring portion 442 is not held on the outer ring portion 441 and has a degree of freedom of motions, if vibration is caused in the driving of the actuator 430, for example, it is possible to absorb deformation components caused by the vibration, by the gaps G1 and G2 between the inner ring portion 442 and the outer ring portion 441. Thus, by applying the torque sensor 428a as a torque sensor of the actuator 430, more accurate detection of generated torque and external torque is implemented.

Note that, regarding the configuration of the actuator 430 for performing ideal joint control as illustrated in FIGS. 5, 6A, and 6B, it is possible to refer to JP 2009-269102 A and JP 2011-209099 A, which are prior patent applications filed by the applicant of the subject application, for example.

Heretofore, the schematic configuration of the support arm device 400 according to the present embodiment has been described with reference to FIGS. 3, 4, 5, 6A, and 6B. Next, the total body harmonized control and the ideal joint control for controlling the driving of the arm portion 420 in the support arm device 400 according to the present embodiment, in other words, the driving of the joint portions 421a to 421f will be described.

<<2-2. Generalized Inverse Dynamics>>

Next, the overview of the generalized inverse dynamics used in total body harmonized control of the support arm device 400 in the present embodiment will be described.

The generalized inverse dynamics is basic calculation in total body harmonized control of a multi-link structure in which a plurality of links is coupled by a plurality of joint portions (for example, the arm portion 420 illustrated in FIG. 3 in the present embodiment), and converts exercise purposes regarding various dimensions in various operation spaces, into torque to be generated in the plurality of the joint portions, considering various constraint conditions.

The operation space is an important concept in force control of a robot device. The operation space is a space for describing relationship between force acting on the multi-link structure, and acceleration of the multi-link structure. In performing the driving control of the multi-link structure not by positioning control but by force control, the concept of the operation space is required in a case where a way of contact between the multi-link structure and an environment is used as a constraint condition. The operation space is, for example, a joint space, a Cartesian space, a momentum space, or the like to which the multi-link structure belongs.

The exercise purpose represents a target value in the driving control of the multi-link structure, and represents a target value of, for example, a position, a speed, acceleration, force, impedance, or the like of the multi-link structure that is to be achieved by the driving control.

The constraint condition is a constraint condition regarding a position, a speed, acceleration, force, or the like of the multi-link structure, and is defined in accordance with the shape or the structure of the multi-link structure, a surrounding environment of the multi-link structure, the setting performed by the user, and the like. For example, the constraint condition includes information regarding generated force, priority, the presence or absence of an unactuated joint, vertical reactive force, friction weight, a support polygon, or the like.

In generalized dynamics, for achieving both of stability in numerical calculation and calculation efficiency processable in actual time, a calculation algorithm thereof includes a virtual force decision process (virtual force calculation processing) being a first stage, and a real force conversion process (real force calculation processing) being a second stage. In the virtual force calculation processing being the first stage, virtual force being virtual force acting on the operation space that is necessary for achieving each exercise purpose is decided considering the priority of the exercise purpose and the largest value of the virtual force. In the real force calculation processing being the second stage, virtual force obtained in the above is converted into real force that can be acted on the configuration of the actual multi-link structure, such as external force, considering a constraint regarding an unactuated joint, vertical reactive force, friction weight, a support polygon, or the like. Hereinafter, the virtual force calculation processing and the real force calculation processing will be described in detail. Note that, in the following description of the virtual force calculation processing, the real force calculation processing, and the ideal joint control as described later, for the sake of explanatory convenience, in some cases, the description will be given using, as a specific example, the configuration of the arm portion 420 of the support arm device 400 according to the present embodiment illustrated in FIGS. 3 and 5.

(2-2-1. Virtual Force Calculation Processing)

A vector having a certain physical amount at each joint portion of a multi-link structure is called a generalized variable q (also called a joint value q or joint space q). An operation space x is defined by the following Formula (1) using a temporal differential value and a Jacobian J of the generalized variable q.

[Math. 1]

$$\dot{x} = J\dot{q} \tag{1}$$

In the present embodiment, for example, q denotes a rotational angle in the joint portions 421a to 421f of the arm portion 420. A motion equation regarding the operation space x is described by the following Formula (2).

[Math. 2]

$$\ddot{x} = \Lambda^{-1} f + c \tag{2}$$

Here, f denotes force acting on the operation space x. Furthermore, $\Lambda^{-1}$ is called an operation space inertia inverse matrix and c is called an operation space bias acceleration and are respectively represented by the following Formulae (3) and (4).

[Math. 3]

$$\Lambda^{-1} = J H^{-1} J^T \tag{3}$$

$$c = J H^{-1}(\tau - b) + \dot{J}\dot{q} \tag{4}$$

Note that H is a term representing a joint space inertia matrix, $\tau$ is a term representing joint force corresponding to the joint value q (for example, generated torque in the joint portions 421a to 421f), and b is a term representing gravity, Coriolis force, or centrifugal force.

In the generalized inverse dynamics, it is known that a position regarding the operation space x and an exercise purpose of a speed can be represented as acceleration of the operation space x. At this time, for realizing operation space acceleration being a target value given as an exercise purpose, from the above Formula (1), a virtual force $f_v$ acting on the operation space x can be obtained by solving a kind of linear complementary problem (LCP) as in the following Formula (5)

[Math. 4]

$$w + \ddot{x} = \Lambda^{-1} f_v + c \tag{5}$$

$$\text{s.t.} \begin{cases} ((w_i < 0) \cap (f_{v_i} = U_i)) \cup \\ ((w_i > 0) \cap (f_{v_i} = L_i)) \cup \\ ((w_i = 0) \cap (L_i < f_{v_i} < U_i)) \end{cases}$$

Here, $L_i$ and $U_i$ respectively denote a negative lower limit (including $-\infty$) of an i-th component of $f_v$, and a positive upper limit (including $+\infty$) of the i-th component of $f_v$. The above-described LCP can be solved by using, for example, an iterative method, a pivot method, a method that applies robust acceleration control, or the like.

Note that the operation space inertia inverse matrix $\Lambda^{-1}$ and the bias acceleration c involve large calculation cost if being calculated as the above Formulae (3) and (4) being definition formulae. Accordingly, there is proposed a method of calculating calculation processing of the operation space inertia inverse matrix $\Lambda^{-1}$ at higher speed by applying quasi-dynamics calculation (FWD) for obtaining generalized acceleration (joint acceleration) from generalized force (joint force $\tau$) of a multi-link structure. Specifically, by using the forward dynamics calculation FWD, the operation space inertia inverse matrix $\Lambda^{-1}$ and the bias acceleration c can be obtained from information regarding force acting on the multi-link structure (for example, the arm portion 420 and the joint portions 421a to 421f), such as the joint space q, the joint force $\tau$, or the gravity g. In this manner, by applying the forward dynamics calculation FWD regarding the operation space, it is possible to calculate the operation space inertia inverse matrix $\Lambda^{-1}$ by a calculation amount of O(N) for the number N of joint portions.

Here, as a setting example of an exercise purpose, a condition for achieving a target value (represented by adding a superscript bar to a second order differential of x) of the operation space acceleration with the virtual force $f_{vi}$ being equal to or less than an absolute value $F_i$ can be represented by the following Formula (6).

[Math. 5]

$$L_i = -F_i,$$

$$U_i = F_i,$$

$$\ddot{x}_i = \bar{\ddot{x}}_i \tag{6}$$

Furthermore, as mentioned above, an exercise purpose regarding a position or a speed of the operation space x can be represented as a target value of operation space acceleration, and specifically, can be represented by the following Formula (7) (target value of a position or a speed of the operation space x is represented by x, and adding a superscript bar to a first order differential of x).

[Math. 6]

$$\bar{\ddot{x}}_i = K_p(\bar{x}_i - x_i) + K_v(\bar{\dot{x}}_i - \dot{x}_i) \tag{7}$$

Additionally, by using a way of thinking of a decomposition operation space, it is possible to set an exercise purpose regarding an operation space (momentum, Cartesian relative coordinate, interlocked joint, or the like) represented by a linear sum of other operation spaces. Note that it is necessary give priorities to competing exercise purposes. It is possible to solve the above-described LCP for each priority and from the ascending order of priority, and cause virtual force obtained in the preceding LCP, to act as known external force of the following LCP.

(2-2-2. Real Force Calculation Processing)

In the real force calculation processing being the second stage of the generalized inverse dynamics, processing of substituting the virtual force $f_v$ obtained in the above-described (2-2-1. Virtual force decision process), with real joint force and external force is performed. A condition for realizing generalized force $\tau_v = J_v^T f_v$ generated by virtual force by generated torque $\tau_a$ and external force $f_e$ generated at a joint portion is represented by the following Formula (8).

[Math. 7]

$$\begin{bmatrix} J_{vu}^T \\ J_{va}^T \end{bmatrix}(f_v - \Delta f_v) = \begin{bmatrix} J_{eu}^T \\ J_{ea}^T \end{bmatrix} f_e + \begin{bmatrix} 0 \\ \tau_a \end{bmatrix} \tag{8}$$

Here, a suffix a denotes an aggregate of driving joint portions (driving joint aggregate), and a suffix u denotes an aggregate of unactuated joint portions (unactuated joint aggregate). In other words, an upper row of the above Formula (8) denotes equilibrium of force in a space formed by unactuated joint portions (unactuated joint space), and a lower row denotes equilibrium of force in a space formed by driving joint portions (driving joint space). $J_{vu}$ and $J_{va}$ respectively denote an unactuated joint component and a driving joint component of Jacobian regarding an operation space in which the virtual force $f_v$ acts on. $J_{eu}$ and $J_{ea}$ respectively denote an unactuated joint component and a driving joint component of Jacobian regarding an operation space in which the external force $f_e$ acts on. $\Delta f_v$ denotes a component that cannot be realized by real force, among the virtual force $f_v$.

The upper row of the above Formula (8) is indeterminate, and it is possible to obtain $f_e$ and $\Delta f_v$ by solving a quadratic programming (QP) problem as indicated in the following Formula (9), for example.

[Math. 8]

$$\min \tfrac{1}{2}\varepsilon^T Q_1 \varepsilon + \tfrac{1}{2}\xi^T Q_2 \xi \text{ s.t. } U\xi \geq v \qquad (9)$$

Here, $\varepsilon$ denotes a difference between both sides in the upper row of the above Formula (8), and denotes an equation error of Formula (8). $\xi$ is a linked vector of $f_e$ and $\Delta f_v$, and denotes a variable vector. $Q_1$ and $Q_2$ are positive definite symmetric matrix denoting weights in minimization. Furthermore, an inequality constraint of the above Formula (9) is used for representing a constraint condition regarding external force such as vertical reactive force, friction cone, a largest value of external force, or a support polygon. For example, an inequality constraint regarding a rectangular support polygon is represented as in the following Formula (10).

[Math. 9]

$$|F_x| \leq \mu_t F_z,$$

$$|F_y| \leq \mu_t F_z,$$

$$F_z \geq 0,$$

$$|M_x| \leq d_y F_z,$$

$$|M_y| \leq d_x F_z,$$

$$|M_z| \leq \mu_r F_z \qquad (10)$$

Here, z denotes a normal direction of a contact surface, and x and y denote orthogonal two tangential directions vertical to z. $(F_x, F_y, F_z)$ and $(M_x, M_y, M_z)$ external force and external force moment acting on a contact point. $\mu_t$ and $\mu_r$ are friction coefficient regarding translation and rotation, respectively. $(d_x, d_y)$ denotes a size of a support polygon.

From the above Formulae (9) and (10), solutions $f_e$ and $\Delta f_v$ of a minimum norm or a minimal error are obtained. By substituting $f_e$ and $\Delta f_v$ obtained from the above Formula (9), into the lower row of the above Formula (8), it is possible to obtain a joint force $\tau_a$ necessary for realizing an exercise purpose.

In the case of a system in which a base is fixed and an unactuated joint is not provided, all virtual force can be substituted only by joint force, and $f_e=0$ and $\Delta f_v=0$ can be obtained in the above Formula (8). In this case, it is possible to obtain the following Formula (11) for the joint force $\tau_a$, from the lower row of the above Formula (8).

[Math. 10]

$$\tau_a = J_{va}^T f_v \qquad (11)$$

Heretofore, the total body harmonized control that uses the generalized inverse dynamics according to the present embodiment has been described. As described above, by performing the virtual force calculation processing and the real force calculation processing in order, it is possible to obtain the joint force $\tau_a$ for achieving a desired exercise purpose. In other words, conversely, by reflecting the calculated joint force $\tau_a$ in a theoretical model in the movement of the joint portions 421a to 421f, the joint portions 421a to 421f are driven so as to achieve a desired exercise purpose.

Note that in the total body harmonized control that uses the generalized inverse dynamics described so far, in particular, regarding the details of a derivation process of the virtual force $f_v$, a method of solving the above-described LCP and obtaining the virtual force $f_v$, a solution method of the QP problem, or the like, it is possible to refer to JP 2009-95959 A and JP 2010-188471 A, which are prior patent applications filed by the applicant of the subject application, for example.

<<2-3. Ideal Joint Control>>

Next, the ideal joint control according to the present embodiment will be described. The movement of each of the joint portions 421a to 421f is modeled by a motion equation of a second lag system of the following Formula (12).

[Math. 11]

$$I_a \ddot{q} = \tau_a + \tau_e - \nu_a \dot{q} \qquad (12)$$

Here, $I_a$ is a inertia moment (inertia) at a joint portion, $\tau_a$ is generated torque of the joint portions 421a to 421f, $\tau_e$ is external torque acting on each of the joint portions 421a to 421f from the outside, and $\nu_e$ is a viscous resistance coefficient at each of the joint portions 421a to 421f. The above Formula (12) can also be said to be a theoretical model representing a movement of the actuator 430 at the joint portions 421a to 421f.

As described in the above <<2-2. Generalized inverse dynamics>>, by the calculation that uses the generalized inverse dynamics, it is possible to calculate $\tau_a$ being real force that is to act on each of the joint portions 421a to 421f for realizing the exercise purpose, using an exercise purpose and a constraint condition. Accordingly, ideally, by applying calculated each $\tau_a$ to the above Formula (12), a response that follows the theoretical model indicated in the above Formula (12) is implemented, in other words, a desired exercise purpose is achieved.

However, actually, in some cases, by the influence of various disturbances, an error (modeling error) is generated between the movement of the joint portions 421a to 421f and the theoretical model as indicated in the above Formula (12). The modeling error can be broadly-divided into a modeling error attributed to a mass property such as weight of a multi-link structure, a centroid, or inertia tensor, and a modeling error attributed to friction, inertia, or the like in the joint portions 421a to 421f. Among these modeling errors, the former modeling error attributed to a mass property can be reduced relatively easily in constructing a theoretical model, by increasing the accuracy of computer aided design (CAD) data or by the application of an identification method.

On the other hand, the latter modeling error attributed to friction, inertia, or the like in the joint portions 421a to 421f is attributed to a phenomenon in which it is difficult to perform modeling, such as friction in the reduction gear 426 of the joint portions 421a to 421f, for example, and an unignorable modeling error can stay in constructing a theoretical model. Furthermore, there is a possibility that an error is generated between values of the inertia $I_a$ and the viscous resistance coefficient $v_a$ in the above Formula (12), and these values in the actual joint portions 421a to 421f. These errors difficult to be modeled can be disturbance in the driving control of the joint portions 421a to 421f. Accordingly, by the influence of such disturbance, actually, the movement of the joint portions 421a to 421f does not respond just like a theoretical model indicated in the above Formula (12) in some cases. Thus, if the real force $\tau_a$ being joint force calculated by generalized inverse dynamics is applied, an exercise purpose being a control target sometimes fails to be achieved. In the present embodiment, by applying an active control system to each of the joint portions 421a to 421f, it is considered to correct a response of the joint portions 421a to 421f so as to perform an ideal response that follows the theoretical model indicated in the above Formula (12). Specifically, in the present embodiment, it becomes possible to perform friction compensated torque control that uses the torque sensor 428 or 428a of the joint portions 421a to 421f, and moreover, perform an ideal response that follows a theoretical value including the inertia $I_a$ and the viscous resistance coefficient $v_a$, to the required generated torque $\tau_a$ and the external torque $\tau_e$.

In the present embodiment, in this manner, controlling the driving of a joint portion in such a manner that the joint portions 421a to 421f of the support arm device 400 perform an ideal response as indicated in the above Formula (12) illustrated in is called ideal joint control. Here, in the following description, an actuator the driving of which is controlled by the ideal joint control is also called a virtualized actuator (VA) because an ideal response is performed. Hereinafter, the ideal joint control according to the present embodiment will be described with reference to FIG. 7.

Figure 7:
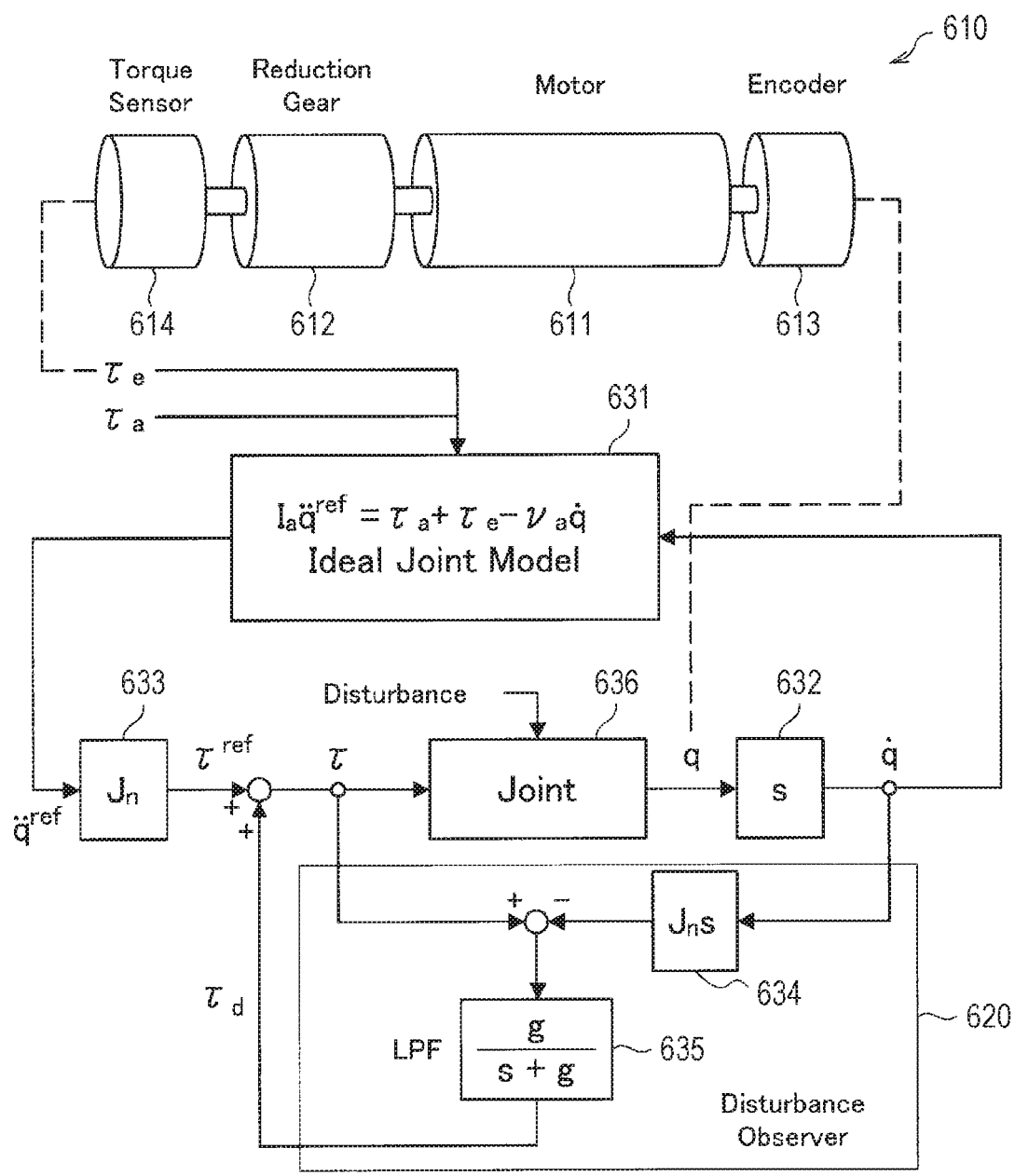
FIG. 7 is an explanatory diagram for describing ideal joint control according to an embodiment of the present disclosure.

FIG. 7 is an explanatory diagram for describing ideal joint control according to an embodiment of the present disclosure. Note that FIG. 7 schematically illustrates conceptional calculators that perform various calculations related to the ideal joint control, using blocks.

Referring to FIG. 7, an actuator 610 schematically illustrates a mechanism of the actuator 430 illustrated in FIG. 5, and a motor 611, a reduction gear 612, an encoder 613, and a torque sensor 614 respectively correspond to the motor 424, the reduction gear 426, the encoder 427, and the torque sensor 428 (or the torque sensor 428a illustrated in FIG. 6B) illustrated in FIG. 5.

Here, the actuator 610 performing a response that follows the theoretical model represented by the above Formula (12) means rotational angle acceleration on the left-hand side being achieved when the right-hand side of the above Formula (12) is given. Furthermore, as indicated in the above Formula (12), the theoretical model includes an external torque term $\tau_e$ acting on the actuator 610. In the present embodiment, for performing ideal joint control, the external torque $\tau_e$ is measured by the torque sensor 614. Furthermore, a disturbance observer 620 is applied for calculating a disturbance estimation value $\tau_d$ being an estimation value of torque attributed to disturbance, on the basis of the rotational angle q of the actuator 610 that has been measured by the encoder 613.

A block 631 represents a calculator that performs calculation that follows an ideal joint model of the joint portions 421a to 421f indicated in the above Formula (12). The block 631 can output rotational angle acceleration target value (second-order differential of rotational angle target value $q^{ref}$) indicated in the left-hand side of the above Formula (12), using the generated torque $\tau_a$, the external torque $\tau_e$, and the rotational angular speed (first-order differential of rotational angle q) as inputs.

In the present embodiment, the generated torque $\tau_a$ calculated using the method described in the above <<2-2. Generalized inverse dynamics>>, and the external torque $\tau_e$ measured by the torque sensor 614 are input to the block 631. On the other hand, by inputting the rotational angle q measured by the encoder 613, to a block 632 representing a calculator that performs differential calculation, a rotational angular speed (first-order differential of the rotational angle q) is calculated. By inputting the rotational angular speed calculated by the block 632, to the block 631 in addition to the above-described generated torque $\tau_a$ and external torque $\tau_e$, a rotational angle acceleration target value is calculated by the block 631. The calculated rotational angle acceleration target value is input to a block 633.

A block 633 represents a calculator that calculates torque generated in the actuator 610, on the basis of the rotational angle acceleration of the actuator 610. In the present embodiment, specifically, the block 633 can obtain a torque target value $\tau^{ref}$ by multiplying the rotational angle acceleration target value by nominal inertia $J_n$ in the actuator 610. In an ideal response, by causing the actuator 610 to generate the torque target value $\tau^{ref}$, a desired exercise purpose is achieved, but as mentioned above, in an actual response, the influence of disturbance or the like is sometimes generated. Accordingly, in the present embodiment, the disturbance estimation value $\tau_d$ is calculated by the disturbance observer 620, and the torque target value $\tau^{ref}$ is corrected using the disturbance estimation value $\tau_d$.

The configuration of the disturbance observer 620 will be described. As illustrated in FIG. 7, the disturbance observer 620 calculates the disturbance estimation value $\tau_d$ on the basis of a torque command value $\tau$ and the rotational angular speed calculated from the rotational angle q measured by the encoder 613. Here, the torque command value $\tau$ is a torque value finally generated by the actuator 610 after the influence of disturbance is corrected. For example, in a case where the disturbance estimation value $\tau_d$ is not calculated, the torque command value $\tau$ becomes a torque target value $\tau^{ref}$.

The disturbance observer 620 includes a block 634 and a block 635. A block 634 represents a calculator that calculates torque generated in the actuator 610, on the basis of the rotational angular speed of the actuator 610. In the present embodiment, specifically, the rotational angular speed calculated by the block 632 from the rotational angle q measured by the encoder 613 is input into the block 634. By performing calculation represented by the transfer function $J_n s$, in other words, by differentiating the rotational angular speed, the block 634 can obtain rotational angle acceleration, and calculate an estimation value of torque actually acting on the actuator 610 (torque estimation value), by further multiplying the calculated rotational angle acceleration by the nominal inertia $J_n$.

In the disturbance observer 620, by obtaining a difference between the torque estimation value and the torque command value $\tau$, a disturbance estimation value $\tau_d$ being a value of torque caused by disturbance is estimated. Specifically, the disturbance estimation value $\tau_d$ may be a difference between the torque command value $\tau$ in the previous control and a torque estimation value in this control. Because the torque estimation value calculated by the block 634 is based on an actual measurement value, and the torque command value $\tau$ calculated by the block 633 is based on the ideal theoretical model of the joint portions 421a to 421f that is represented by the block 631, by obtaining a difference therebetween, it is possible to estimate the influence of disturbance not considered in the above-described theoretical model.

Furthermore, the disturbance observer 620 is provided with a low pass filter (LPF) represented in the block 635, for preventing dispersion of the system. By performing calculation represented by a transfer function g/(s+g), the block 635 outputs only a low-frequency component for an input value, and stabilizes the system. In the present embodiment, a difference value between the torque estimation value calculated by the block 634, and the torque command value $\tau^{ref}$ is input to the block 635, and the low-frequency component is calculated as the disturbance estimation value $\tau_d$.

In the present embodiment, by performing feedforward control of adding the disturbance estimation value $\tau_d$ calculated by the disturbance observer 620, to the torque target value $\tau^{ref}$, the torque command value τ being a torque value to be finally generated by the actuator 610 is calculated. Then, the actuator 610 is driven on the basis of the torque command value τ. Specifically, the actuator 610 is driven by the torque command value τ being converted into a corresponding current value (current command value), and the current command value being applied to the motor 611.

Heretofore, by employing the configuration described with reference to FIG. 7, in the driving control of the joint portions 421a to 421f according to the present embodiment, even in a case where there is a disturbance component such as friction, it becomes possible to cause a response of the actuator 610 to follow a target value. Furthermore, regarding the driving control of the joint portions 421a to 421f, it becomes possible to perform an ideal response that follows the inertia $I_a$ and the viscous resistance coefficient $v_a$ supposed by a theoretical model.

Note that, regarding the details of the ideal joint control described above, it is possible to refer to JP 2009-269102 A, which is a prior patent application filed by the applicant of the subject application, for example.

Heretofore, the generalized inverse dynamics used in the present embodiment has been described, and the ideal joint control according to the present embodiment has been described with reference to FIG. 7. As described above, in the present embodiment, by using the generalized inverse dynamics, total body harmonized control of calculating a drive parameter of each of the joint portions 421a to 421f (for example, generated torque values of the joint portions 421a to 421f) for achieving an exercise purpose of the arm portion 420, considering a constraint condition is performed. Furthermore, as described with reference to FIG. 7, in the present embodiment, by performing the correction that considers the influence of disturbance, on the generated torque value calculated by the total body harmonized control that uses the above-described generalized inverse dynamics, ideal joint control of implementing an ideal response that is based on a theoretical model in the driving control of the joint portions 421a to 421f is performed. Accordingly, in the present embodiment, regarding the driving of the arm portion 420, it becomes possible to perform accurate driving control for achieving an exercise purpose.

<<2-4. Configuration of Support Arm Control System>>

Next, the configuration of the support arm control system according to the present embodiment in which the total body harmonized control and the ideal joint control that have been described in the above <<2-2. Generalized inverse dynamics>> and the above <<2-3. Ideal joint control>> are applied to the driving control of a support arm device will be described.

Figure 8:
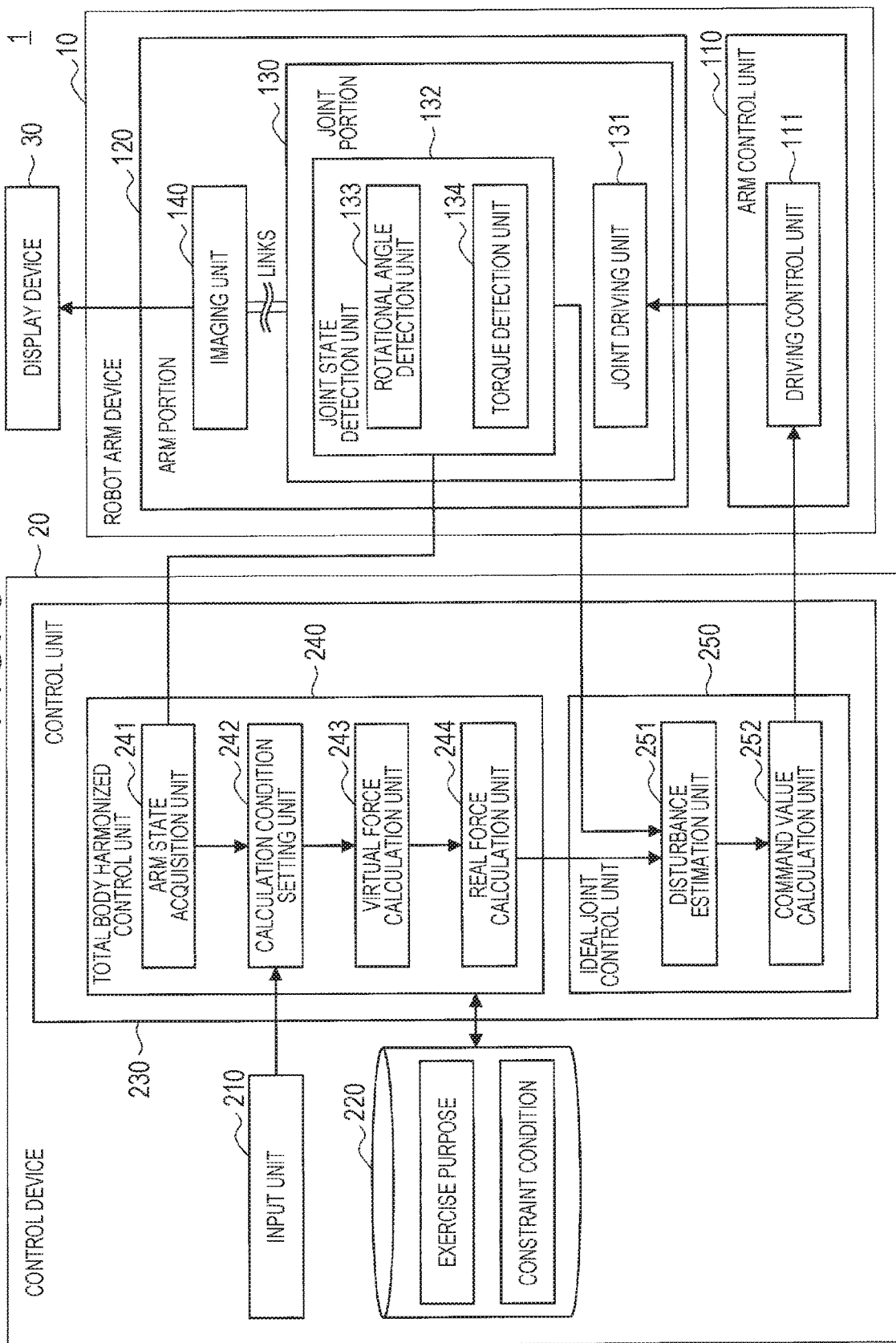
FIG. 8 is a functional block diagram illustrating a configuration example of a support arm control system according to an embodiment of the present disclosure.

One configuration example of a support arm control system according to an embodiment of the present disclosure will be described with reference to FIG. 8. FIG. 8 is a functional block diagram illustrating a configuration example of a support arm control system according to an embodiment of the present disclosure. Note that, in the support arm control system illustrated in FIG. 8, configurations regarding the driving control of an arm portion of a support arm device are mainly illustrated.

Referring to FIG. 8, a support arm control system 1 according to an embodiment of the present disclosure includes a support arm device 10, a control device 20, and a display device 30. In the present embodiment, the total body harmonized control described in the above <<2-2. generalized inverse dynamics>> and various calculations in the ideal joint control described in the above <<2-3. ideal joint control>> are performed by the control device 20, and the driving of an arm portion of the support arm device 10 is controlled on the basis of the calculation results. Note that the control device 20 includes a processor such as a CPU, for example, and controls the driving of an arm portion of the support arm device 10 by operating in accordance with a predetermined program. Furthermore, the arm portion of the support arm device 10 is provided with an imaging unit 140 as described later, and an image captured by the imaging unit 140 is displayed on a display screen of the display device 30. Hereinafter, the configurations of the support arm device 10, the control device 20, and the display device 30 will be described in detail.

The support arm device 10 includes an arm portion being a multi-link structure including a plurality of joint portions and a plurality of links, and performs control of a position and orientation of a distal end unit provided at a distal end of the arm portion, by driving the arm portion within a movable range. The support arm device 10 corresponds to the support arm device 400 illustrated in FIG. 3.

Referring to FIG. 8, the support arm device 10 includes an arm control unit 110 and an arm portion 120. Furthermore, the arm portion 120 includes a joint portion 130 and the imaging unit 140.

The arm control unit 110 comprehensively controls the support arm device 10, and controls the driving of the arm portion 120. The arm control unit 110 corresponds to the control unit (not illustrated in FIG. 3) described with reference to FIG. 3. Specifically, the arm control unit 110 includes a driving control unit 111, and the driving of the arm portion 120 is controlled by the driving of the joint portion 130 being controlled by control from the driving control unit 111. More specifically, the driving control unit 111 controls a rotational angle and generated torque in the joint portion 130 by controlling the number of rotations of a motor by controlling an amount of current to be supplied to the motor in an actuator of the joint portion 130. However, as mentioned above, the driving control of the arm portion 120 that is performed by the driving control unit 111 is performed on the basis of a calculation result in the control device 20. Accordingly, an amount of current to be supplied to the motor in the actuator of the joint portion 130 that is to be controlled by the driving control unit 111 is a current amount to be decided on the basis of a calculation result in the control device 20.

The arm portion 120 is a multi-link structure including a plurality of joint portions and a plurality of links, and the driving thereof is controlled by control from the arm control unit 110. The arm portion 120 corresponds to the arm portion 420 illustrated in FIG. 3. The arm portion 120 includes the joint portion 130 and the imaging unit 140. Note that, because the functions and configurations of the plurality of joint portions included in the arm portion 120 are similar to each other, in FIG. 8, the configuration of one joint portion 130 is illustrated on behalf of the plurality of joint portions.

The joint portion 130 rotatably couples between links in the arm portion 120, and drives the arm portion 120 by the rotational driving thereof being controlled by control from the arm control unit 110. The joint portion 130 corresponds to the joint portions 421a to 421f illustrated in FIG. 3. Furthermore, the joint portion 130 includes an actuator, and the configuration of the actuator is similar to the configuration illustrated in, for example, FIGS. 5, 6A, and 6B.

The joint portion 130 includes a joint driving unit 131 and a joint state detection unit 132.

The joint driving unit 131 is a driving mechanism of the actuator in the joint portion 130, and the joint portion 130 is rotationally driven by the driving of the joint driving unit 131. The driving of the joint driving unit 131 is controlled by the driving control unit 111. For example, the joint driving unit 131 is a configuration corresponding to the motor 424 and the motor driver 425 illustrated in FIG. 5, and driving of the joint driving unit 131 corresponds to the motor driver 425 driving the motor 424 using a current amount corresponding to a command from the driving control unit 111.

The joint state detection unit 132 detects a state of the joint portion 130. Here, the state of the joint portion 130 may mean the state of the movement of the joint portion 130. For example, the state of the joint portion 130 includes information regarding a rotational angle, a rotational angular speed, rotational angle acceleration, generated torque, or the like of the joint portion 130. In the present embodiment, the joint state detection unit 132 includes a rotational angle detection unit 133 that detects a rotational angle of the joint portion 130, and a torque detection unit 134 that detects generated torque of the joint portion 130 and external torque. Note that the rotational angle detection unit 133 and the torque detection unit 134 respectively correspond to the encoder 427 of the actuator 430 illustrated in FIG. 5, and the torque sensors 428 and 428a illustrated in FIGS. 6A and 6B. The joint state detection unit 132 transmits the detected state of the joint portion 130, to the control device 20.

The imaging unit 140 is an example of the distal end unit provided at the distal end of the arm portion 120, and acquires an image of an image capturing target. The imaging unit 140 corresponds to the endoscope device 423 illustrated in FIG. 3. Specifically, the imaging unit 140 is a camera or the like that can capture an image of an image capturing target in a format of a moving image or a still image. More specifically, the imaging unit 140 includes a plurality of two-dimensionally arrayed light receiving elements, and can acquire an image signal representing an image of an image capturing target by photoelectric conversion in the light receiving elements. The imaging unit 140 transmits the acquired image signal to the display device 30.

Note that, as the endoscope device 423 provided at the distal end of the arm portion 420 in the support arm device 400 illustrated in FIG. 3, also in the support arm device 10, the imaging unit 140 is actually provided at the distal end of the arm portion 120. FIG. 8 represents a state in which the imaging unit 140 is provided at the distal end of the last link via a plurality of joint portions 130 and a plurality of links, by schematically illustrating links between the joint portion 130 and the imaging unit 140.

Note that, in the present embodiment, various medical tools can be connected to the distal end of the arm portion 120 as distal end units. As the medical tools, for example, there are various units used in practice, such as various practice tools such as a surgical knife or forceps, or one unit of various checkup devices, such as a probe of an ultrasonic checkup device. Furthermore, in the present embodiment, the imaging unit 140 illustrated in FIG. 8, and a unit having an imaging function such as an endoscope or a microscope may also be included in the medical tools. In this manner, the support arm device 10 according to the present embodiment can be said to be a medical support arm device including a medical tool. Similarly, the support arm control system 1 according to the present embodiment can be said to be a medical support arm control system (medical system). Furthermore, a stereo camera including two imaging units (camera units) may be provided at the distal end of the arm portion 120, and an image may be captured in such a manner that an image capturing target is displayed as a 3D image.

Heretofore, functions and configurations of the support arm device 10 have been described. Next, functions and configurations of the control device 20 will be described. Referring to FIG. 8, the control device 20 includes an input unit 210, a storage unit 220, and a control unit 230.

The control unit 230 comprehensively controls the control device 20, and performs various calculations for controlling the driving of the arm portion 120 in the support arm device 10. Specifically, for controlling the driving of the arm portion 120 of the support arm device 10, the control unit 230 performs various calculations in the total body harmonized control and the ideal joint control. Hereinafter, functions and configurations of the control unit 230 will be described in detail, but the total body harmonized control and the ideal joint control have already been described in the above <<2-2. generalized inverse dynamics>> and the above <<2-3. ideal joint control>>. Thus, the detailed description will be omitted here.

The control unit 230 includes a total body harmonized control unit 240 and an ideal joint control unit 250.

The total body harmonized control unit 240 performs various calculations regarding the total body harmonized control that uses the generalized inverse dynamics. In the present embodiment, the total body harmonized control unit 240 acquires a state of the arm portion 120 (arm state) on the basis of the state of the joint portion 130 that has been detected by the joint state detection unit 132. Furthermore, on the basis of the arm state and an exercise purpose and a constraint condition of the arm portion 120, the total body harmonized control unit 240 calculates, using the generalized inverse dynamics, a control value for the total body harmonized control of the arm portion 120 in an operation space. Note that the operation space is, for example, a space for describing a relationship between force acting on the arm portion 120 and acceleration generated in the arm portion 120.

The total body harmonized control unit 240 includes an arm state acquisition unit 241, a calculation condition setting unit 242, a virtual force calculation unit 243, and a real force calculation unit 244.

The arm state acquisition unit 241 acquires a state of the arm portion 120 (arm state) on the basis of the state of the joint portion 130 that has been detected by the joint state detection unit 132. Here, the arm state may mean the state of the movement of the arm portion 120. For example, the arm state includes information regarding a position, a speed, acceleration, force, or the like of the arm portion 120. As mentioned above, the joint state detection unit 132 acquires, as the state of the joint portion 130, information regarding a rotational angle, a rotational angular speed, rotational angle acceleration, generated torque, or the like of each of the joint portions 130. Furthermore, as described later, the storage unit 220 stores various types of information to be processed by the control device 20, and in the present embodiment, various types of information regarding the arm portion 120 (arm information) may be stored in the storage unit 220. For example, information regarding the number of joint portions 130 and the number of links included in the arm portion 120, a connection status between the joint portions 130 and the links, the length of the links, or the like may be stored. The arm state acquisition unit 241 can acquire the arm information from the storage unit 220. Accordingly, on the basis of the state of the joint portion 130 and the arm information, the arm state acquisition unit 241 can acquire, as the arm state, information regarding positions (coordinates) on the space of the plurality of joint portions 130, the plurality of links, and the imaging unit 140 (in other words, the shape of the arm portion 120, position and orientation of the imaging unit 140), force acting on each of the joint portions 130, the links, and the imaging unit 140, or the like. The arm state acquisition unit 241 transmits the acquired arm information to the calculation condition setting unit 242.

The calculation condition setting unit 242 sets a calculation condition in calculation regarding the total body harmonized control that uses the generalized inverse dynamics. Here, the calculation condition may be an exercise purpose and a constraint condition. The exercise purpose may be various types of information regarding the movement of the arm portion 120. Specifically, an exercise purpose may be target values of a position and orientation (coordinate), a speed, acceleration, force, and the like of the imaging unit 140, or may be target values of positions (coordinates), speeds, acceleration, force, and the like of the plurality of joint portions 130 and the plurality of links of the arm portion 120. Furthermore, a constraint condition may be various types of information for restricting (constraining) the movement of the arm portion 120. Specifically, a constraint condition may be a coordinate of a region to which each component of the arm portion cannot move, a value of a speed or acceleration at which each component cannot move, a value of force that cannot be generated, or the like. Furthermore, limited ranges of various physical amounts in a constraint condition may be set in accordance with structural feasibility in the arm portion 120, or may be appropriately set by the user. Furthermore, the calculation condition setting unit 242 includes a physical model regarding the structure of the arm portion 120 (obtained by modelling, for example, the number of links included in the arm portion 120, the length of the links, the connection status of the links via the joint portions 130, a movable range of the joint portions 130, or the like), and a movement condition and a constraint condition may be set in the physical model by generating a control model in which a desired movement condition and a constraint condition are reflected.

In the present embodiment, by appropriately setting an exercise purpose and a constraint condition, it becomes possible to cause the arm portion 120 to perform a desired operation. For example, by setting a target value of a position of the imaging unit 140 as an exercise purpose, it is possible to naturally move the imaging unit 140 to the target position, and it is also possible to drive the arm portion 120 by setting a limitation on the movement using a constraint condition, such as preventing the arm portion 120 from entering a predetermined region on the space.

As a specific example of an exercise purpose, for example, an exercise purpose may be a pivot operation in which, in a state in which an imaging direction of the imaging unit 140 is fixed to an operative region, the imaging unit 140 moves within a surface of a circular cone having a vertex corresponding to the operative region, like a turning operation around an axis of the circular cone serving as a turning axis. Furthermore, in the pivot operation, a turning operation may be performed in a state in which a distance between the imaging unit 140 and a point corresponding to the vertex of the circular cone is kept constant. By performing such a pivot operation, it becomes possible to observe an observation region from an equal distance and from different angles. Thus, it is possible to enhance the convenience of the user who performs an operation.

Furthermore, as another specific example, an exercise purpose may be control content of generated torque in each of the joint portions 130. Specifically, an exercise purpose may be a power assist operation of controlling the state of the joint portion 130 so as to cancel the gravity acting on the arm portion 120, and further controlling the state of the joint portion 130 so as to support the movement of the arm portion 120 in a direction in which force is added from the outside. More specifically, in the power assist operation, a position and orientation of the arm portion 120 are held in a predetermined state by the driving of each of the joint portions 130 being controlled in such a manner that generated torque for cancelling external torque caused by gravity in each of the joint portions 130 of the arm portion 120 is generated in each of the joint portions 130. The driving of each of the joint portions 130 is controlled in such a manner that, in a case where external torque is further added from the outside in this state (for example, from the user), generated torque in the same direction as the added external torque is generated in each of the joint portions 130. By performing such a power assist operation, in a case where the user manually moves the arm portion 120, the user can move the arm portion 120 by smaller force. Thus, the user can feel as if the user moved the arm portion 120 in a gravity-free state. Furthermore, the aforementioned pivot operation and the power assist operation can be combined.

Here, in the present embodiment, an exercise purpose may mean an operation (movement) of the arm portion 120 implemented by the total body harmonized control, or may mean an instantaneous exercise purpose in the operation (in other words, target value in the exercise purpose). For example, in the case of the above-described pivot operation, an exercise purpose means the imaging unit 140 performing the pivot operation, and during the pivot operation, a value of a position, a speed, or the like of the imaging unit 140 within a conic surface in the pivot operation is set as an instantaneous exercise purpose (target value in the exercise purpose). Furthermore, for example, in the case of the above-described power assist operation, an exercise purpose means performing a power assist operation of supporting the movement of the arm portion 120 in a direction of force added from the outside, and during the power assist operation, a value of generated torque in the same direction as external torque added to each of the joint portions 130 is set as an instantaneous exercise purpose (target value in the exercise purpose). An exercise purpose in the present embodiment is a concept including both of an instantaneous exercise purpose (for example, a target value of a position, a speed, force, or the like of each component of the arm portion 120 at a certain time), and an operation of each component of the arm portion 120 that is to be implemented over time as a result of an instantaneous exercise purpose being consecutively achieved. Each step in the calculation for total body harmonized control in the total body harmonized control unit 240, an instantaneous exercise purpose is set in each step, and by the calculation being repeatedly performed, a desired exercise purpose is finally achieved.

Note that, in the present embodiment, when an exercise purpose is set, a viscous resistance coefficient in a rotational movement of each of the joint portions 130 may be appropriately set. As mentioned above, the joint portion 130 according to the present embodiment is configured to appropriately adjust a viscous resistance coefficient in a rotational movement of the actuator 430. Accordingly, by also setting a viscous resistance coefficient in a rotational movement of each of the joint portions 130 when an exercise purpose is set, for example, it is possible to realize a state in which rotation is easily performed by force added from the outside or a state in which it is difficult to perform rotation. For example, in the case of the aforementioned power assist operation, by setting a small viscous resistance coefficient in the joint portion 130, smaller force is required for the user moving the arm portion 120, and gravityless feeling to be added to the user is enhanced. In this manner, a viscous resistance coefficient in a rotational movement of each of the joint portions 130 may be appropriately set in accordance with the content of an exercise purpose.

Here, in the present embodiment, as described later, a parameter regarding a calculation condition of an exercise purpose, a constraint condition, or the like that is to be used in the calculation regarding the total body harmonized control may be stored into the storage unit 220. The calculation condition setting unit 242 can set a constraint condition stored in the storage unit 220, as a constraint condition to be used in the calculation of the total body harmonized control.

Furthermore, in the present embodiment, the calculation condition setting unit 242 can set an exercise purpose using a plurality of methods. For example, the calculation condition setting unit 242 may set an exercise purpose on the basis of the arm state transmitted from the arm state acquisition unit 241. As mentioned above, the arm state includes information regarding a position of the arm portion 120, and information regarding force acting on the arm portion 120. Accordingly, for example, in a case where the user manually moves the arm portion 120, information regarding how the user moves the arm portion 120 is also acquired by the arm state acquisition unit 241 as an arm state. Accordingly, on the basis of the acquired arm state, the calculation condition setting unit 242 can set, as an instantaneous exercise purpose, a position, a speed, force, or the like to (at, by) which the user moves the arm portion 120. In this manner, by setting an exercise purpose, the driving of the arm portion 120 is controlled so as to follow and support the movement of the arm portion 120 that is caused by the user.

Furthermore, for example, the calculation condition setting unit 242 may set an exercise purpose on the basis of an instruction input by the user from the input unit 210. As described later, the input unit 210 is an input interface for the user inputting, to the control device 20, information regarding the driving control of the support arm device 10, a command, or the like, and in the present embodiment, an exercise purpose may be set on the basis of an operation input from the input unit 210 that is performed by the user. Specifically, the input unit 210 may include, for example, an operation means operated by the user, such as a lever or a pedal, and a position, a speed, or the like of each component of the arm portion 120 may be set by the calculation condition setting unit 242 as an instantaneous exercise purpose in accordance with the operation of the lever, pedal, or the like.

Moreover, for example, the calculation condition setting unit 242 may set an exercise purpose stored in the storage unit 220, as an exercise purpose used in the calculation of the total body harmonized control. For example, in the case of an exercise purpose for causing the imaging unit 140 to stop at a predetermined point on the space, it is possible to preset a coordinate of the predetermined point as an exercise purpose. Furthermore, for example, in the case of an exercise purpose for causing the imaging unit 140 to move along a predetermined trajectory on the space, it is possible to preset a coordinate of each point indicating the predetermined trajectory, as an exercise purpose. In this manner, in a case where an exercise purpose can be preset, the exercise purpose may be prestored into the storage unit 220. Furthermore, for example, in the case of the aforementioned pivot operation, an exercise purpose is limited to an exercise purpose in which a position on the surface of a circular cone, a speed, or the like is used as a target value, and in the case of the power assist operation, an exercise purpose is limited to an exercise purpose in which force is used as a target value. In this manner, in a case where an exercise purpose is preset as in the pivot operation or the power assist operation, information regarding the range, the type, or the like of a target value settable as an instantaneous exercise purpose in these exercise purposes may be stored in the storage unit 220. The calculation condition setting unit 242 can set, as an exercise purpose, information including various types of information regarding such an exercise purpose.

Note that, among the above-described methods, a method of setting an exercise purpose that is to be used by the calculation condition setting unit 242 may be appropriately settable by the user in accordance with a use application or the like of the support arm device 10. Furthermore, the calculation condition setting unit 242 may set an exercise purpose and a constraint condition by appropriately combining the above-described methods. Note that priority of an exercise purpose may be set in a constraint condition stored in the storage unit 220, and in a case where a plurality of different exercise purposes exists, the calculation condition setting unit 242 may set an exercise purpose in accordance with the priority of the constraint condition. The calculation condition setting unit 242 transmits the arm state and the set an exercise purpose and a constraint condition to the virtual force calculation unit 243.

The virtual force calculation unit 243 calculates virtual force in the calculation regarding the total body harmonized control that uses the generalized inverse dynamics. The calculation processing of virtual force that is to be performed by the virtual force calculation unit 243 may be a series of processes described in, for example, the above (2-2-1. Virtual force calculation processing). The virtual force calculation unit 243 transmits the calculated virtual force $f_v$ to the real force calculation unit 244.

The real force calculation unit 244 calculates real force in the calculation regarding the total body harmonized control that uses the generalized inverse dynamics. The calculation processing of real force that is to be performed by the real force calculation unit 244 may be a series of processes described in, for example, the above (2-2-2. Real force calculation processing). The real force calculation unit 244 transmits the calculated real force (generated torque) $\tau_a$ to the ideal joint control unit 250. Note that, in the present embodiment, the generated torque $\tau_a$ calculated by the real force calculation unit 244 is also called a control value or a control torque value meaning a control value of the joint portion 130 in the total body harmonized control.

The ideal joint control unit 250 performs various calculations regarding the ideal joint control that uses the generalized inverse dynamics. In the present embodiment, the ideal joint control unit 250 calculates a torque command value $\tau$ for implementing an ideal response of the arm portion 120 by correcting the influence of disturbance for the generated torque $\tau_a$ calculated by the real force calculation unit 244. Note that calculation processing performed by the ideal joint control unit 250 corresponds to a series of processes described in the above <<2-3. Ideal joint control>>.

The ideal joint control unit 250 includes a disturbance estimation unit 251 and a command value calculation unit 252.

The disturbance estimation unit 251 calculates a disturbance estimation value $\tau_d$ on the basis of the torque command value $\tau$, and the rotational angular speed calculated from the rotational angle q detected by the rotational angle detection unit 133. Note that the torque command value $\tau$ here is a command value indicating generated torque of the arm portion 120 that is to be finally transmitted to the support arm device 10. In this manner, the disturbance estimation unit 251 has a function corresponding to the disturbance observer 620 illustrated in FIG. 7.

Using the disturbance estimation value $\tau_d$ calculated by the disturbance estimation unit 251, the command value calculation unit 252 calculates the torque command value T being a command value indicating torque to be generated in the arm portion 120 that is to be finally transmitted to the support arm device 10. Specifically, the command value calculation unit 252 calculates the torque command value $\tau$ by adding the disturbance estimation value $\tau_d$ calculated by the disturbance estimation unit 251, to $\tau^{ref}$ calculated from the ideal model of the joint portion 130 that is indicated in the above Formula (12). For example, in a case where the disturbance estimation value $\tau_d$ is not calculated, the torque command value T becomes a torque target value $\tau^{ref}$. In this manner, the function of the command value calculation unit 252 corresponds to functions other than the disturbance observer 620 illustrated in FIG. 7.

As described above, in the ideal joint control unit 250, information exchange being repeatedly performed between the disturbance estimation unit 251 and the command value calculation unit 252, a series of processes described with reference to FIG. 7 are performed. The ideal joint control unit 250 transmits the calculated torque command value $\tau$ to the driving control unit 111 of the support arm device 10. By performing control of supplying current with an amount corresponding to the transmitted torque command value $\tau$, to the motor in the actuator of the joint portion 130, the driving control unit 111 controls the number of rotations of the motor, and controls a rotational angle and generated torque in the joint portion 130.

In the support arm control system 1 according to the present embodiment, because the driving control of the arm portion 120 in the support arm device 10 is continuously performed while works using the arm portion 120 are being performed, the above-described processes in the support arm device 10 and the control device 20 are repeatedly performed. In other words, the state of the joint portion 130 is detected by the joint state detection unit 132 of the support arm device 10 and transmitted to the control device 20. In the control device 20, on the basis of the state of the joint portion 130, an exercise purpose, and a constraint condition, various calculations regarding the total body harmonized control and the ideal joint control for controlling the driving of the arm portion 120 are performed, and the torque command value T serving as a calculation result is transmitted to the support arm device 10. In the support arm device 10, the driving of the arm portion 120 is controlled on the basis of the torque command value $\tau$, and the state of the joint portion 130 during the driving or after the driving is detected again by the joint state detection unit 132.

The description regarding other configurations included in the control device 20 will be continued.

The input unit 210 is an input interface for the user inputting, to the control device 20, information regarding the driving control of the support arm device 10, a command, or the like. In the present embodiment, on the basis of an operation input from the input unit 210 that is performed by the user, the driving of the arm portion 120 of the support arm device 10 may be controlled, and a position and orientation of the imaging unit 140 may be controlled. Specifically, as mentioned above, by inputting, to the calculation condition setting unit 242, instruction information regarding an instruction of the driving of the arm that has been input from the input unit 210 by the user, the calculation condition setting unit 242 may set an exercise purpose in the total body harmonized control on the basis of the instruction information. In this manner, by performing the total body harmonized control using the exercise purpose that is based on the instruction information input by the user, the driving of the arm portion 120 that corresponds to the operation input of the user is implemented.

Specifically, the input unit 210 includes an operation means to be operated by the user, such as, for example, a mouse, a keyboard, a touch panel, a button, a switch, a lever, and a pedal. For example, in a case where the input unit 210 includes a pedal, the user can control the driving of the arm portion 120 by operating the pedal by foot. Accordingly, even in a case where the user is performing treatment on an operative region of a patient with both hands, it is possible to adjust, by a pedal operation by foot, a position and orientation of the imaging unit 140, in other words, an imaging position and an imaging angle of the operative region.

The storage unit 220 stores various types of information to be processed by the control device 20. In the present embodiment, the storage unit 220 can store various parameters to be used in the total body harmonized control and the ideal joint control regarding calculation to be performed by the control unit 230. For example, the storage unit 220 may store an exercise purpose and a constraint condition that are to be used in the calculation regarding the total body harmonized control to be performed by the total body harmonized control unit 240. As mentioned above, an exercise purpose stored in the storage unit 220 may be, for example, an exercise purpose that can be preset, such as an exercise purpose for causing the imaging unit 140 to stop at a predetermined point on the space. Furthermore, a constraint condition may be preset by the user in accordance with a geometric configuration of the arm portion 120, a use application of the support arm device 10, or the like, and stored into the storage unit 220. Furthermore, various types of information regarding the arm portion 120 that are to be used when the arm state acquisition unit 241 acquires an arm state may be stored into the storage unit 220. Moreover, calculation results in the calculations regarding the total body harmonized control and the ideal joint control to be performed by the control unit 230, numerical values calculated in calculation processes, and the like may be stored into the storage unit 220. In this manner, any parameter regarding various processes to be performed by the control unit 230 may be stored into the storage unit 220, and the control unit 230 can perform various processes while exchanging information with the storage unit 220.

Heretofore, the functions and configurations of the control device 20 have been described. Note that the control device 20 according to the present embodiment can be formed by various information processing devices (arithmetic processing units) such as, for example, a personal computer (PC) or a server. Next, functions and configurations of the display device 30 will be described.

By displaying various types of information on a display screen in various formats such as text or images, the display device 30 visually notifies the information to the user. In the present embodiment, the display device 30 displays an image captured by the imaging unit 140 of the support arm device 10, on the display screen. Specifically, the display device 30 have functions and configurations of an image signal processing unit (not illustrated) that performs various types of image processing on an image signal acquired by the imaging unit 140, a display control unit (not illustrated) that performs control of displaying an image that is based on the processed image signal, on the display screen, and the like. Note that the display device 30 may have various functions and configurations that are included in a general display device, in addition to the above-described functions and configurations. The display device 30 corresponds to a display device 550 illustrated in FIG. 1.

Heretofore, the functions and configurations of the support arm device 10, the control device 20, and the display device 30 according to the present embodiment have been described with reference to FIG. 8. Each of the above-described components may be formed using a general-purpose member or circuit, or may be formed by hardware dedicated to the function of each component. Furthermore, all of the functions of the components may be performed by a CPU or the like. Accordingly, configurations to be used can be appropriately changed in accordance with a technology level when the present embodiment is implemented.

As described above, according to the present embodiment, the arm portion 120 being a multi-link structure in the support arm device 10 has a degree of freedom being at least six-degree of freedom or more, and the driving of each of the plurality of joint portions 130 included in the arm portion 120 is controlled by the driving control unit 111. Then, a medical tool is provided at the distal end of the arm portion 120. In this manner, by controlling the driving of each of the joint portions 130, the driving control of the arm portion 120 with a higher degree of freedom is implemented, and the medical support arm device 10 with higher operability for the user is realized.

More specifically, according to the present embodiment, in the support arm device 10, the state of the joint portion 130 is detected by the joint state detection unit 132. Then, in the control device 20, on the basis of the state of the joint portion 130, an exercise purpose, and a constraint condition, various calculations regarding the total body harmonized control that uses the generalized inverse dynamics for controlling the driving of the arm portion 120 are performed, and the torque command value $\tau$ serving as a calculation result is calculated. Moreover, in the support arm device 10, the driving of the arm portion 120 is controlled on the basis of the torque command value $\tau$. In this manner, in the present embodiment, the driving of the arm portion 120 is controlled by the total body harmonized control that uses the generalized inverse dynamics. Accordingly, the driving control of the arm portion 120 by force control is implemented, and a support arm device with a higher operability for the user is realized. Furthermore, in the present embodiment, in the total body harmonized control, for example, it becomes possible to perform control of realizing various exercise purposes for enhancing the convenience of the user, such as the pivot operation or the power assist operation. Moreover, in the present embodiment, because various driving means such as manually moving the arm portion 120 or moving the arm portion 120 in accordance with an operation input from a pedal, for example, are realized, the convenience of the user are further enhanced.

Furthermore, in the present embodiment, regarding the driving control of the arm portion 120, the ideal joint control is applied together with the total body harmonized control. In the ideal joint control, a disturbance component such as friction or inertia in the joint portion 130 is estimated, and feedforward control that uses the estimated disturbance component is performed. Accordingly, even in a case where there is a disturbance component such as friction, it is possible to implement an ideal response regarding the driving of the joint portion 130. Thus, in the driving control of the arm portion 120, high-accuracy responsivity, high positioning accuracy, and stability are realized with less influence of vibration or the like.

Moreover, in the present embodiment, each of the plurality of joint portions 130 included in the arm portion 120 has the configuration suitable for the ideal joint control, as illustrated in FIG. 5, for example, and it is possible to control a rotational angle, generated torque, and a viscous resistance coefficient in each of the joint portions 130, using a current value. In this manner, because the driving of each of the joint portions 130 is controlled using a current value, and the driving of each of the joint portions 130 is further controlled while recognizing the state of the entire arm portion 120 by the total body harmonized control, counterbalancing becomes unnecessary, and the support arm device 10 is downsized.

<<2-5. Overview of Movable Range Restriction and Movable Range Expansion of Arm>>

In the present embodiment, in a support arm including the aforementioned joint angle sensor and a force control actuator, and being controlled by the ideal joint control that is based on the generalized inverse dynamics, it is determined whether an arm distal end position is positioned within or outside a default safety movable range, low operation load on the force control actuator is set within the safety movable range, and high operation load is set outside the safety movable range (unsafe region). A movement operation in a new entry region of an arm distal end position is thereby restricted. Furthermore, by storing, in real time, an unsafe region through which the arm distal end position has once passed, and additionally expanding the region as a part of the safety movable range, a dynamic change of the safety movable range is enabled during the operation.

Figure 9A:
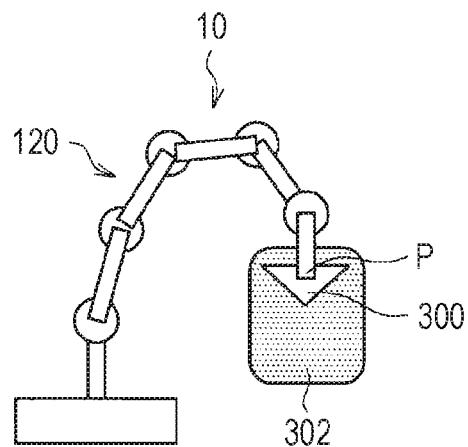
FIG. 9A is a diagram illustrating an example of movable range restriction of an arm according to the present embodiment, and is a schematic diagram illustrating a manual guide operation mode.
Figure 9B:
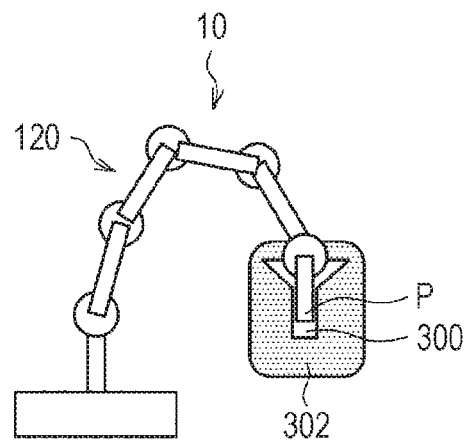
FIG. 9B is a diagram illustrating an example of movable range restriction of an arm according to the present embodiment, and is a schematic diagram illustrating a manual guide operation mode.
Figure 9C:
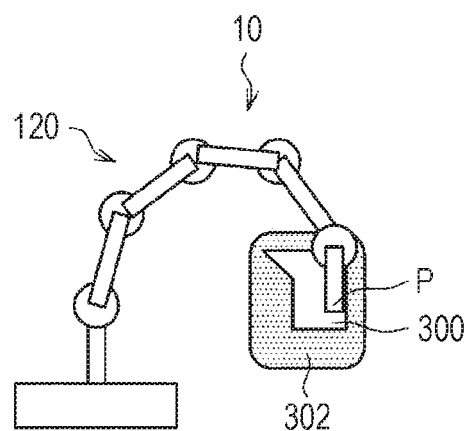
FIG. 9C is a diagram illustrating an example of movable range restriction of an arm according to the present embodiment, and is a schematic diagram illustrating a manual guide operation mode.

FIGS. 9A to 9C are schematic diagrams illustrating examples of movable range restriction of an arm according to the present embodiment, and illustrate a manual guide operation mode. In a safety movable range 300 illustrated in FIG. 9A, a viscous resistance coefficient in the joint portion 130 is low, and a manipulator can move the arm portion 120 in a state in which viscous load is low. On the other hand, in an unsafe region 302, because a viscous resistance coefficient is high, a manipulator cannot move an arm distal end (the working point P) to the unsafe region 302 unless an appreciable extent of load is applied to the arm. With this configuration, because the arm distal end does not easily enter the unsafe region 302, and the arm distal end does not contact a diseased portion, an object, and the like that are positioned within the unsafe region 302, safety can be ensured. Note that, here, the above-described arm distal end includes a distal end unit provided at the distal end of the arm portion 120. Furthermore, here, the working point P is assumed to be an arm distal end, but the working point P may be an arbitrary point on the arm portion 120, such as the joint portion 130. The working point P can be set to one or a plurality of arbitrary points on the arm portion 120, and for example, may be set to one or a plurality of joint portions 130 or one or a plurality of links. Furthermore, the working point P may be set to both of an arm distal end and the joint portion 130 (or link).

Furthermore, in a case where a manipulator desires to expand the safety movable range 300, the arm distal end is moved from the state illustrated in FIG. 9A, to the state illustrated in FIG. 9B. At this time, for causing the arm distal end to enter the unsafe region 302, the manipulator moves the arm distal end by applying an appreciable extent of load thereto. If the arm distal end enters the unsafe region 302, the safety movable range 300 is expanded. In the example illustrated in FIG. 9B, an example in which the manipulator moves the arm distal end to the lower side, and the safety movable range 300 is expanded. Accordingly, thereafter, virtual viscous load becomes lower in the expanded safety movable range, and the manipulator can easily operate the arm distal end within the expanded safety movable range 300. FIG. 9C illustrates an example in which the manipulator moves the arm distal end to the right side, from the state illustrated in FIG. 9B, and the safety movable range 300 is further expanded.

In this manner, in the manual guide operation mode, the manipulator can expand the safety movable range 300 by an operation and at a timing of the manipulator in accordance with an environment and a situation in which the arm is used.

Figure 10A:
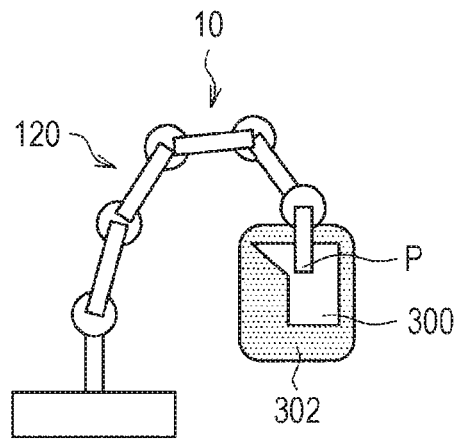
FIG. 10A is a diagram illustrating an example of movable range restriction of an arm according to the present embodiment, and is a schematic diagram illustrating an automatic guide operation mode.
Figure 10B:
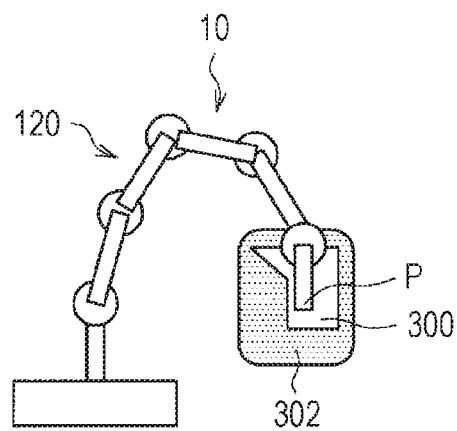
FIG. 10B is a diagram illustrating an example of movable range restriction of an arm according to the present embodiment, and is a schematic diagram illustrating an automatic guide operation mode.
Figure 10C:
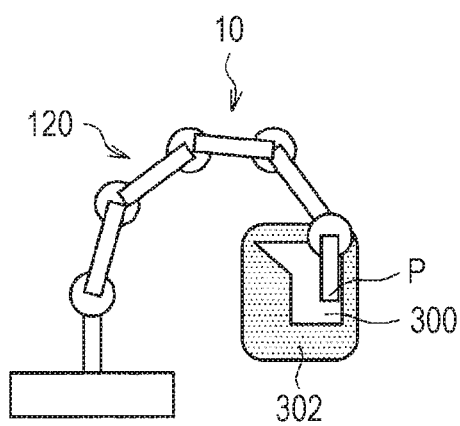
FIG. 10C is a diagram illustrating an example of movable range restriction of an arm according to the present embodiment, and is a schematic diagram illustrating an automatic guide operation mode.

FIGS. 10A to 10C illustrate states in an automatic guide operation mode, and illustrate states in which the safety movable range 300 is expanded to the state illustrated in FIG. 9C. In the automatic operation mode, it is possible to automatically move the arm distal end within the set safety movable range 300. Because the arm distal end does not easily enter the unsafe region 302, the arm distal end does not contact a diseased portion, an object, and the like that are positioned within the unsafe region 302, and safety can be surely guaranteed.

<<2-6. Overview of Harmonized Control of Plurality of Support Arms>>

Next, the overview of harmonized control of a plurality of support arms according to the present embodiment will be described. As mentioned above, in a support arm controlled by the ideal joint control that is based on the generalized inverse dynamics, the control device 20 according to the present embodiment determines whether an arm distal end position is positioned within or outside a default safety movable range, sets low operation load on the force control actuator within the safety movable range, and sets high operation load outside the safety movable range (unsafe region). A movement operation in a new entry region of an arm distal end position can thereby be restricted.

However, in an environment in which a plurality of the aforementioned support arms exists, in a case where work spaces related to the support arms partially overlap, even in a situation in which a work within a safety movable range is guaranteed for each support arm by the dynamic update of a movement restriction range of each support arm, there is an unignorable possibility that collision caused by interference between support arms, or the like is caused.

For example, in the site of practice including a celiac operation, in some cases, a simultaneous operation of an endoscope device, forceps, and the like is performed, or a simultaneous operation of forceps is performed in a bimanual manner, for example. Furthermore, as a practice operation that uses a plurality of medical units in the site of practice, there are a number of cases in which a plurality of manipulators performs operations within the same work region, such as a combination of an operator operating forceps and a scopist operating an endoscope device, and a combination of an operator operating forceps and an assistant performing a suction operation. At this time, if an erroneous operation is performed, there is a possibility that an unexpected situation caused by the interference or collision between a plurality of medical units.

For the above-described reasons, for ensuring the safety in using a plurality of support arms, instead of depending only on the visual or tactile determination of a manipulator, security is required to be guaranteed by controlling a harmonized operation between the plurality of support arms on the device side, and performing operation restriction corresponding to the situation. For this reason, as one of characteristics, by acquiring information regarding a safety movable range related to another support arm (also referred to as a second medical support arm) used together with a support arm (also referred to as a first medical support arm) being a control target, the control device 20 according to the present embodiment controls a movement operation of the support arm being a control target, while performing harmonized control with the other support arm.

Figure 11A:
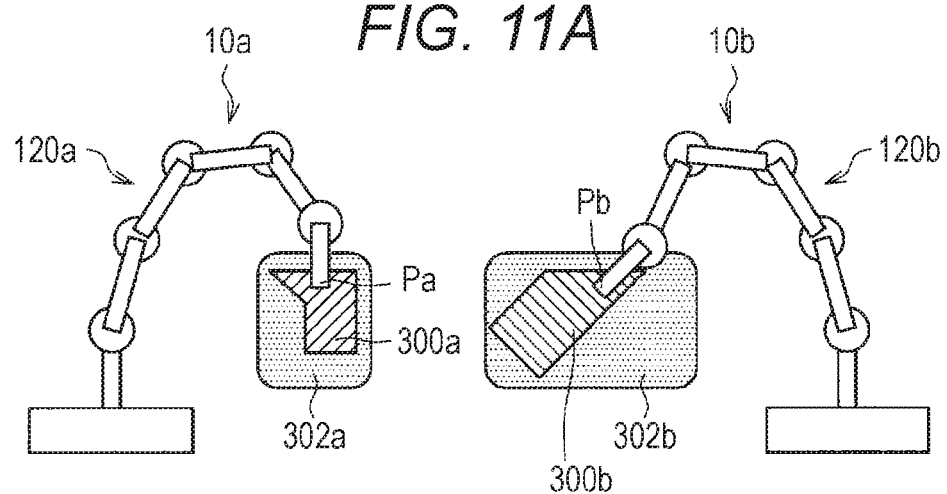
FIG. 11A is a diagram for describing a safety movable range of a plurality of support arms according to the embodiment.

FIG. 11A is a diagram for describing a safety movable range of a plurality of support arms according to the present embodiment. FIG. 11A illustrates two support arm devices 10a and 10b. Furthermore, FIG. 11A illustrates an arm distal end (the working point Pa) held by the support arm device 10a, a safety movable range 300a, an unsafe region 302a, an arm distal end (the working point Pb) held by the support arm device 10b, a safety movable range 300b, and an unsafe region 302b.

Here, in a case where the control device 20 controls a movement operation of the support arm device 10a, the control device 20 can control an operation of the working point Pa of the support arm device 10 on the basis of the safety movable range 300a of the support arm device 10a being a control target, the acquired safety movable range 300b of the support arm device 10b used together with the support arm device 10a, and a space position of the working point Pa.

More specifically, the control device 20 according to the present embodiment may control an operation of the working point Pa of the support arm device 10 on the basis of a region in which the safety movable range 300a of the support arm device 10a and the safety movable range 300b of the support arm device 10b overlap or abut, and the space position of the working point Pa.

At this time, as one of characteristics, the control device 20 according to the present embodiment controls an operation of the working point Pa on the basis of a set operation mode. Here, the above-described operation mode includes a movable range share mode, a collision avoidance mode, and a collision suppression mode.

Figure 11B:
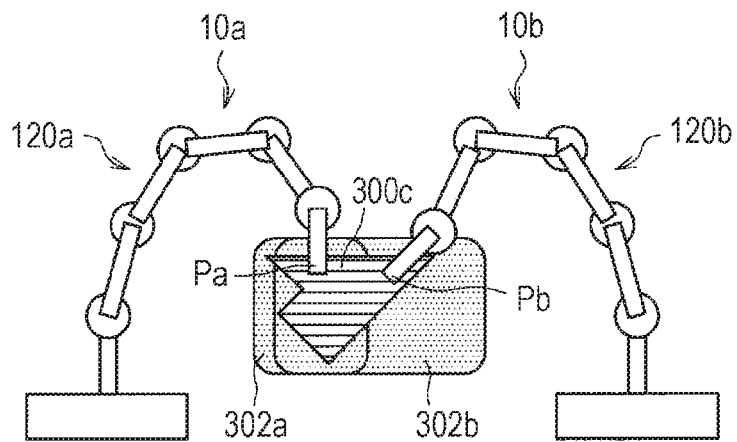
FIG. 11B is a diagram for describing an overview of a movable range share mode according to the embodiment.

First, the overview of the movable range share mode according to the present embodiment will be described. The movable range share mode according to the present embodiment defines a shared safety movable range obtained by adding safety movable ranges 300 related to a plurality of support arm devices 10, and is an operation mode in which the shared safety movable range is shared. FIG. 11B is a diagram for describing an overview of the movable range share mode according to the present embodiment. FIG. 11B illustrates, as a shared safety movable range 300c, a region obtained by adding the safety movable range 300a of the support arm device 10a and the safety movable range 300b of the support arm device 10b.

At this time, the control device 20 controls an operation of the working point Pa related to the support arm device 10a being a control target, on the basis of the shared safety movable range 300c. More specifically, the control device 20 can restrict an operation of the working point Pa in a case where the working point Pa related to the support arm device 10a enters an unsafe region over the shared safety movable range 300c. According to the movable range share mode according to the present embodiment, it is possible to share the safety movable range 300 guaranteed for each of the support arm devices 10, among a plurality of support arm devices 10, and it becomes possible to implement efficient movement control, and suppress collision with an external target object in the unsafe region 302.

Next, the overview of the collision avoidance mode according to the present embodiment will be described. The collision avoidance mode according to the present embodiment is a mode for preventing collision between a plurality of support arm devices 10. In the collision avoidance mode according to the present embodiment, the control device 20 can avoid collision with the other support arm device 10b used together, by controlling an operation of the support arm device 10a being a control target, on the basis of priorities set to a plurality of support arm devices 10.

Figure 11C:
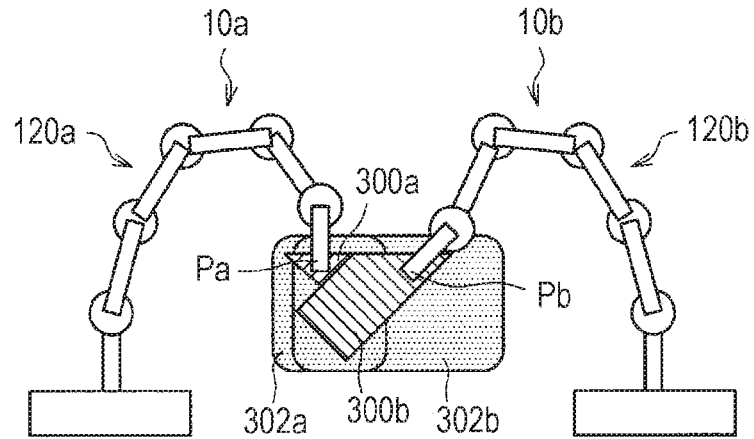
FIG. 11C is a diagram for describing an overview of a collision avoidance mode according to the embodiment.

FIG. 11C is a diagram for describing an overview of the collision avoidance mode according to the present embodiment. Note that FIG. 11C illustrates an example of a case where the priority of the support arm device 10a is lower than the priority of the support arm device 10b. FIG. 11C illustrates the safety movable range 300a of the support arm device 10a and the safety movable range 300b of the support arm device 10b, and it can be seen that the safety movable range 300a in FIG. 11C is reduced from the safety movable range 300a in FIG. 11A.

In this manner, in the collision avoidance mode according to the present embodiment, control is performed in such a manner that the safety movable range 300a related to the support arm device 10a having low priority is dynamically reduced on the basis of the safety movable range 300b of the support arm device 10b having high priority. Specifically, the control device 20 can define, as a new safety movable range 300a, a non-interference region obtained by subtracting a region overlapping the safety movable range 300b, in other words, an interference region of the support arm devices 10a and 10b, from the original safety movable range 300a. Furthermore, at this time, the control device 20 restricts an operation of the working point Pa to an avoidance movement to the above-described non-interference region in a case where the working point Pa of the support arm device 10a is positioned in the above-described interference region.

On the other hand, in a case where the control device 20 controls the support arm device 10b having high priority, the control device 20 may control an operation of the working point Pb in such a manner that an operation can be smoothly performed even in the above-described interference region. In other words, the control device 20 restricts an operation of the working point Pb only in a case where the working point Pb is positioned outside the safety movable range 300b.

According to the collision avoidance mode according to the present embodiment, the safety movable range 300 of the support arm device 10 having low priority is dynamically reduced in accordance with dynamic expansion of the safety movable range 300 of the support arm device 10 having high priority, and furthermore, control is performed in such a manner that an avoidance movement of the support arm device 10 having low priority to a non-interference region is performed. It thereby becomes possible to accurately prevent collision between the support arm devices 10.

Next, the overview of the collision suppression mode according to the present embodiment will be described. The collision suppression mode according to the present embodiment is a mode for suppressing colliding force exerted in collision between a plurality of support arm devices 10. In the collision suppression mode according to the present embodiment, the control device 20 can reduce colliding force in collision by restricting an operation of the working point P in an interference region between a plurality of support arm devices 10.

Figure 11D:
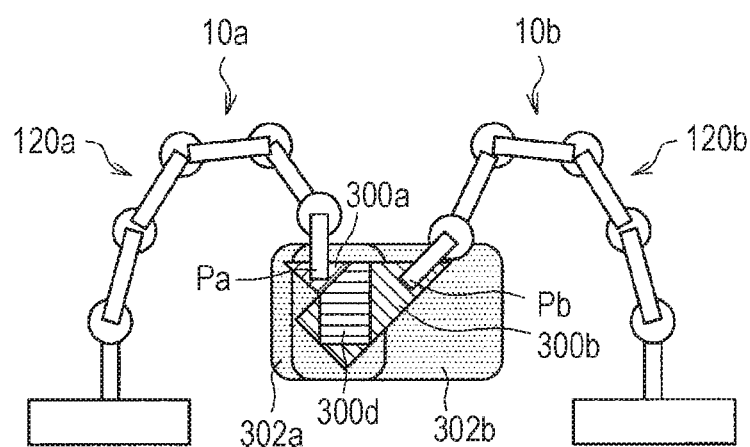
FIG. 11D is a diagram for describing an overview of a collision suppression mode according to the embodiment.

FIG. 11D is a diagram for describing an overview of the collision suppression mode according to the present embodiment. FIG. 11D illustrates, as an interference region 300d, a region in which the safety movable range 300a of the support arm device 10a and the safety movable range 300b of the support arm device 10b overlap.

At this time, by restricting an operation of the working point Pa of the support arm device 10a being a control target, in the interference region 300d, the control device 20 according to the present embodiment can suppress colliding force in collision with the working point Pb.

Heretofore, the overview of the harmonized control of a plurality of support arms according to the present embodiment has been described with reference to FIGS. 11A to 11D. Note that, in FIGS. 11A to 11D, an example of harmonized control performed in a case where two support arm devices 10a and 10b exist has been described, but the number of support arm devices 10 according to the present embodiment is not limited to that in the example. Furthermore, the support arm device 10 according to the present embodiment may include a plurality of arm portions 120. Also in this case, the control device 20 according to the present embodiment can implement harmonized control of the plurality of arm portions 120.

Furthermore, in an environment in which three or more support arm devices 10 exist, in a case where the control device 20 operates on the basis of the collision avoidance mode, priorities of the support arm devices 10 can be flexibly set. For example, the priorities may be in such a manner that the support arm device 10a>the support arm device 10b=the support arm device 10c, or may be in such a manner that the support arm device 10a>the support arm device 10b>the support arm device 10c. In any case of the above-described cases, the control device 20 according to the present embodiment can appropriately control an operation of the support arm device 10 being a control target on the basis of a relationship between priorities of the other support arm devices 10 to be used together.

Moreover, in an environment in which three or more support arm devices 10 exist, two or more modes may be set in a mixed manner. For example, the movable range share mode may be set between the support arm devices 10a and 10b, and the collision suppression mode may be set between the support arm devices 10a and 10c. At this time, the control device 20 that uses the support arm device 10a as a control target can perform operation control of the support arm device 10*a* on the basis of an operation mode related to the other support arm devices 10*b* and 10*c* to be used together.

Furthermore, an operation mode according to the present embodiment can also be dynamically set on the basis of a characteristic or the like of a distal end unit or practice. For example, in a case where a distal end unit is a sharp unit such as forceps, the collision avoidance mode may be automatically set. At this time, the above-described distal end unit can be identified by, for example, reading of an ID, image recognition, or the like. In this manner, operation control performed by the control device 20 according to the present embodiment can perform flexible expansion.

<<2-7. Configuration Example for Implementing Harmonized Control of Plurality of Support Arms>>

Figure 12:
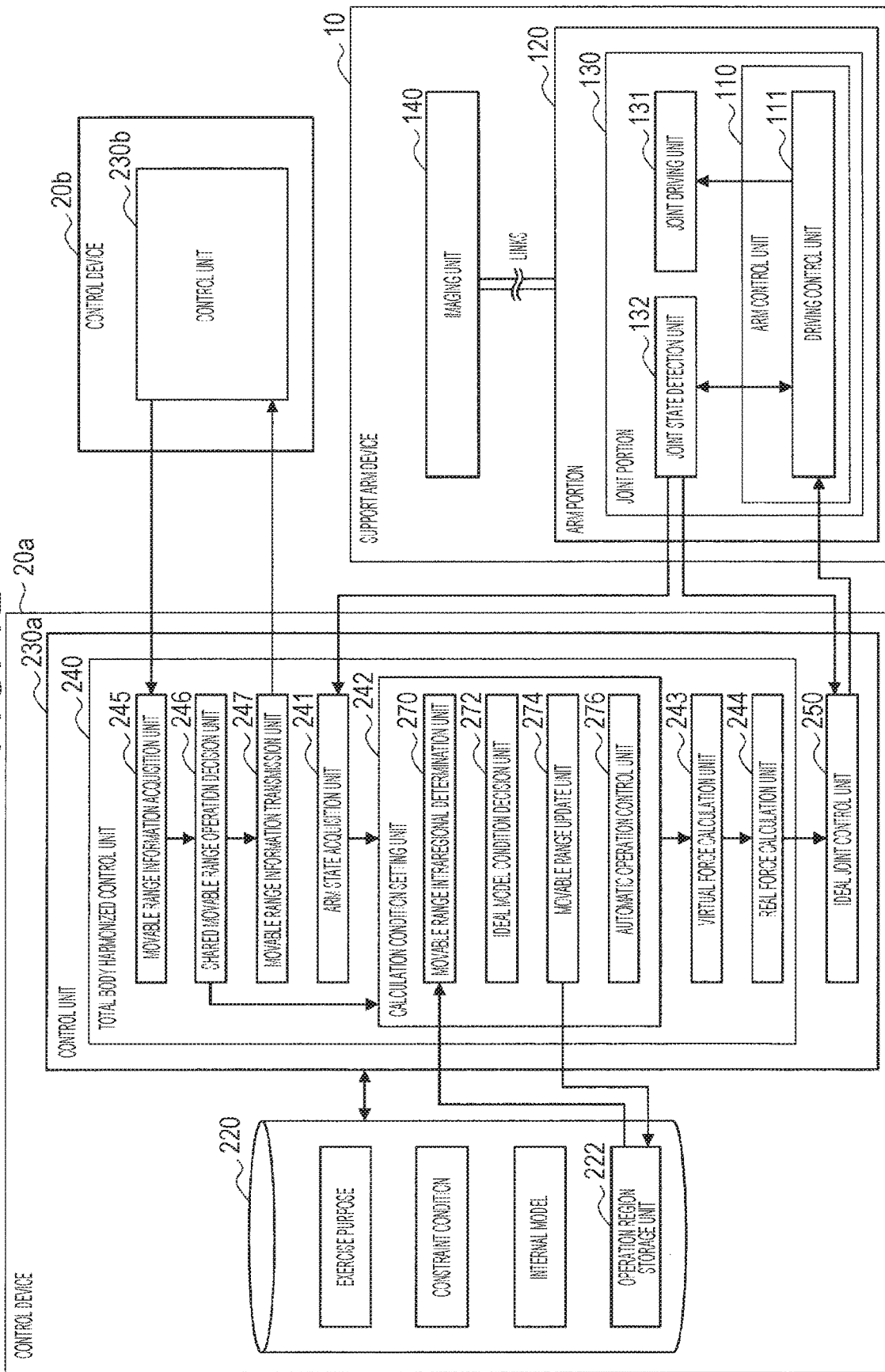
FIG. 12 is a schematic diagram illustrating a configuration example for implementing harmonized control of a plurality of support arms according to the embodiment.

FIG. 12 is a schematic diagram illustrating a configuration example for implementing harmonized control of a plurality of support arms, and in the schematic diagram illustrated in FIG. 12, in the control unit 230 illustrated in FIG. 8, a movable range information acquisition unit 245, a shared movable range operation decision unit 246, a movable range information transmission unit 247, a movable range intraregional determination unit 270, an ideal model condition decision unit (operation control unit) 272, and a movable range update unit 274 are added. Among these units, the movable range information acquisition unit 245, the shared movable range operation decision unit 246, and the movable range information transmission unit 247 are included in the total body harmonized control unit 240. Furthermore, the movable range intraregional determination unit 270, the ideal model condition decision unit 272, and the movable range update unit 274 are included in the calculation condition setting unit 242.

Furthermore, in the storage unit 220 illustrated in FIG. 8, an operation region storage unit 222 is added. Region information regarding the safety movable range 300 in which working points related to the support arm device 10 being a control target, and the other support arm device 10 to be used together are operable, and the unsafe region 302 is stored in the operation region storage unit 222. The region information is boundary information indicating a boundary between the safety movable range 300 and the unsafe region 302, and includes information indicating a three-dimensional boundary surface.

The movable range information acquisition unit 245 acquires information regarding the safety movable range 300, from a control unit 230*b* that controls the other support arm device 10 to be used together with the support arm device 10 being a control target. At this time, the movable range information acquisition unit 245 may acquire information regarding the safety movable range 300, from the control unit 230*b* included in another control device 20*b* as illustrated in the drawing, or may acquire information regarding the safety movable range 300, from another control unit 230*b* included in a control device 20*a*. Furthermore, the movable range information acquisition unit 245 may acquire information regarding the safety movable range 300, from a plurality of other control units 230.

The shared movable range operation decision unit 246 sets a shared movable range, an interference region, a non-interference region, or the like according to the present embodiment on the basis of a set operation mode, and outputs information regarding the region, to the movable range update unit 274. The movable range update unit 274 updates movable range information saved in the operation region storage unit 222, on the basis of information input from the shared movable range operation decision unit 246.

In the arm state acquisition unit (position acquisition unit) 241, positions on the space of a link and an arm distal end are calculated on the basis of the current arm state acquired from the arm portion 120, and arm information acquired from the storage unit 220.

The movable range intraregional determination unit 270 compares the position on the space of the working point P (arm distal end) acquired by the arm state acquisition unit 241, and region information of the safety movable range 300 stored in the operation region storage unit 222, and determines whether the arm distal end exists in the safety movable range 300, or the arm distal end exists in the unsafe region 302. Furthermore, the movable range intraregional determination unit 270 determines whether or not the position on the space of the working point P (arm distal end) is positioned in the shared movable range, the interference region, or the non-interference region, on the basis of the set operation mode. A determination result obtained by the movable range intraregional determination unit 270 is sent to the ideal model condition decision unit 272. Note that, here, the working point P is assumed to be an arm distal end, but the working point P may be an arbitrary point on the arm portion 120, such as the joint portion 130.

On the basis of the determination result obtained by the movable range intraregional determination unit 270, in cooperation with the total body harmonized control unit 240, the ideal model condition decision unit 272 adjusts a control parameter and permits motions of the arm distal end within the safety movable range 300 in a case where the arm distal end exists within the safety movable range 300, and restricts motions of the arm distal end in a case where the arm distal end enters the unsafe region 302 over a boundary between the safety movable range 300 and the unsafe region 302. Furthermore, the ideal model condition decision unit 272 executes operation control corresponding to the set operation mode. The operation control corresponding to the operation mode according to the present embodiment will be separately described later.

Note that, as an example of a control parameter, there is a viscous resistance coefficient. As mentioned above, when an exercise purpose is set, a viscous resistance coefficient in a rotational movement of each of the joint portions 130 can be appropriately set. By adjusting a viscous resistance coefficient of each of the joint portions 130 in accordance with a position of the arm distal end, in a case where the arm distal end is positioned within the safety movable range 300, a viscous resistance coefficient is lowered and a free motion of the arm is permitted, and in a case where the arm distal end enters the unsafe region 302, the arm distal end can be prevented from entering the unsafe region 302 by setting a higher viscous resistance coefficient.

Furthermore, as mentioned above, an exercise purpose may be various types of information regarding the movement of the arm portion 120, and may be a speed of the arm distal end. By using a speed of the arm distal end as a control parameter, and adjusting the speed of the arm distal end in accordance with the position of the arm distal end, in a case where the arm distal end is positioned within the safety movable range 300, a relatively high speed is permitted and a free motion of the arm is permitted, and in a case where the arm distal end enters the unsafe region 302, the arm distal end can be prevented from entering the unsafe region 302 by restricting the speed of the arm distal end.

The control parameter set by the calculation condition setting unit 242 is sent to the virtual force calculation unit 243 as an exercise purpose and a constraint condition as mentioned above, and processing similar to the above-described processing is performed. With this configuration, a control parameter is used as a parameter for ideal joint control calculation in the ideal joint control unit 250 and the driving control unit 111 of the support arm device 10, and a movement operation of an arm distal end portion is restricted in a new entry region to the unsafe region 302 over the safety movable range 300. Note that internal model information including a viscous load amount in each region is stored in the storage unit 220.

Furthermore, concurrently with the above control, position information of the arm distal end obtained in a case where the movable range intraregional determination unit 270 determines that the arm distal end exists outside the safety movable range 300 is sent to the movable range update unit 274, and in a case where it is determined that movable range expansion is unnecessary, region information regarding the safety movable range 300 in the operation region storage unit 222 is updated by the movable range update unit 274. The safety movable range 300 is thereby dynamically changed in real time during the arm operation.

In this manner, on the basis of the determination result obtained by the movable range intraregional determination unit 270, in a case where the arm distal end enters the unsafe region 302 over the boundary between the safety movable range 300 and the unsafe region 302, the movable range update unit 274 expands the safety movable range 300, and updates region information regarding the safety movable range 300. Furthermore, in a case where an operation mode is the collision avoidance mode, the movable range update unit 274 dynamically reduces the safety movable range 300 of the support arm device 10 being a control target, on the basis of the safety movable range 300 of the other support arm device 10 having high priority.

Information regarding the safety movable range 300 of the support arm device 10 being a control target that has been updated by the movable range update unit 274 is transmitted to the other control unit 230*b* by the movable range information transmission unit 247.

By the above configuration, it is possible to implement an operation that is based on the manual guide operation mode as illustrated in FIGS. 9A to 9C, and harmonized control of a plurality of support arm devices 10 as illustrated in FIGS. 11A to 11D.

In the automatic operation mode illustrated in FIGS. 10A to 10C, by using region information regarding the safety movable range 300 that is stored in the operation region storage unit 222, as a constraint condition in the calculation condition setting unit 242, only the safety movable range 300 prestored in the manual guide operation mode can be set as a physical movable range (virtual wall) of the automatic operation mode. With this configuration, it is possible to suppress a movement operation to the outside of the safety movable range 300, and by limiting an operation to an automatic operation only within the safety movable range 300 in which safety has already been confirmed, it becomes possible to secure safety. The automatic operation is executed by an automatic operation control unit 276 on the basis of position information, a speed, or the like for the automatic operation that is stored in the storage unit 220. Furthermore, the automatic operation control unit 276 controls an automatic avoidance operation of the working point P to the non-interference region in the collision avoidance mode.

Note that each operation mode is stored in the storage unit 220 of the control device 20, and can be switched by a manipulator at an arbitrary timing. Furthermore, as mentioned above, an operation mode according to the present embodiment may be automatically controlled.

Note that, in the aforementioned example, the arm distal end is exemplified as the working point P, but the working point P can be set to one or a plurality of arbitrary points on the arm portion 120, and for example, may be set to one or a plurality of joint portions 130 or one or a plurality of links. Furthermore, the working point P may be set to both of an arm distal end and the joint portion 130 (or link). In a case where a plurality of working points P is set, motions of the entire arm portion 120 are permitted or restricted on the basis of the safety movable range 300 set for each of the working points P, and region information regarding the unsafe region 302.

Heretofore, a configuration example for implementing harmonized control of a plurality of support arms has been described. Note that the configuration illustrated in FIG. 12 is merely an example, and the configuration of the control device 20 according to the present embodiment is not limited to this example. For example, functions included in the control device 20 according to the present embodiment may be implemented by a plurality of devices in a dispersed manner. As an example, the arm state acquisition unit 241 according to the present embodiment can be provided on the outside of the control device 20. In this case, the control device 20 according to the present embodiment can acquire information regarding space positions of working points of a plurality of arms, from a plurality of arm state acquisition units 241 existing on the outside, and perform control of the plurality of arms. At this time, the control device 20 according to the present embodiment may operate as a part of an operating room integrative system in which a plurality of different medical devices is networked, for example. The configuration of the control device 20 according to the present embodiment can be flexibly expanded.

<<2-8. Flow of Control>>

Figure 13:
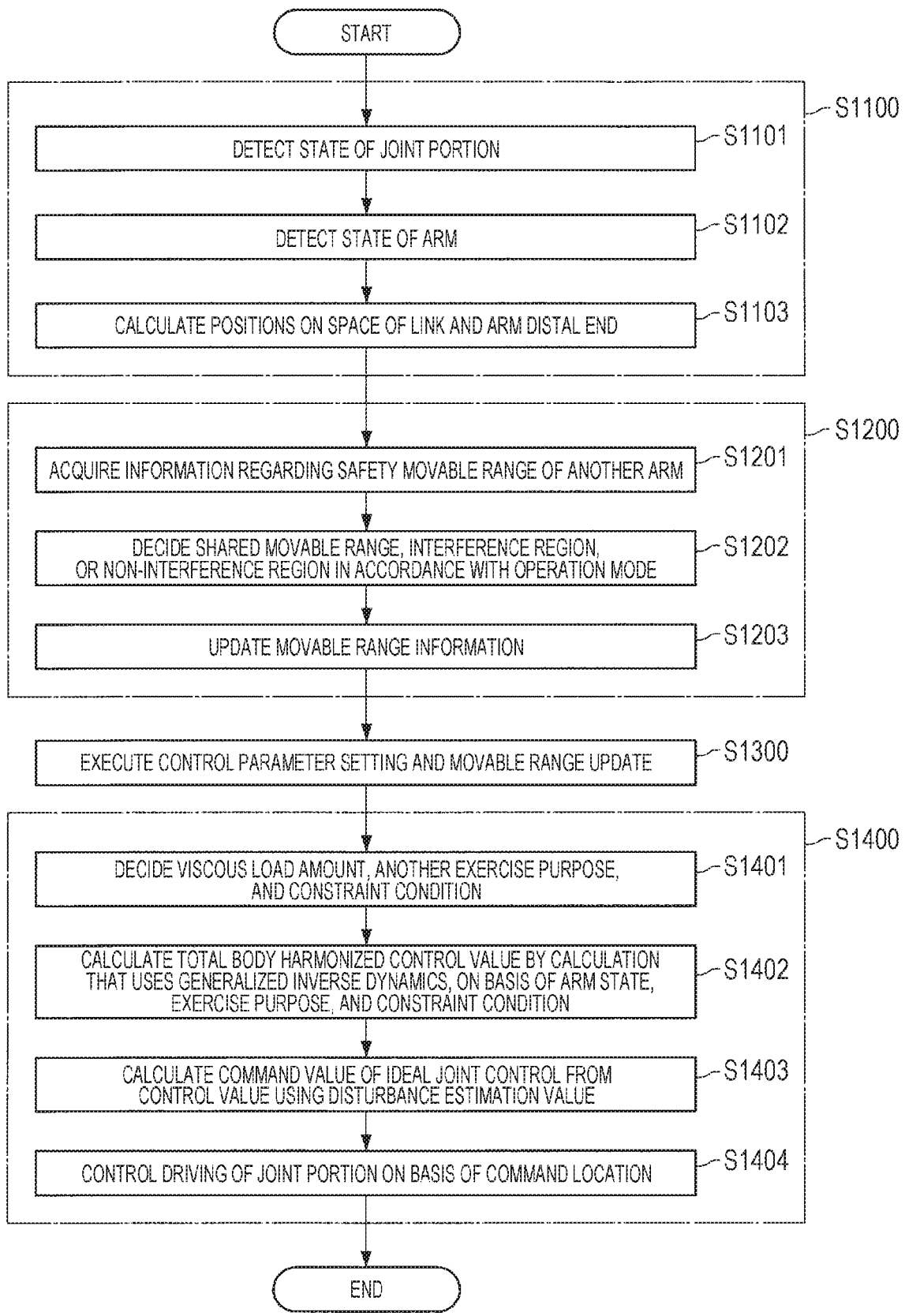
FIG. 13 is a flowchart illustrating a basic flow of control performed by a control device 20 according to the embodiment.

Next, a flow of harmonized control of a plurality of support arms that is performed by the control device 20 according to the present embodiment will be described. First, a basic flow of the control performed by the control device 20 according to the present embodiment will be described. FIG. 13 is a flowchart illustrating a basic flow of control performed by the control device 20 according to the present embodiment. Referring to FIG. 13, the control device 20 according to the present embodiment is broadly-divided into four: calculation of a working point position (S1100), calculation of a movable range (S1200), setting of a control parameter and movable range update (S1300) that are based on an operation mode, and control calculation and operation control (S1400).

In the calculation of a working point position (S1100), the control device 20 first detects the state of the joint portion 130 (S1101). Next, the control device 20 acquires the state of the arm portion 120 (S1102). Next, the control device 20 calculates a position on the space of the working point (here, link and arm distal end) (S1103).

Subsequently, in the calculation of a movable range (S1200), the control device 20 acquires information regarding a safety movable range of another arm (S1201). At this time, the movable range information acquisition unit 245 of the control device 20 may acquire, from a plurality of control units 230 that controls the other support arm devices 10, information regarding safety movable ranges of a plurality of the other support arm devices 10. Next, the movable range update unit 274 of the control device 20 decides a shared movable range, an interference region, a non-interference region, or the like in accordance with an operation mode (S1202). Furthermore, the movable range update unit 274 updates movable range information saved in the operation region storage unit 222, on the basis of information input from the shared movable range operation decision unit 246 (S1203).

Subsequently, the control device 20 executes the setting of a control parameter and the update of a movable range that are based on a set operation mode (S1300). A flow of control that is based on an operation mode in step S1300 will be separately described in detail.

Subsequently, in the control calculation and operation control (S1400), the control device 20 decides a viscous load amount, another exercise purpose, and a constraint condition (S1401). Next, the control device 20 calculates a total body harmonized control value by calculation that uses the generalized inverse dynamics, on the basis of an arm state, an exercise purpose, and a constraint condition (S1402). Next, the control device 20 calculates a command value of ideal joint control from the total body harmonized control value using a disturbance estimation value (S1403). Next, the control device 20 controls the driving of the joint portion 130 on the basis of the command value of the ideal joint control (S1404).

Subsequently, a flow of the setting of a control parameter and update of a movable range that are based on an operation mode in step S1300 illustrated in FIG. 13 will be described in detail.

Figure 14:
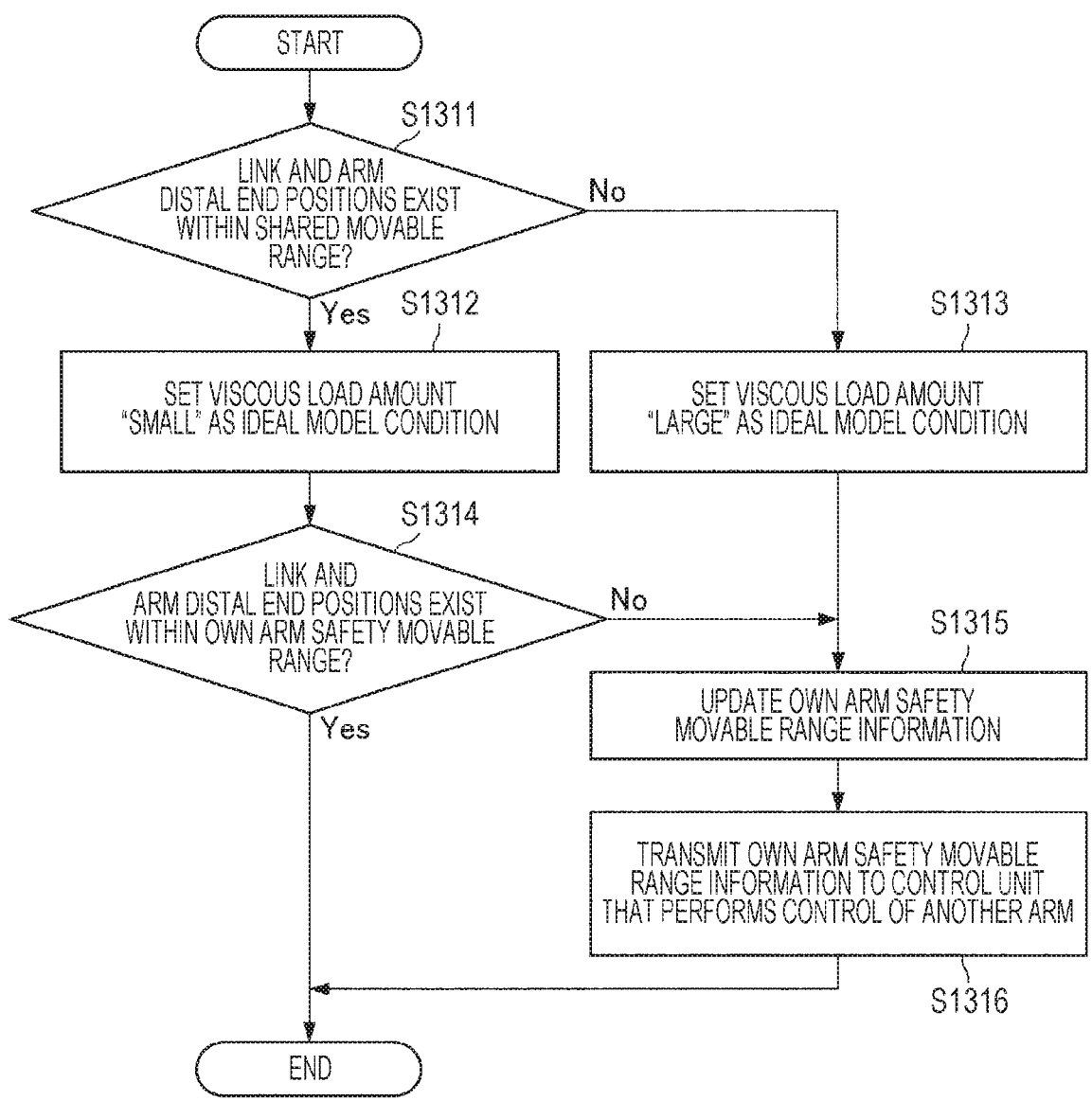
FIG. 14 is a flowchart illustrating a flow of setting of a control parameter and update of a movable range in a movable range share mode according to the embodiment.

First, a flow of an operation of the control device 20 in a case where an operation mode is the movable range share mode will be described. FIG. 14 is a flowchart illustrating a flow of setting of a control parameter and update of a movable range in the movable range share mode according to the present embodiment.

Referring to FIG. 14, first, the movable range intraregional determination unit 270 determines whether or not working points acquired by the arm state acquisition unit 241, in other words, space positions of the arm distal end and a link exist within the shared movable range decided by the shared movable range operation decision unit 246 (S1311).

Here, in a case where the space positions of the working points do not exist within the shared movable range (S1311: No), the ideal model condition decision unit 272 sets a viscous load amount (viscous resistance coefficient) "large" as an ideal model condition (S1313). With this configuration, colliding force with an external target object on the outside of the shared movable range is suppressed.

On the other hand, in a case where the space positions of the working points exist within the shared movable range (S1311: Yes), the ideal model condition decision unit 272 sets a viscous load amount (viscous resistance coefficient) "small" as an ideal model condition (S1312). With this configuration, smooth motions of the working points, in other words, the arm distal end and the link are permitted within the shared movable range.

Furthermore, in a case where the working points exist within the shared movable range (S1311: Yes), the movable range intraregional determination unit 270 determines whether or not space positions of the working points exist within a safety movable range of an own arm, in other words, the support arm device 10 being a control target (S1314).

Here, in a case where the working points do not exist within the safety movable range of the own arm (S1314: No), or in a case where the working points do not exist within the shared movable range (S1311: No), the movable range update unit 274 expands the safety movable range of the own arm as necessary, and updates information held in the operation region storage unit 222 (S1315).

Subsequently, the movable range information transmission unit 247 transmits information regarding the safety movable range of the own arm that has been updated in step S1315, to a control unit that performs control of another arm (S1316).

Figure 15:
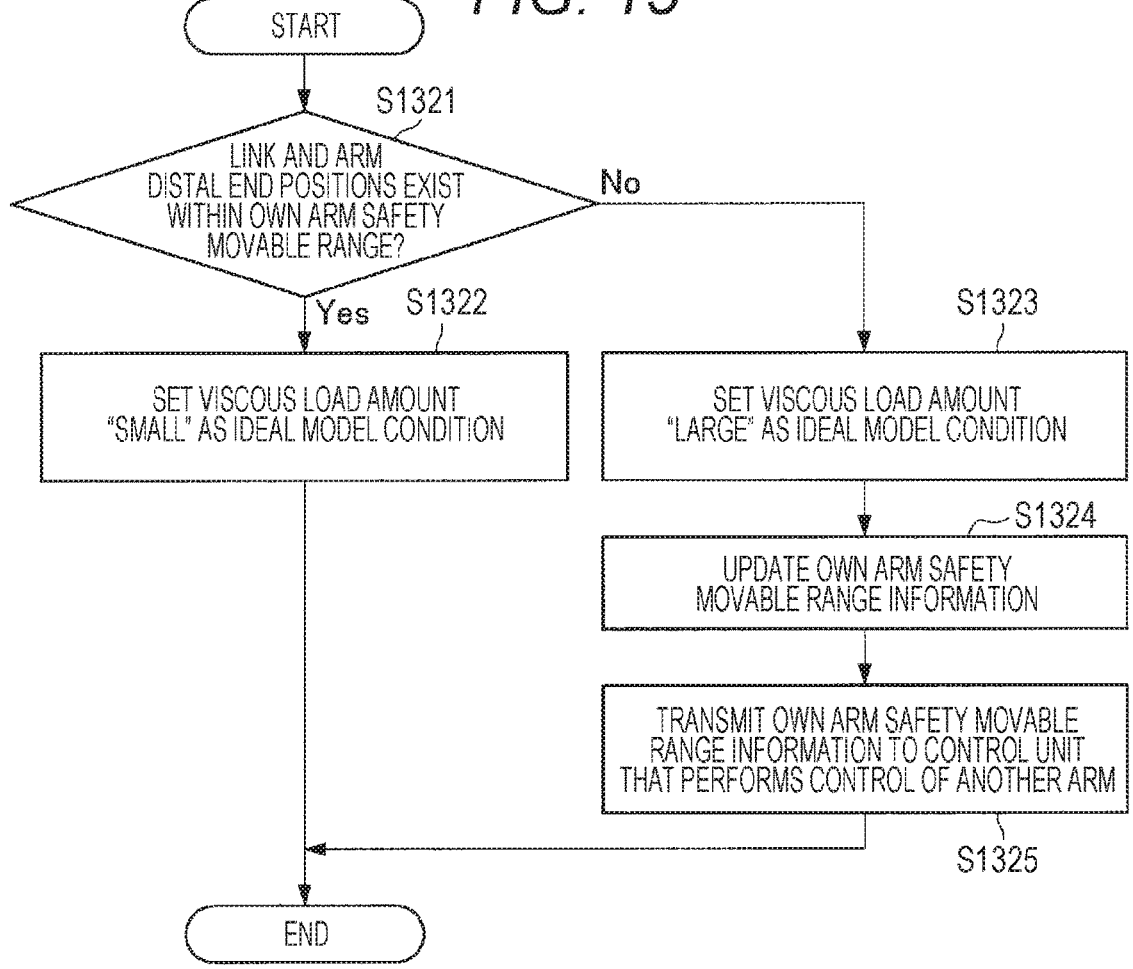
FIG. 15 is a flowchart illustrating a flow of setting of a control parameter and update of a movable range in a case where priority of an own arm is high in the collision avoidance mode according to the embodiment.

Next, a flow of an operation of the control device 20 in a case where an operation mode is the collision avoidance mode and the priority of the own arm is higher than the priority of another arm will be described. FIG. 15 is a flowchart illustrating a flow of setting of a control parameter and update of a movable range in a case where priority of an own arm is high in the collision avoidance mode according to the present embodiment.

Referring to FIG. 15, first, the movable range intraregional determination unit 270 determines whether or not space positions of working points acquired by the arm state acquisition unit 241 exist within the safety movable range of the own arm (S1321).

Here, in a case where the space positions of the working points exist within the safety movable range of the own arm (S1321: Yes), the ideal model condition decision unit 272 sets a viscous load amount (viscous resistance coefficient) "small" as an ideal model condition (S1322). With this configuration, smooth motions of the arm distal end and the link are permitted within the safety movable range of the own arm.

On the other hand, in a case where the space positions of the working points do not exist within the safety movable range of the own arm (S1321: No), the ideal model condition decision unit 272 sets a viscous load amount (viscous resistance coefficient) "large" as an ideal model condition (S1323). With this configuration, colliding force with an external target object on the outside of the safety movable range of the own arm is suppressed.

Next, the movable range update unit 274 expands the safety movable range of the own arm as necessary, and updates information held in the operation region storage unit 222 (S1324).

Subsequently, the movable range information transmission unit 247 transmits information regarding the safety movable range of the own arm that has been updated in step S1324, to a control unit that performs control of another arm (S1325).

Figure 16:
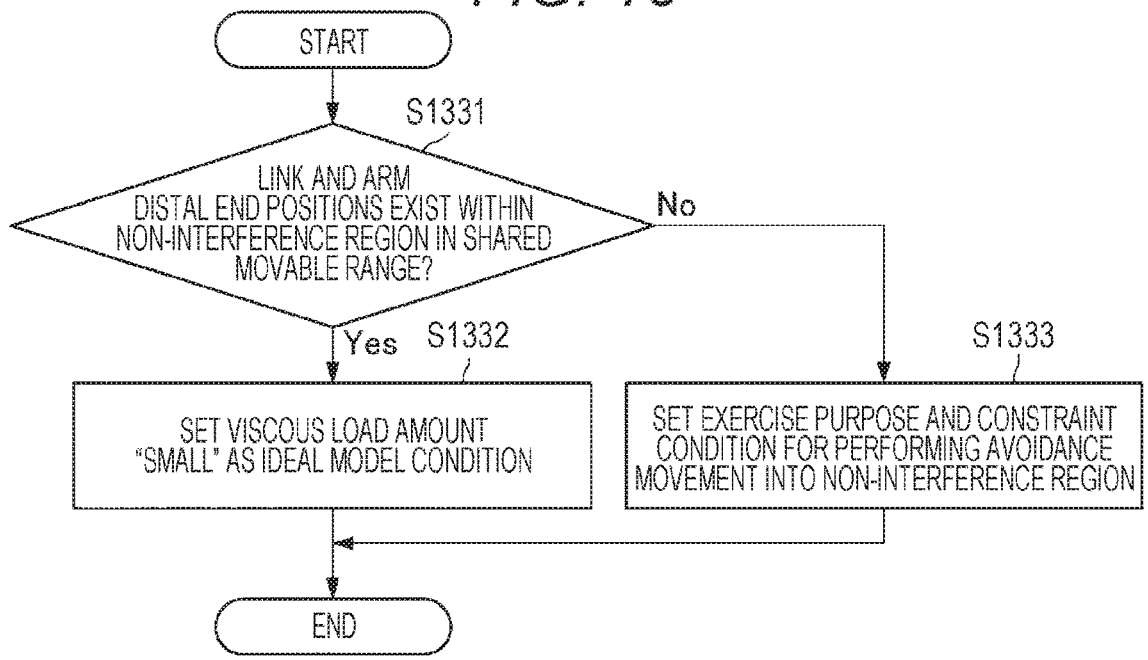
FIG. 16 is a flowchart illustrating a flow of setting of a control parameter and update of a movable range in a case where priority of an own arm is low in the collision avoidance mode according to the embodiment.

Next, a flow of an operation of the control device 20 in a case where an operation mode is the collision avoidance mode and the priority of the own arm is lower than the priority of another arm will be described. FIG. 16 is a flowchart illustrating a flow of setting of a control parameter and update of a movable range in a case where priority of an own arm is low in the collision avoidance mode according to the present embodiment.

Referring to FIG. 16, first, the movable range intraregional determination unit 270 determines whether or not space positions of working points acquired by the arm state acquisition unit 241 exist within the non-interference region (S1331).

Here, in a case where the space positions of the working points exist within the non-interference region (S1331: Yes), the ideal model condition decision unit 272 sets a viscous load amount (viscous resistance coefficient) "small" as an ideal model condition (S1332). With this configuration, smooth motions of the arm distal end and the link are permitted within the non-interference region.

On the other hand, in a case where the space positions of the working points do not exist within the non-interference region (S1331: No), the ideal model condition decision unit 272 sets an exercise purpose and a constraint condition for performing an avoidance movement of the working points to the non-interference region (S1333). With this configuration, it becomes possible to implement harmonized control of accurately avoiding collision with another arm having high priority.

Figure 17:
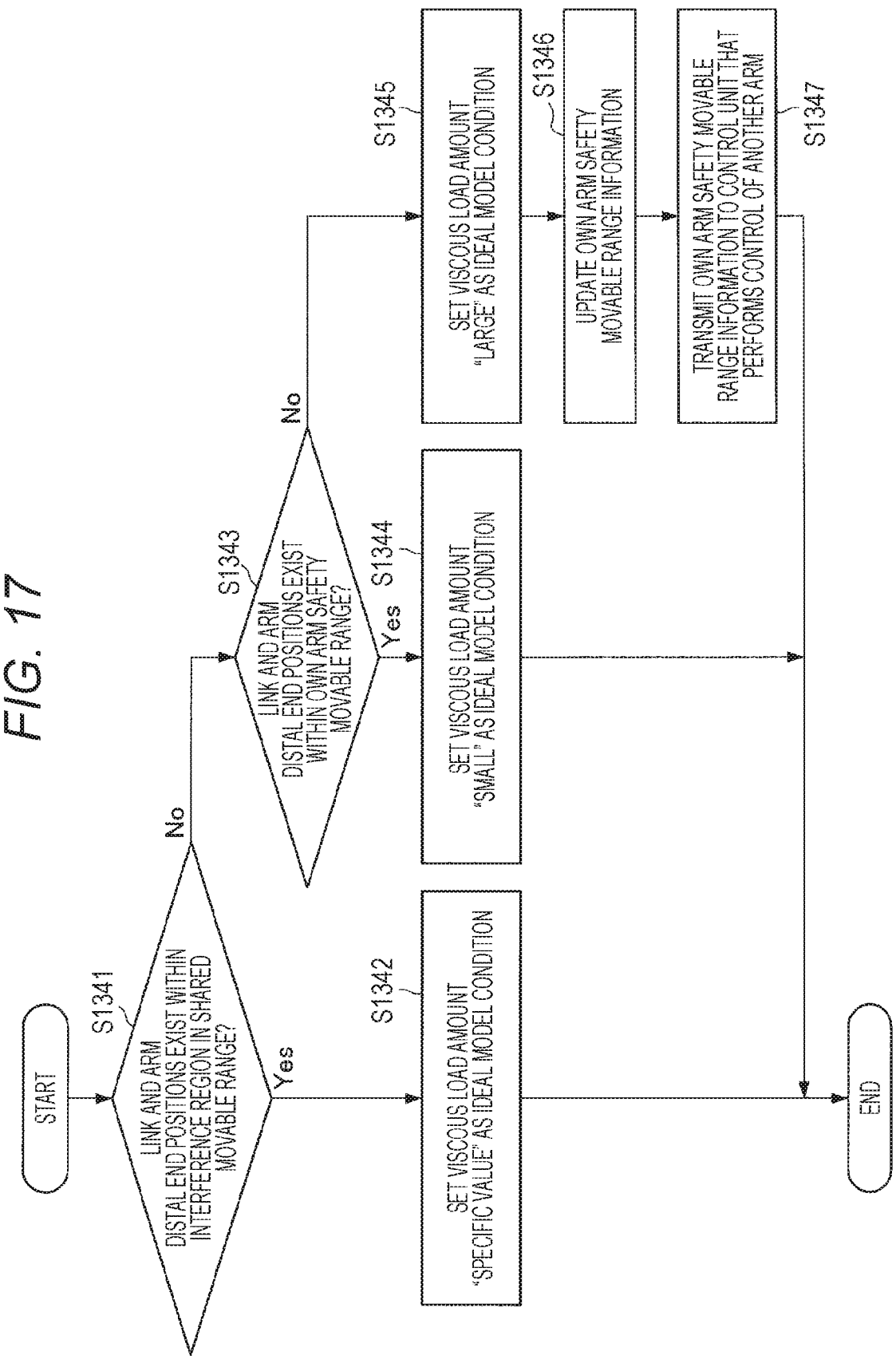
FIG. 17 is a flowchart illustrating a flow of setting of a control parameter and update of a movable range in the collision suppression mode according to the embodiment.

Next, a flow of an operation of the control device 20 in a case where an operation mode is the collision suppression mode will be described. FIG. 17 is a flowchart illustrating a flow of setting of a control parameter and update of a movable range in the collision suppression mode according to the present embodiment.

Referring to FIG. 17, first, the movable range intraregional determination unit 270 determines whether or not space positions of working points acquired by the arm state acquisition unit 241 exist within the interference region decided by the shared movable range operation decision unit 246 (S1341).

Here, in a case where the space positions of the working points exist within the interference region (S1341: Yes), the ideal model condition decision unit 272 sets a viscous load amount (viscous resistance coefficient) "specific value" as an ideal model condition (S1342). With this configuration, it becomes possible to implement operation control of suppressing colliding force in collision between distal end units in the interference region.

On the other hand, in a case where the space positions of the working points do not exist within the interference region (S1341: No), subsequently, the movable range intraregional determination unit 270 determines whether or not the space positions of the working points exist within the safety movable range of the own arm (S1343).

Here, in a case where the space positions of the working points exist within the safety movable range of the own arm (S1343: Yes), the ideal model condition decision unit 272 sets a viscous load amount (viscous resistance coefficient) "small" as an ideal model condition (S1344). With this configuration, smooth motions of the arm distal end and the link are permitted within the safety movable range of the own arm.

On the other hand, in a case where the space positions of the working points do not exist within the safety movable range of the own arm (S1343: No), the ideal model condition decision unit 272 sets a viscous load amount (viscous resistance coefficient) "large" as an ideal model condition (S1345). With this configuration, colliding force with an external target object on the outside of the safety movable range of the own arm is suppressed.

Next, the movable range update unit 274 expands the safety movable range of the own arm as necessary, and updates information held in the operation region storage unit 222 (S1346).

Subsequently, the movable range information transmission unit 247 transmits information regarding the safety movable range of the own arm that has been updated in step S1346, to a control unit that performs control of another arm (S1347).

Heretofore, a flow of harmonized control of a plurality of support arms that is performed by the control device 20 according to the present embodiment has been described in detail. In this manner, according to the control device 20 according to the present embodiment, the safety is ensured by suppressing a rapid movement to the outside of a safety movable range that is caused by an erroneous operation or the like, and at the same time, by storing a once-passed space position as a safety movable range, in a region in which safety has already been guaranteed, it becomes possible for a manipulator to freely operate an arm.

Furthermore, according to the control device 20 according to the present embodiment, it is possible to perform a fine operation only in a case where an arm enters an unreached region, and it becomes possible to implement an arm operation flexibly corresponding to an environment change caused by the progress in practice.

Furthermore, according to the control device 20 according to the present embodiment, by presenting a safety movable range updated in real time, to the user, a practitioner can perform an operation while recognizing a safety movable range corresponding to the current situation, and it becomes possible to advance the practice while efficiently expanding an operative region with the safety being maintained.

Furthermore, according to the control device 20 according to the present embodiment, even in a case where practice that uses a plurality of arms is performed, by sharing information regarding a safety movable range in a work space, with each other, it becomes possible to advance the practice safely and efficiently.

Furthermore, according to the collision avoidance mode of the control device 20 according to the present embodiment, when an avoidance movement of a working point is performed by dynamic update of a movable range, it becomes possible to simultaneously avoid collision with an obstacle other than another arm, and it becomes possible to progress practice more safely.

Furthermore, according to the collision suppression mode of the control device 20 according to the present embodiment, it is possible to continue practice without performing movable range update, it is possible to reduce impact in collision between a plurality of arms, and it becomes possible to progress practice safely.

<<2-9. Variations of Safety Movable Range and Unsafe Region>

Figure 18:
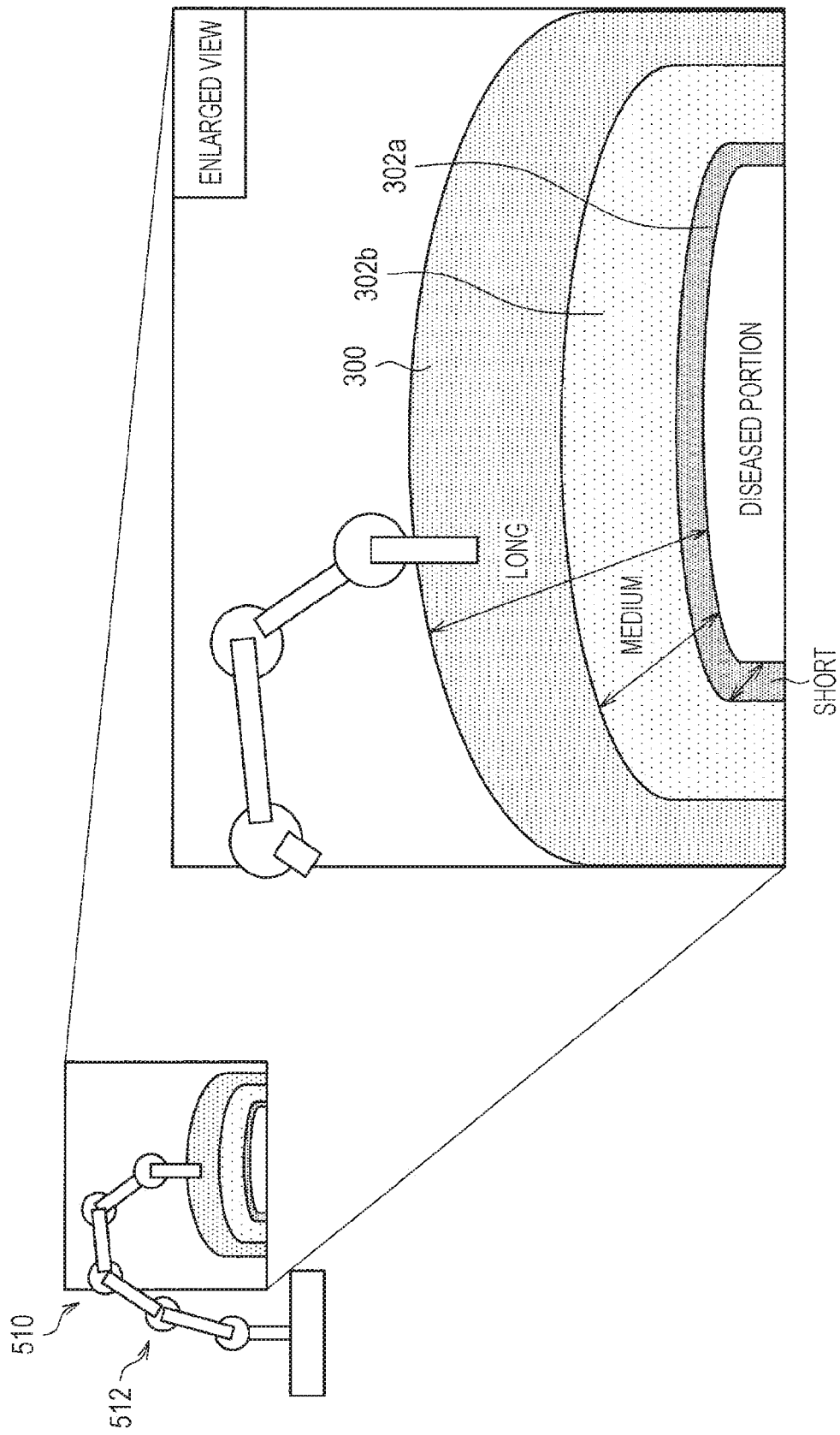
FIG. 18 is a schematic diagram illustrating an example in which a safety movable range and an unsafe region are set in a stepwise manner in accordance with a distance from a diseased portion.

Hereinafter, variations of a safety movable range and an unsafe region will be described. FIG. 18 is a schematic diagram illustrating an example in which the safety movable range 300 and the unsafe region 302 are set in a stepwise manner in accordance with a distance from a diseased portion. As illustrated in FIG. 18, a region closest to the diseased portion is set as an unsafe region 302a having an unsafe level "high". Furthermore, an unsafe region 302b having an unsafe level "medium" is set on the outside of the unsafe region 302a.

Furthermore, the safety movable range 300 is set on the outside of the unsafe region 302b. In this manner, by providing the unsafe regions 302a and 302b in a stepwise manner so as to have different unsafe levels in accordance with distances from the diseased portion, it is possible to surely prevent an arm distal end from contacting the diseased portion by differentiating a control parameter (viscous resistance coefficient, speed, etc.) for each region.

Figure 19:
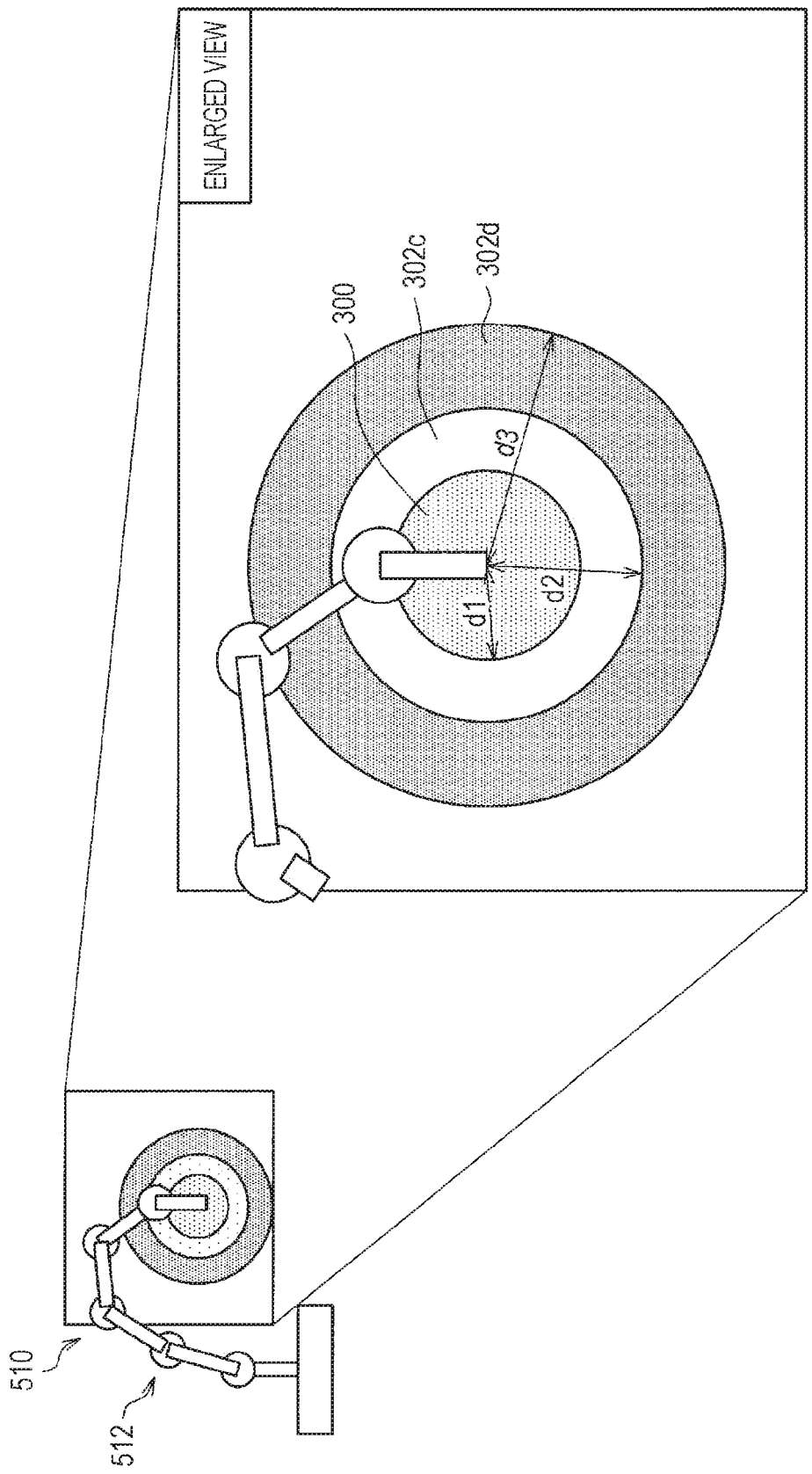
FIG. 19 is a schematic diagram illustrating an example in which a safety movable range is set in a stepwise manner in accordance with a distance from an arm distal end position at startup.

FIG. 19 is a schematic diagram illustrating an example in which the safety movable range 300 is set in a stepwise manner in accordance with a distance from an arm distal end position at startup. As illustrated in FIG. 19, a range having a distance d1 from the arm distal end position at startup is set as the safety movable range 300. Furthermore, a range having a distance d2 from the arm distal end position at startup is set as an unsafe region 302c, and a range having a distance d3 from the arm distal end position at startup is set as an unsafe region 302d. With this configuration, it is possible to set the safety movable range 300 and the unsafe region 302 in a default state at startup. The safety movable range 300 set in the default state can be appropriately expanded by performing an expansion operation as illustrated in FIGS. 9A to 9C.

Figure 20:
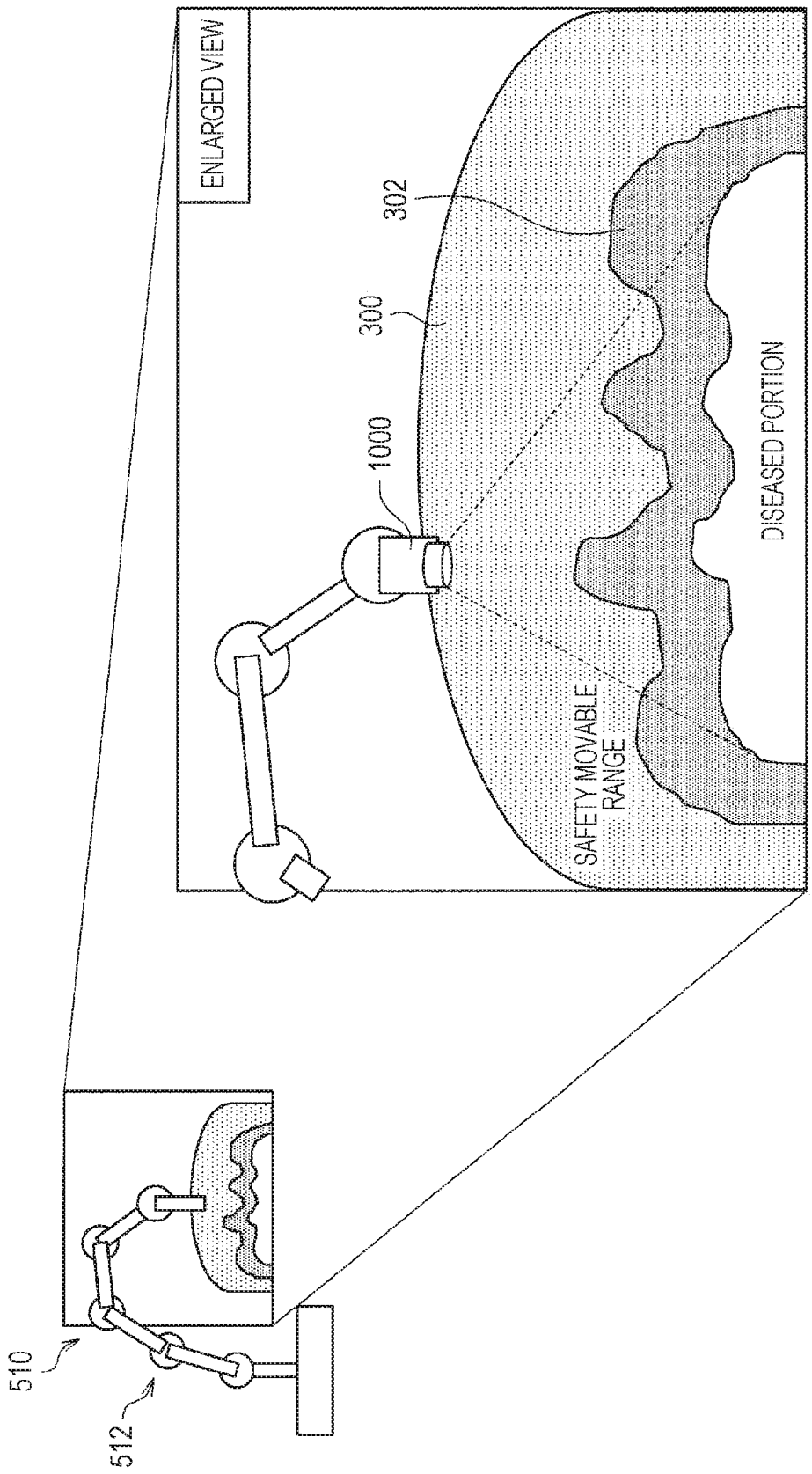
FIG. 20 is a schematic diagram illustrating an example in which a 3D camera is mounted at an arm distal end, a three-dimensional shape of a diseased portion is measured by image recognition that uses an image captured by the 3D camera, a depth map is created, and an unsafe region is set on the basis of the shape of the diseased portion that is obtained by the depth map.

FIG. 20 is a schematic diagram illustrating an example in which a 3D camera 1000 is mounted at an arm distal end, a three-dimensional shape of a diseased portion is measured by image recognition that uses an image captured by the 3D camera 1000, a depth map is created, and an unsafe region 302 is set on the basis of the shape of the diseased portion that is obtained by the depth map. The safety movable range 300 is set on a side closer to the arm distal end side than the unsafe region 302. By setting the unsafe region 302 on the basis of the depth map, it is possible to move the arm distal end to a boundary between the safety movable range 300 and the unsafe region 302 that are set so as to follow the shape of the diseased portion. Thus, it becomes possible to bring the arm distal end closer to the diseased portion in the default state.

Figure 21:
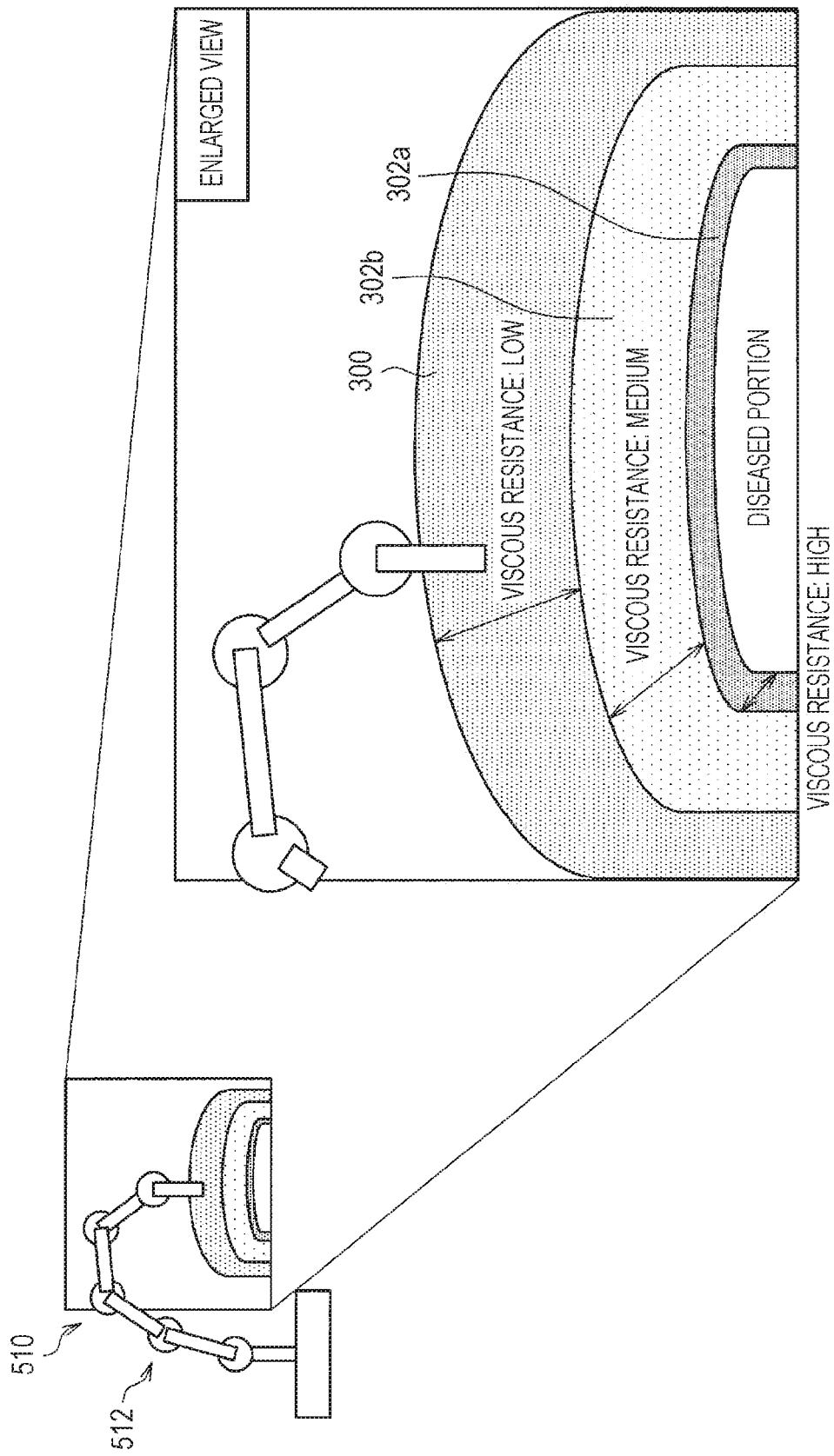
FIG. 21 is a schematic diagram illustrating an example in which, in the example illustrated in FIG. 18, a viscous resistance value is used as a parameter for restricting a movement of an arm distal end, and a larger viscous resistance (viscous load amount) is set to a region with a higher unsafe level.

FIG. 21 is a schematic diagram illustrating an example in which, in the example illustrated in FIG. 18, a viscous resistance value is used as a control parameter for restricting a movement of an arm distal end, and a higher viscous resistance coefficient (viscous load amount) is set to a region with a higher unsafe level. In this manner, by setting a higher unsafe level and a larger viscous load amount as getting closer to the diseased portion, a viscous load amount becomes larger as getting closer to the diseased portion. Thus, it is possible to cause a manipulator to surely recognize that the arm is being operated in a direction getting closer to the diseased portion, and enhance the safety. By setting a viscous resistance value for each region, and applying a viscous resistance value in a target region to all axes in accordance with the current position of the arm distal end, it is possible to suppress an excessive movement operation and guarantee the safety. Furthermore, in FIG. 21, within the safety movable range 300, by setting a higher viscous resistance coefficient as the arm distal end gets closer to the boundary between the safety movable range 300 and the unsafe region 302, even when the arm distal end is being operated within the safety movable range 300, it is possible to cause the manipulator to recognize that the arm distal end gets closer to the unsafe region 302.

Figure 22:
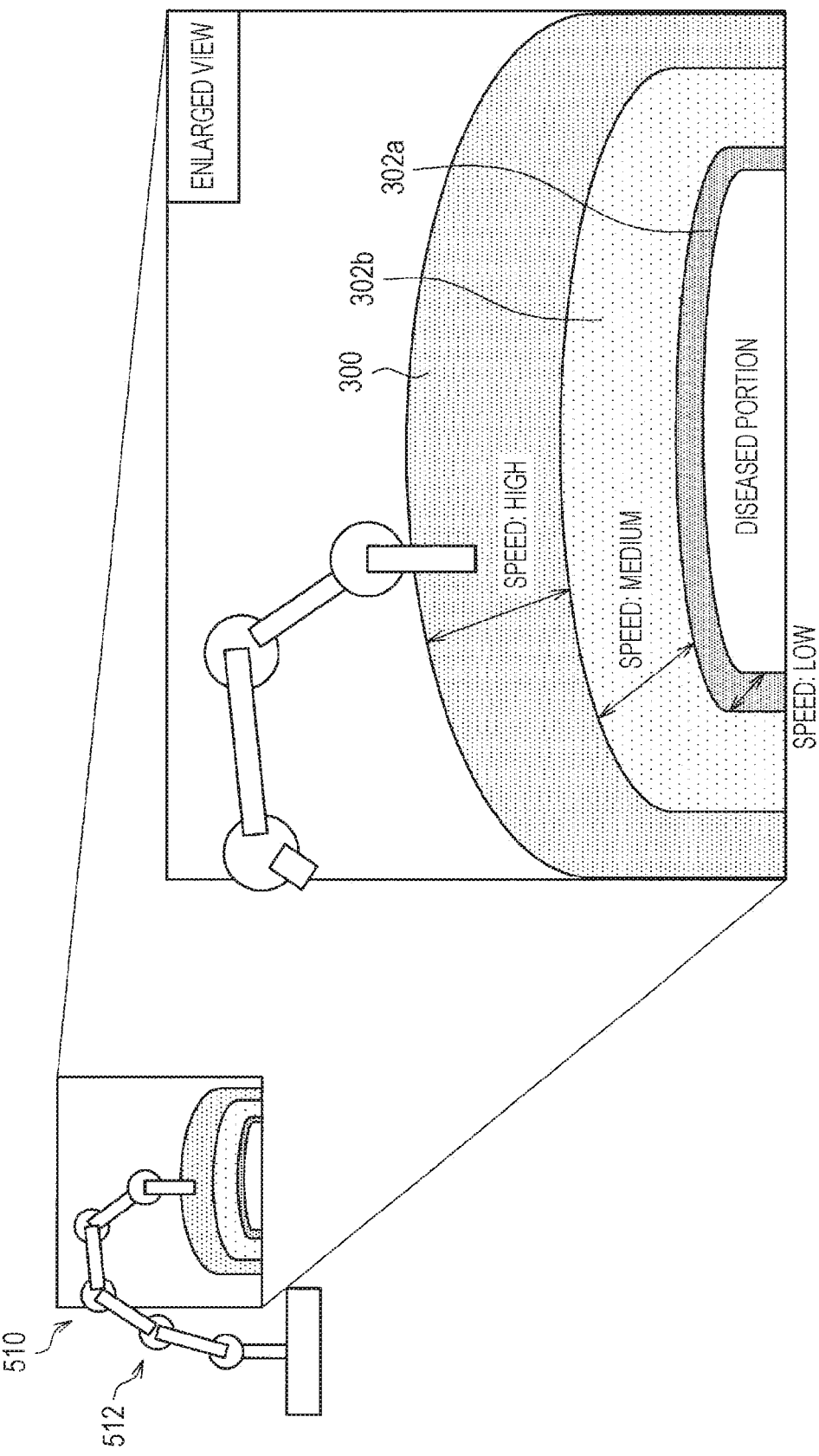
FIG. 22 is a schematic diagram illustrating an example in which, in the example illustrated in FIG. 18, a speed is used as a parameter for restricting a movement of an arm distal end, and a lower speed is set to a region with a higher unsafe level.

FIG. 22 is a schematic diagram illustrating an example in which, in the example illustrated in FIG. 18, a speed is used as a control parameter for restricting a movement of an arm distal end, and a speed is restricted to be lower in a region with a higher unsafe level. A speed limit value is set for each region, and in a case where the speed of the arm distal end position has reached the speed limit value, an optimum torque value of each axis is calculated in the total body harmonized control unit considering force in a suppression direction. It thereby is possible to suppress an excessive movement operation and guarantee the safety. In this manner, by setting a higher unsafe level and a lower speed as getting closer to the diseased portion, a speed decreases as getting closer to the diseased portion. Thus, it is possible to cause a manipulator to surely recognize that the arm is being operated in a direction getting closer to the diseased portion, and enhance the safety. Furthermore, also in FIG. 22, within the safety movable range 300, by setting a higher degree of speed limit as the arm distal end gets closer to the boundary between the safety movable range 300 and the unsafe region 302, even when the arm distal end is being operated within the safety movable range 300, it is possible to cause the manipulator to recognize that the arm distal end gets closer to the unsafe region 302.

3. Hardware Configuration

Figure 23:
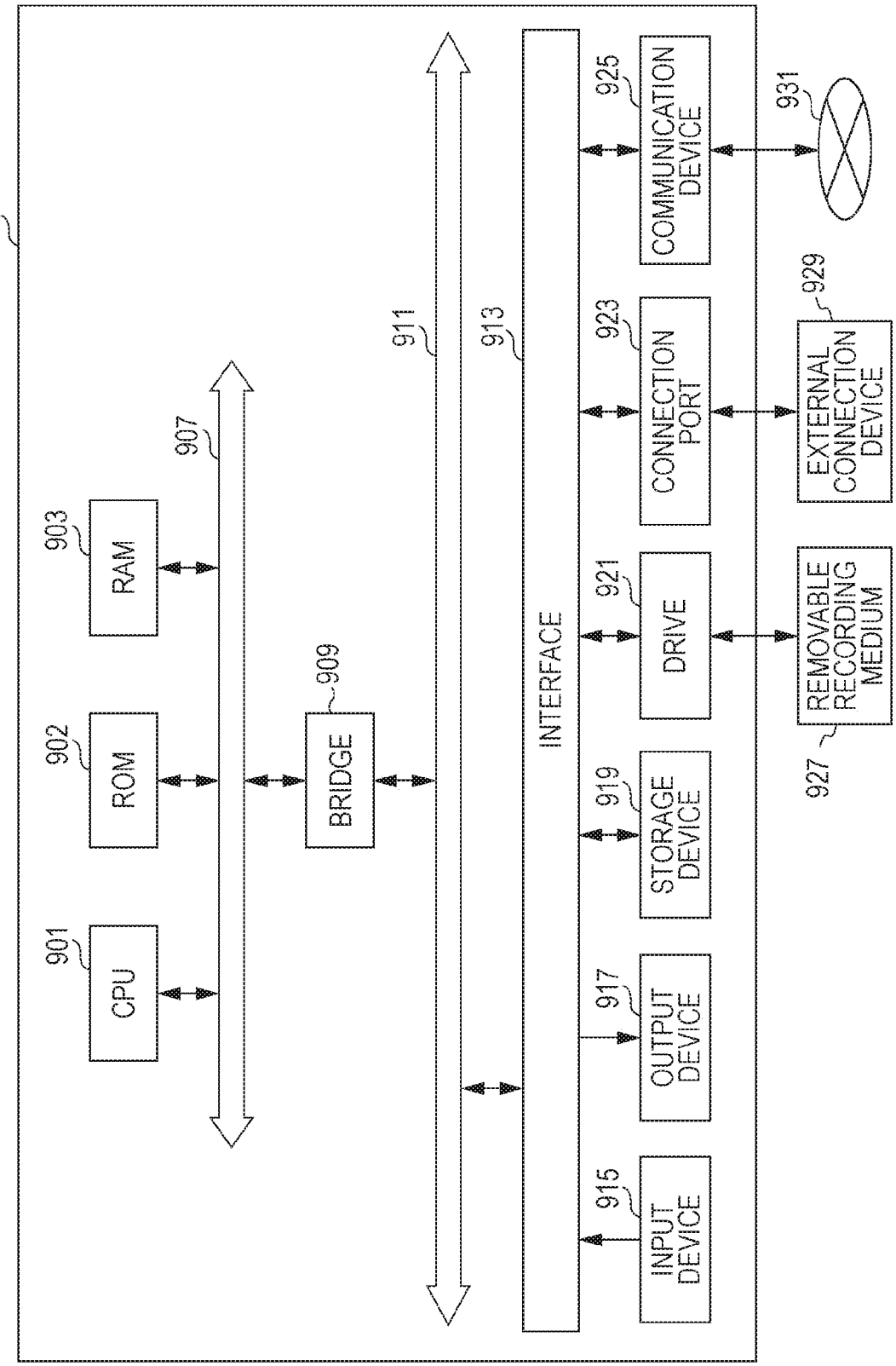
FIG. 23 is a functional block diagram illustrating a configuration example of a hardware configuration of a support arm device 10 and the control device 20 according to an embodiment of the present disclosure.

Next, a hardware configuration of the support arm device 10 and the control device 20 according to the present embodiment that are illustrated in FIG. 8 will be described in detail with reference to FIG. 23. FIG. 23 is a functional block diagram illustrating a configuration example of a hardware configuration of the support arm device 10 and the control device 20 according to an embodiment of the present disclosure.

Each of the support arm device 10 and the control device 20 mainly includes a CPU 901, a ROM 903, and a RAM 905. Furthermore, each of the support arm device 10 and the control device 20 moreover includes a host bus 907, a bridge 909, an external bus 911, an interface 913, an input device 915, an output device 917, a storage device 919, a drive 921, a connection port 923, and a communication device 925.

The CPU 901 functions as an arithmetic processing unit and a control device, and controls all or a part of the operations in the support arm device 10 and the control device 20 in accordance with various programs recorded in the ROM 903, the RAM 905, the storage device 919, or a removable recording medium 927. The ROM 903 stores programs, calculation parameters, or the like that are to be used in the CPU 901. The RAM 905 primarily stores programs to be used by the CPU 901, appropriately changing parameters in the execution of the programs, and the like. These components are connected to each other by the host bus 907 including an internal bus such as a CPU bus. In the present embodiment, the CPU 901 corresponds to the arm control unit 110 and the control unit 230 illustrated in FIG. 8, for example.

The host bus 907 is connected, via the bridge 909, to the external bus 911 such as a peripheral component interconnect/interface (PCI) bus. Furthermore, the input device 915, the output device 917, the storage device 919, the drive 921, the connection port 923, and the communication device 925 are connected to the external bus 911 via the interface 913.

The input device 915 is an operation means to be operated by the user, such as, for example, a mouse, a keyboard, a touch panel, a button, a switch, a lever, and a pedal. Furthermore, the input device 915 may be a remote-control means (so-called remote controller) that uses infrared rays or other radiowaves, for example, or may be an external connection device 929 such as a mobile phone or a PDA that supports operations of the support arm device 10 and the control device 20. Moreover, the input device 915 includes, for example, an input control circuit that generates an input signal on the basis of information input by the user using the above-described operation means, and outputs the input signal to the CPU 901, and the like. The user of the support arm device 10 and the control device 20 can input various data to the support arm device 10 and the control device 20 or instruct the support arm device 10 and the control device 20 to perform a processing operation, by operating the input device 915. In the present embodiment, the input device 915 corresponds to the input unit 210 illustrated in FIG. 8, for example. Furthermore, in the present embodiment, an exercise purpose in the driving of the arm portion 120 may be set by an operation input performed by the user via the input device 915, and total body harmonized control may be performed in accordance with the exercise purpose.

The output device 917 includes a device that can visually or aurally notify acquired information to the user. As such a device, there are display devices such as a CRT display device, a liquid crystal display device, a plasma display device, an EL display device, and a lamp, a sound output device such as a speaker or headphones, a printer device, and the like. The output device 917 outputs, for example, results obtained by various types of processing performed by the support arm device 10 and the control device 20. Specifically, a display device displays the results obtained by various types of processing performed by the support arm device 10 and the control device 20, as text or images. On the other hand, a sound output device coverts an audio signal including reproduced audio data, acoustic data, or the like, into an analog signal, and outputs the analog signal. In the present embodiment, various types of information regarding the driving control of the arm portion 120 may be output from the output device 917 in any format. For example, a trajectory of the movement of each component of the arm portion 120 in the driving control of the arm portion 120 may be displayed on a display screen of the output device 917 in the format of a graph. Note that, for example, the display device 30 illustrated in FIG. 8 may be a device having functions and configurations as a display device of the output device 917, and configurations of a control unit or the like for controlling the driving of the display device.

The storage device 919 is a device for data storage that is formed as an example of a storage unit of the support arm device 10 and the control device 20. The storage device 919 includes, for example, a magnetic storage unit device such as a hard disk drive (HDD), a semiconductor storage device, an optical storage device, a magnetooptical storage device, or the like. The storage device 919 stores programs executed by the CPU 901, various data, and the like. In the present embodiment, the storage device 919 corresponds to the storage unit 220 illustrated in FIG. 8, for example. Furthermore, in the present embodiment, the storage device 919 can store calculation conditions (an exercise purpose and a constraint condition) in the calculation regarding the total body harmonized control that uses the generalized inverse dynamics, and the support arm device 10 and the control device 20 may perform the calculation regarding the total body harmonized control, using these calculation conditions stored in the storage device 919.

The drive 921 is a reader/writer for a recording medium, and is built in the support arm device 10 and the control device 20 or externally attached thereto. The drive 921 reads out information recorded in the attached removable recording medium 927 such as a magnetic disc, an optical disk, a magnetooptical disk, or a semiconductor memory, and outputs the information to the RAM 905. Furthermore, the drive 921 can also write a record into the attached removable recording medium 927 such as a magnetic disc, an optical disk, a magnetooptical disk, or a semiconductor memory. The removable recording medium 927 is, for example, a DVD medium, an HD-DVD medium, a Blu-ray (registered trademark) medium, or the like. Furthermore, the removable recording medium 927 may be a CompactFlash (registered trademark) (CF), a flash memory, a secure digital (SD) memory card, or the like. Furthermore, the removable recording medium 927 may be, for example, an integrated circuit (IC) card equipped with a noncontact IC chip, an electronic device, or the like. In the present embodiment, various types of information regarding the driving control of the arm portion 120 may be read out from various removable recording media 927 by the drive 921, or may be written into various removable recording media 927.

The connection port 923 is a port for directly connecting a device to the support arm device 10 and the control device 20. As an example of the connection port 923, there is a universal serial bus (USB) port, an IEEE1394 port, a small computer system interface (SCSI) port, or the like. As another example of the connection port 923, an RS-232C port, an optical audio terminal, a high-definition multimedia interface (HDMI) (registered trademark) port, or the like. By connecting the external connection device 929 to the connection port 923, the support arm device 10 and the control device 20 directly acquire various data from the external connection device 929, and provide various data to the external connection device 929. In the present embodiment, various types of information regarding the driving control of the arm portion 120 may be read out from various external connection devices 929 via the connection port 923, or may be written into various external connection devices 929.

The communication device 925 is a communication interface including a communication device or the like for connecting to a communication network 931, for example. The communication device 925 is, for example, a wired or wireless local area network (LAN), Bluetooth (registered trademark), a communication card for a wireless USB (WUSB), or the like. Furthermore, the communication device 925 may be a router for optical communication, a router for Asymmetric Digital Subscriber Line (ADSL), various communication modems, or the like. The communication device 925 can transmit and receive a signal or the like in compliance with a predetermined protocol such as TCP/IP, for example, with the Internet or another communication device, for example. Furthermore, the communication network 931 connected to the communication device 925 includes a network and the like connected in a wired or wireless manner, and may be, for example, the Internet, home LAN, infrared communication, radiofrequency communication, satellite communications, or the like. In the present embodiment, various types of information regarding the driving control of the arm portion 120 may be transmitted to or received from another external device by the communication device 925 via the communication network 931.

Heretofore, an example of a hardware configuration that can implement functions of the support arm device 10 and the control device 20 according to an embodiment of the present disclosure has been described. Each of the above-described components may be formed using a general-purpose member, or may be formed by hardware dedicated to the function of each component. Accordingly, a hardware configuration to be used can be appropriately changed in accordance with a technology level when the present embodiment is implemented. Note that the support arm device 10 naturally includes various configurations corresponding to the arm portion 120 illustrated in FIG. 8, which are not illustrated in FIG. 23.

Note that it is possible to create a computer program for implementing each function of the support arm device 10, the control device 20, and the display device 30 according to the present embodiment as mentioned above, and mount the computer program onto a personal computer or the like. Furthermore, it is possible to provide a computer-readable recording medium storing such a computer program. The recording medium is, for example, a magnetic disc, an optical disk, a magnetooptical disk, a flash memory, or the like. Furthermore, the above-described computer program may be delivered via a network, for example, without using a recording medium.

4. Conclusion

As described above, according to a medical system including the control device 20 according to an embodiment of the present disclosure, a function of controlling an operation of a working point on the basis of an acquired safety movable range of the other support arm device 10, a safety movable range of the support arm device 10 serving as a control target, and a space position of the working point is included. With this configuration, it becomes possible to more accurately control a harmonized operation of a plurality of medical support arms.

Heretofore, a preferred embodiment of the present disclosure has been described in detail with reference to the attached drawings, but the technical scope of the present disclosure is not limited to this example. It should be appreciated that a person who has general knowledge in the technical field of the present disclosure can conceive various change examples and modified examples within the scope of the technical idea described in the appended claims, and these change examples and modified examples are construed as naturally falling within the technical scope of the present disclosure.

Furthermore, the effects described in this specification are merely provided as explanatory or exemplary effects, and the effects are not limited. That is, the technology according to the present disclosure can bring about another effect obvious for the one skilled in the art, from the description in this specification, in addition to the above-described effects or in place of the above-described effects.

Furthermore, steps in the processing of the control device 20 in this specification need not be always processed chronologically along an order described in the flowchart. For example, steps in the processing of the control device 20 may be processed in an order different from the order described in the flowchart, or may be concurrently processed.

Note that the following configurations also fall within the technical scope of the present disclosure.

(1)) A medical system including:
an operation control unit configured to control, on the basis of information regarding a movable range of a first medical support arm being a control target, information regarding the movable range of a second medical support arm to be used together with the first medical support arm, and a space position of a working point in the first medical support arm, an operation of the working point.

(2)) The medical system according to (1)) described above, in which
the operation control unit controls an operation of the working point on the basis of a region in which the movable range of the first medical support arm and the movable range of the second medical support arm overlap or abut, and a space position of the working point in the first medical support arm.

(3)) The medical system according to (2)) described above, in which
the operation control unit controls an operation of the working point in the first medical support arm on the basis of a set operation mode.

(4)) The medical system according to (3)) described above, in which
in a case where the operation mode is a movable range share mode, the operation control unit restricts an operation of the working point in a case where the working point in the first medical support arm enters an unsafe region over a shared movable range being a region obtained by adding the movable range of the first medical support arm and the movable range of the second medical support arm.

(5)) The medical system according to (3)) described above, in which
in a case where the operation mode is a collision avoidance mode, and priority of the first medical support arm is higher than priority of the second medical support arm, the operation control unit restricts an operation of the working point in a case where the working point in the first medical support arm enters an unsafe region over the movable range of the first medical support arm.

(6)) The medical system according to (3)) or (5)) described above, in which
in a case where the operation mode is a collision avoidance mode, and priority of the first medical support arm is lower than priority of the second medical support arm, the operation control unit restricts an operation of the working point on the basis of the working point in the first medical support arm being positioned in an interference region with the second medical support arm.

(7)) The medical system according to (6)) described above, in which
the operation control unit restricts an operation of the working point to an avoidance movement to a non-interference region in the movable range of the first medical support arm, on the basis of the working point in the first medical support arm being positioned in the interference region.

(8)) The medical system according to (3)) described above, in which
in a case where the operation mode is a collision suppression mode, the operation control unit restricts an operation of the working point on the basis of the working point in the first medical support arm being positioned in an interference region with the second medical support arm.

(9)) The medical system according to any of (1)) to (8)) described above, further including:
A movable range information acquisition unit configured to acquire information regarding the movable range of the second medical support arm.

(10)) The medical system according to any of (1)) to (9)) described above, further including:
A movable range update unit configured to expand, in a case where the working point in the first medical support arm enters an unsafe region over the movable range of the first medical support arm, the movable range in accordance with the entry of the working point into the unsafe region.

(11)) The medical system according to any of (1)) to (10)) described above, further including:
A movable range information transmission unit configured to transmit, on the basis of the movable range of the first medical support arm being updated, information regarding the updated movable range, to a control unit configured to restrict an operation of the second medical support arm.

(12)) The medical system according to (7)) described above, in which
the non-interference region is a region obtained by subtracting the movable range of the second medical support arm from the movable range of the first medical support arm.

(13)) The medical system according to any of (6)) to (8)) described above, in which
the interference region is a region in which the movable range of the first medical support arm and the movable range of the second medical support arm overlap.

(14)) The medical system according to any of (1)) to (13)) described above, in which
the operation control unit controls an operation of the working point on the basis of a control parameter for controlling an operation of the working point in the first medical support arm.

(15)) The medical system according to (14)) described above, in which
the control parameter is a viscous resistance coefficient of an operation in a joint portion included in the first medical support arm.

(16)) The medical system according to (14)) described above, in which
the control parameter is a speed of the working point.

(17)) The medical system according to any of (1)) to (16)) described above, in which
the working point is a distal end portion of the first medical support arm, at least one of a plurality of links included in the first medical support arm, or at least one of a plurality of joint portions.

(18)) The medical system according to any of (1)) to (17)) described above, further including:
an automatic control unit configured to automatically move the working point in the first medical support arm within the movable range of the first medical support arm.

(19)) The medical system according to any of (1)) to (18)) described above, further including:
A position acquisition unit configured to detect a space position of the working point in the first medical support arm.

(20)) The medical system according to any of (1)) to (19)) described above, further including:
the first medical support arm.

(21)) A control device of a medical support arm including:
an operation control unit configured to control, on the basis of information regarding a movable range of a first medical support arm being a control target, information regarding the movable range of a second medical support arm to be used together with the first medical support arm, and a space position of a working point in the first medical support arm, an operation of the working point.

(22)) A control method of a medical support arm, the control method including:
controlling, by a processor, on the basis of information regarding a movable range of a first medical support arm being a control target, information regarding the movable range of a second medical support arm to be used together with the first medical support arm, and a space position of a working point in the first medical support arm, an operation of the working point.

REFERENCE SIGNS LIST

10 Support arm device
20 Control device
222 Operation region storage unit
241 Arm state acquisition unit (position acquisition unit)
245 Movable range information acquisition unit
246 Shared movable range operation decision unit
247 Movable range information transmission unit
270 Movable range intraregional determination unit
272 Ideal model condition decision unit (operation control unit)
274 Movable range update unit

The invention claimed is:

1. A medical system comprising:
an operation control unit configured to control, on a basis of information regarding a movable range of a first medical support arm being a control target, information regarding the movable range of a second medical support arm to be used together with the first medical support arm, and a space position of a working point in the first medical support arm, an operation of the working point.

2. The medical system according to claim 1, wherein
the operation control unit controls an operation of the working point on a basis of a region in which the movable range of the first medical support arm and the movable range of the second medical support arm overlap or abut, and a space position of the working point in the first medical support arm.

3. The medical system according to claim 2, wherein
the operation control unit controls an operation of the working point in the first medical support arm on a basis of a set operation mode.

4. The medical system according to claim 3, wherein
in a case where the operation mode is a movable range share mode, the operation control unit restricts an operation of the working point in a case where the working point in the first medical support arm enters an unsafe region over a shared movable range being a region obtained by adding the movable range of the first medical support arm and the movable range of the second medical support arm.

5. The medical system according to claim 3, wherein
in a case where the operation mode is a collision avoidance mode, and priority of the first medical support arm is higher than priority of the second medical support arm, the operation control unit restricts an operation of the working point in a case where the working point in the first medical support arm enters an unsafe region over the movable range of the first medical support arm.

6. The medical system according to claim 3, wherein
in a case where the operation mode is a collision avoidance mode, and priority of the first medical support arm is lower than priority of the second medical support arm, the operation control unit restricts an operation of the working point on a basis of the working point in the first medical support arm being positioned in an interference region with the second medical support arm.

7. The medical system according to claim 6, wherein
the operation control unit restricts an operation of the working point to an avoidance movement to a non-interference region in the movable range of the first medical support arm, on a basis of the working point in the first medical support arm being positioned in the interference region.

8. The medical system according to claim 3, wherein
in a case where the operation mode is a collision suppression mode, the operation control unit restricts an operation of the working point on a basis of the working point in the first medical support arm being positioned in an interference region with the second medical support arm.

9. The medical system according to claim 1, further comprising:
a movable range information acquisition unit configured to acquire information regarding the movable range of the second medical support arm.

10. The medical system according to claim 1, further comprising:
a movable range update unit configured to expand, in a case where the working point in the first medical support arm enters an unsafe region over the movable range of the first medical support arm, the movable range in accordance with the entry of the working point into the unsafe region.

11. The medical system according to claim 1, further comprising:
   a movable range information transmission unit configured to transmit, on a basis of the movable range of the first medical support arm being updated, information regarding the updated movable range, to a control unit configured to restrict an operation of the second medical support arm.

12. The medical system according to claim 7, wherein the non-interference region is a region obtained by subtracting the movable range of the second medical support arm from the movable range of the first medical support arm.

13. The medical system according to claim 6, wherein the interference region is a region in which the movable range of the first medical support arm and the movable range of the second medical support arm overlap.

14. The medical system according to claim 1, wherein the operation control unit controls an operation of the working point on a basis of a control parameter for controlling an operation of the working point in the first medical support arm.

15. The medical system according to claim 14, wherein the control parameter is a viscous resistance coefficient of an operation in a joint portion included in the first medical support arm.

16. The medical system according to claim 14, wherein the control parameter is a speed of the working point.

17. The medical system according to claim 1, wherein the working point is a distal end portion of the first medical support arm, at least one of a plurality of links included in the first medical support arm, or at least one of a plurality of joint portions.

18. The medical system according to claim 1, further comprising:
   an automatic control unit configured to automatically move the working point in the first medical support arm within the movable range of the first medical support arm.

19. The medical system according to claim 1, further comprising:
   a position acquisition unit configured to detect a space position of the working point in the first medical support arm.

20. The medical system according to claim 1, further comprising:
   the first medical support arm.

21. A control device of a medical support arm comprising:
   an operation control unit configured to control, on a basis of information regarding a movable range of a first medical support arm being a control target, information regarding the movable range of a second medical support arm to be used together with the first medical support arm, and a space position of a working point in the first medical support arm, an operation of the working point.

22. A control method of a medical support arm, the control method comprising:
   controlling, by a processor, on a basis of information regarding a movable range of a first medical support arm being a control target, information regarding the movable range of a second medical support arm to be used together with the first medical support arm, and a space position of a working point in the first medical support arm, an operation of the working point.

* * * * *